(12) United States Patent
Scott et al.

(10) Patent No.: US 7,767,391 B2
(45) Date of Patent: Aug. 3, 2010

(54) USE OF INTRONIC RNA TO MEASURE GENE EXPRESSION

(75) Inventors: Randy Scott, Los Altos, CA (US); Joffre B. Baker, Montara, CA (US); Michael C. Kiefer, Clayton, CA (US)

(73) Assignee: Genomic Health, Inc., Redwood City, CA (US)

( * ) Notice: Subject to any disclaimer, the term of this patent is extended or adjusted under 35 U.S.C. 154(b) by 410 days.

(21) Appl. No.: 10/783,884

(22) Filed: Feb. 19, 2004

(65) Prior Publication Data

US 2004/0191817 A1    Sep. 30, 2004

Related U.S. Application Data

(60) Provisional application No. 60/448,991, filed on Feb. 20, 2003.

(51) Int. Cl.
 C12Q 1/68     (2006.01)
 C12P 19/34    (2006.01)
 C07H 21/04    (2006.01)

(52) U.S. Cl. .......................... 435/6; 435/91.2; 536/24.3

(58) Field of Classification Search ........................ None
 See application file for complete search history.

(56) References Cited

U.S. PATENT DOCUMENTS

| | | | |
|---|---|---|---|
| 4,699,877 A | 10/1987 | Cline et al. | 435/6 |
| 4,968,603 A | 11/1990 | Slamon et al. | 435/6 |
| 5,015,568 A | 5/1991 | Tsujimoto et al. | 435/5 |
| 5,202,429 A | 4/1993 | Tsujimoto et al. | 536/23.5 |
| 5,459,251 A | 10/1995 | Tsujimoto et al. | 536/23.5 |
| RE35,491 E | 4/1997 | Cline et al. | 435/6 |
| 5,670,325 A | 9/1997 | Lapidus et al. | 435/6 |
| 5,741,650 A | 4/1998 | Lapidus et al. | 435/6 |
| 5,830,665 A | 11/1998 | Shuber et al. | 435/6 |
| 5,830,753 A | 11/1998 | Coulie et al. | 435/325 |
| 5,858,678 A | 1/1999 | Chinnadurai | 435/7.1 |
| 5,861,278 A | 1/1999 | Wong et al. | 435/69.1 |
| 5,928,870 A | 7/1999 | Lapidus et al. | 435/6 |
| 5,952,178 A | 9/1999 | Lapidus et al. | 435/6 |
| 5,952,179 A | 9/1999 | Chinnadurai | 435/6 |
| 5,962,312 A | 10/1999 | Plowman et al. | 435/320.1 |
| 5,985,553 A | 11/1999 | King et al. | 435/6 |
| 6,020,137 A | 2/2000 | Lapidus et al. | 435/6 |
| 6,100,029 A | 8/2000 | Lapidus et al. | 435/6 |
| 6,143,529 A | 11/2000 | Lapidus et al. | 435/91.2 |
| 6,146,828 A | 11/2000 | Lapidus et al. | 435/6 |
| 6,171,798 B1 | 1/2001 | Levine et al. | 435/6 |
| 6,203,993 B1 | 3/2001 | Shuber et al. | 435/6 |
| 6,207,401 B1 | 3/2001 | Plowman et al. | 435/15 |
| 6,207,452 B1 | 3/2001 | Govindaswamy | 435/330 |
| 6,214,558 B1 | 4/2001 | Shuber et al. | 435/6 |
| 6,245,523 B1 | 6/2001 | Altieri | 435/69.1 |
| 6,248,535 B1 | 6/2001 | Danenberg et al. | 435/6 |
| 6,271,002 B1 | 8/2001 | Linsley et al. | 435/91.1 |
| 6,322,986 B1 | 11/2001 | Ross | 435/6 |
| 6,414,134 B1 | 7/2002 | Reed | 536/24.5 |
| 6,582,919 B2 | 6/2003 | Danenberg | 435/6 |
| 6,602,670 B2 | 8/2003 | Danenberg | 435/6 |
| 6,618,679 B2 | 9/2003 | Loehrlein et al. | 702/20 |
| 6,620,606 B2 | 9/2003 | Bandman et al. | 435/219 |
| 6,696,558 B2 | 2/2004 | Reed et al. | 536/23.5 |
| 6,716,575 B2 | 4/2004 | Plowman et al. | 435/6 |
| 6,750,013 B2 | 6/2004 | Gish et al. | 435/6 |
| 6,800,737 B2 | 10/2004 | Altieri | 530/386 |
| 6,943,150 B1 | 9/2005 | Altieri | 514/21 |
| 7,026,123 B1 * | 4/2006 | Duvick | 435/6 |
| 2001/0029018 A1 * | 10/2001 | Danenberg et al. | 435/6 |
| 2001/0053519 A1 * | 12/2001 | Fodor et al. | 435/6 |
| 2002/0004491 A1 | 1/2002 | Xu et al. | 514/44 |
| 2002/0009736 A1 | 1/2002 | Wang | 435/6 |
| 2002/0009795 A1 * | 1/2002 | Danenberg et al. | 435/270 |
| 2002/0039764 A1 | 4/2002 | Rosen | 435/69.1 |
| 2002/0160395 A1 | 10/2002 | Altieri et al. | 435/6 |
| 2003/0073112 A1 | 4/2003 | Zhang et al. | 435/6 |
| 2003/0104499 A1 | 6/2003 | Pressman et al. | 435/7.23 |
| 2003/0165952 A1 | 9/2003 | Linnarsson et al. | 435/6 |
| 2003/0180791 A1 | 9/2003 | Chinnadurai | 435/6 |

(Continued)

FOREIGN PATENT DOCUMENTS

EP    0 108 564 B1    5/1988

(Continued)

OTHER PUBLICATIONS

GenBank GI:8052236, May 22, 2000, [online], [retrieved on Jan. 30, 2007], retrieved from the Internet: <URL: http://www.ncbi.nlm.nih.gov/entrez/viewer.fcgi?8052236:OLD03:209064>, pp. 1-71.*
Buck et al. Design strategies and performance of custom DNA sequencing primers. BioTechniques, 1999, vol. 27, pp. 528-536.*
Coleclough et al. Introns excised from immunoglobulin pre-mRNAs exist as discrete species. Molecular and Cellular Biology, Oct. 1984, vol. 4, No. 10, pp. 2017-2022.*
Lipson et al. Transcriptional activity of the human thymidine kinase gene determined by a method using the polymerase chain reaction and an intron-specific probe. PNAS 86:9774-7 (1989).*
Chang et al. Analysis of tyrosine hydroxylase gene transcription using an intron specific probe. Journal of Neuroscience Methods 94:177-85 (2000).*
Matsubara et al. Quantitative analysis of growth hormone (GH) pre-mRNA expression in cultured rat anterior pituitary cells by an intron-specific and competitive PCR method. Endocrinology 138(11):5075-8 (1997).*

(Continued)

Primary Examiner—Samuel Woolwine
(74) Attorney, Agent, or Firm—James S. Keddie; Carol L. Francis; Bozicevic, Field & Francis LLP

(57) ABSTRACT

The invention is based on the use of intronic RNA in monitoring gene expression. Accordingly, the present invention concerns methods of gene expression profiling using intronic RNA, the expression of which correlates with the expression of corresponding exonic RNA, and diagnostic and prognostic methods based on the results of such gene expression studies.

7 Claims, 27 Drawing Sheets

U.S. PATENT DOCUMENTS

| | | | |
|---|---|---|---|
| 2003/0198970 A1 | 10/2003 | Roberts | 435/6 |
| 2003/0198972 A1 | 10/2003 | Erlander et al. | 435/6 |
| 2003/0219771 A1 | 11/2003 | Bevilacqua et al. | 435/6 |
| 2003/0224374 A1* | 12/2003 | Dai et al. | 435/6 |
| 2003/0229455 A1 | 12/2003 | Bevilacqua et al. | 702/20 |
| 2004/0009489 A1 | 1/2004 | Golub et al. | 435/6 |
| 2004/0126775 A1 | 7/2004 | Altieri et al. | 435/6 |
| 2004/0133352 A1 | 7/2004 | Bevilacqua et al. | 702/19 |

FOREIGN PATENT DOCUMENTS

| | | |
|---|---|---|
| EP | 1 365 034 | 11/2003 |
| WO | WO 99/02714 | 1/1999 |
| WO | WO 00/50595 | 8/2000 |
| WO | WO 00/55173 | 9/2000 |
| WO | WO 01/25250 | 4/2001 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/46467 | 6/2002 |
| WO | WO 02/017852 | 7/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/011897 | 2/2003 |
| WO | WO 03/083096 | 10/2003 |

OTHER PUBLICATIONS

Burns, C.G. et al., "Removal of a Single α-Tubulin Gene Intron Suppresses Cell Cycle Arrest Phenotypes of Splicing Factor Mutations in *Saccharomyces cerevisiae*", Molecular and Cell Biology, vol. 22, No. 3, pp. 801-815, Feb. 2002.

Clark, Tyson A. et al., "Genomewide Analysis of mRNA Processing in Yeast Using Splicing-Specific Microarrays", Science, vol. 296, No. 5569, pp. 907-910, May 3, 2002.

Kapranov, Philipp, et al., "Large-Scale Transcriptional Activity in Chromosomes 21 and 22", Science, vol. 296, No. 5569, pp. 916-919, May 3, 2002.

Schneider J., et al., "Expression of LRP and MDR1 in Locally Advanced Breast Cancer Predicts Axillary Node Invasion at the Time of Rescue Mastectomy after Induction Chemotherapy", Breast Cancer Research, vol. 3, No. 3, pp. 183-191, 2001.

Thomázy, Vilmos A., et al, "Determination of Cyclin D1 and CD20 mRNA Levels by Real-Time Quantitative RT-PCR from Archival Tissue Sections of Mantle Cell Lyphoma and Other Non-Hodgkin's Lymphomas", The Journal of Molecular Diagnostics, vol. 4, No. 4, pp. 201-208, Nov. 2002.

Clement et al., "Localization and Stability of Introns Spliced from the *Penn* Homebox Gene", The Journal of Biological Chemistry, vol. 276, No. 20, pp. 16919-16930, 2001.

Clement et al.,"The stability and fate of a spliced intron from vertebrate cells", RNA, vol. 5, pp. 206-220, 1999.

Elliott et al., "Yeast Pre-mRNA Is Composed of Two Populations with Distinct Kinetic Properties", Experimental Cell Research, vol. 229, pp. 181-188, 1996.

Godfrey et al., "Quantatative mRNA Expression Analysis from Formalin-Fixed, Parraffin-Embedded Tissues Using 5' Nuclease Quantitative Reverse Transcription-Polymerase Chain Reaction", Journal of . Molecular Diagnostics, vol. 2, No. 2, pp. 84-91, May 2000.

Lewin, Benjamin, *Genes IV.*, pp. 810 and 812, Oxford University Press, Cell Press, Cambridge Mass. 1990.

Padgett et al, "Splicing of Messenger RNA Precusors", Ann. Rev. Biochem., vol. 55, pp. 1119-1150, 1986.

Specht et al., "Quantitative Gene Expression Analyssi in Microdissected Archival Formalin-Fixed and Paraffin-Embedded Tumor Tissue", American Journal of Pathology, vol. 158, No. 2, pp. 419-429, 2001.

Thomas et al., "The 2-Kilobase Intron of the Herpes Simplex Virus Type 1 Latency-Associated Transcript Has a Half-Life of Approximately 24 Hours in SY5Y and COS-1 Cells," Journal of Virology, pp. 532-540, Jan. 2002.

Wang et al., "Regulation of insulin preRNA splicing by glucose", Proc. Natl. Acad. Sci. USA, vol. 94, pp. 4360-4365, Apr. 1997.

Brabender, Jan, et al.; *Epidermal Growth Factor Receptor and HER2-neu mRNA Expression in Non-Small Cell Lung Cancer Is Correlated with Survival*, Clinical Cancer Research; vol. 7, Jul. 2001; pp. 1850-1855.

Ding, Chunming, et al.; *A high-throughput gene expression analysis technique using competitive PCR and matrix-assisted laser desorption ionization time-of-flight MS*, PNAS, vol. 100:6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; *BADGE, BeadsArray for the Detection of Gene Expression, a High-Throughput Diagnostic Bioassay*; Genome Research; vol. 11; 2001; pp. 1888-1898.

Bousquet-Antonelli, et al. Identification of a regulated pathway for nuclear pre-mRNA turnover. Cell. 2000, vol. 102, pp. 765-775.

Burton, E., et al. The stable 2.0-kilobase intron of the herpes simplex virus type 1 latency-associated transcript does not function as an antisense repressor of ICP0 in nonneuronal cells. Journal of Virology. 2003, vol. 77, pp. 3516-3530.

Krummenacher, C., et al. Selection of a nonconsensus branch point is influenced by an RNA stem-loop structure and is important to confer stability to the herpes simplex virus 2-kilobase latency-associated transcript. Journal of Virology. 1997, vol. 71, pp. 5849-5860.

Kulesza, C., et al. Murine cytomegalovirus encodes a stable intron that facilitates persistent replication in the mouse. PNAS. 2006, vol. 103, pp. 18302-18307.

Mukerjee, R., et al. A non-consensus branch point plays an important role in determining the stability of the 2-kb LAT intron during acute and latent infections of herpes simplex virus type-1. Virology. 2004, vol. 324, pp. 340-349.

Ng, A., et al. Construction of a herpes simplex virus type 1 mutant with only a three-nucleotide change in the branchpoint region of the latency-associated transcript (LAT) and the stability of its two-kilobase LAT intron. Journal of Virology. 2004, vol. 78, pp. 12097-12106.

Sharp, P. Split genes and RNA splicing. Cell. 1994, vol. 77, pp. 805-815.

Hollander, V., et al. Group II intron splicing in chloroplasts: identification of mutations determining intron stability and fate of exon RNA. Nucleic Acids Research. 1999, vol. 27, No. 11, pp. 2345-2353.

Nam, K., et al. Severe growth defect in a schizosaccharomyces pombe mutant defective in intron lariat degradation. Molecular and Cellular Biology. 1997, vol. 17, No. 2, pp. 809-818.

Carey, J., et al. Transcriptional regulation of muscle fatty acid-binding protein. The Biochemical Journal. 1994, vol. 298, pp. 613-617.

Fan, J., et al. Global analysis of stress-regulated mRNA turnover by using cDNA arrays. PNAS. 2002, vol. 99, No. 16, pp. 10611-10616.

Hanash, S., et al. Operomics: Integrated genomic and proteomic profiling of cells and tissues. Briefings in Funtional Genomics and Proteomics. 2002, vol. 1, No. 1, pp. 10-22.

Hatzoglou, M., et al., Processing of phosphoenolpyruvate carboxykinase (GTP) RNA in vivo. PNAS. 1985, vol. 82, pp. 4346-4350.

Xu, W.-B., et al. The gene encoding human ribosomal protein S24 and tissue-specific expression of differentially spliced mRNAs. Gene. 1996, vol. 169, pp. 257-262.

\* cited by examiner

Figures 1A-M

>CEGP1 intron 1, 1566 bases
GTGAGTGTCCGGCCGCGGGGGCGCACCTGGCACAGCAGGCAGGGCCAGGA
AGAGTGTTTAGGTCCCCGGCGGAGTCCAGAGCCGGGCGCGCGGGGCTCGG
GGCTGGCGGCTGCAGCTCCGCGGGGGCCTCTGCTCCCCCCGGGACCTCAC
CCGCCGGCCGGGCCAAGGCGCCACGACCGCTGGGGCCCTGAGTCCTTCGG
CCCGGCCTCGGACCCGGAGCTGCTGACGGTTCCCGCCCCGGTCCGGATGC
CTCCAGAGCGCCTGCTAGTCAGACCGTCGCCGGCGAGCAGGCAGGAGGGT
GCGGACCCTGGCCTTGGGGTCCCGCGCCTCAGCGTAGGCGGGGAAACTGA
GGGCCGGGCCGGGCACATCCGCGAGGCGGTGGCAGCTTTGCCGTTTCTTT
CTTTGGGGGCCGGCAAGTTCTGCTGATGGCTTCGGGGTGGGCTCCAGAGA
CTTTTCTGTCAGCGGAAC*AGCGCCTGTTCCGATCTGGGAATTACCCTGAA*
*GCAGCAACAAGCCTAGGTTTTCAGCAGAGAACTTTGGTTTCCAGAGAGGA*
CTCTGGACGTGCTGTGCTTACTGGACTTGCAATACTTTCAAAATGCTTTT
GTTTTTAATTAATATCCTGGAGTAGTGTCAACCCAGGAAATACTTCTGCC
AAGGCGGGTTTCCAGGTTGAGAGGATGGGCAGGGGTGGGAGTGCAGGGGG
CCGGCCATGGGGACACCATCCCCGCTTCGCAGCATCTGAGAGCCCTGGAT
GACATCTGCTCCGATCCCGGGGCAGACTTCCCATAAATACTCTAAACCAG
CNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNCTCTGAGCTCCGAGAAAGCTGAC
AGACAGCTGCTTGGTGTTCAGAGCTTGTCTGTCCGTTTGGTCCTTTCCTC
CTTTAGCGGGCATGTAGGTACTATTNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNCACATGGCCTGGGAGCCTGTACCAGGTGTCAG
CTGTGCTCTTTTGCAG (SEQ ID NO.: 1)

```
MGB-CEGP1 int1.1
```

FIG.1A

>CEGP1 intron 4, 4985 bases
GTACCTCTGCCCAGCTGTGGATGGGGGCAGAGCCACATCTGAGACCCTCT
CCCTTGCACGCGCACACACACACTGACTCTAGNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNATCTTTACATAGAATACATTTCAAACATGACTAGATGTCTCAGGAGC
AATATAGTGGATGATCTGCCAAGTTTTTCAAAAAGGTGCTGAAAACCACA
GCACCAGTATGAGCCTGCTCCCTGCTCTGGGTGGGTAGGGAGGAGGCTGG
ATCCTTCCCATGCAGACTTTCAATGAAGTGCCCTGTTTTCAGCCCCAAGC
TAGATCCGGCCCTTCCATGTTTTGCATTTTGAGCTCCGAGGGGCAGAAG
GGCTCCCTCCCTGGACTTTCCGTGCTGTGGTTTCCTTCGCCTACGTCACC
ATTTATCATTCCTCTGTAAATTTGCGGAAACTCTTCTCTTCTGATGTCC
TTCTCTTCATTCTCTTTGCTTTGAGTTTATACCTTTTTTCATTCCTCTGT
TACTTAGTAGATTCTTGAGAGGAAGGGCATTAAGTACATGTGGCCAATC
AGTTATTTTAACTGAATGTCATCCTTTTAACTCTTCCCTGCTCTTTCTT
AAGCTAAAGAGTCACATTTTGGTGGCTGTGTTCCTCTTGGAGTTGCATCT
GCCTATTTTAGGGGAAGTGCCCTAAATACTAGCCTATTAACCCCTTTGG
CCATGTGCTGCTTATTCTTTCCCATTACTTAAGAATGAGGTCATTTTAAT
TTCTTCTACTATTTAATCACAAATTTATAGATTGTTTTAATCCTGGTCTT
GGTAACTTTTCAAGGGTTTCTTCATGGAAGATGATTTTTGTCTCATTTTC
```

```
CAAGGATGGCAGCTCACACCTTATACTTAACTAGAATACCTGTTTGGGTA
CCAAGAAAAATTGTCAGAGGAACCCCCAGGGGCCAATGGGTTTGATGGCT
ATCATCACCCAGAGCCTGCTCATTCTCAGCGTTTGGGGCGGGGAAGTCAC
ACATACTGGCTTTGATCAGGCAGATTTCCTATCTTGTGCCAGGTGTGGCC
CTTGATAAAGTAGCAGTTGGGTTTCATTTTCCTGCCAGGTTCTCTGGGGT
CATTGGTGTGCCCTGCACTCTTGTCCAATGTAGGCCAAATTCGAGATGGG
AATGAATTAGGAGGCCAGTGGCACAGAGTGATCCGAATCTCAGGGCATCT
CTCCTTTTGATTGCTCAAAGCTGCTTCCTGGGAAGTCACTTTGGCTTCCT
CTGCAGGTGGCTGGGGAGGGATGTGGGAACTGCAGGTTAAAGCCATCGCT
TGAGCCCTCACGGTCTGGGTCCCACCCAGTTACAAAGCAGCTGGTAGCGA
TTAAGATCACCTCTTATCCCTGTACTTCCAGAGCCCTGGCTCAGCCCCAC
TCTCCCCTCCTGCAAGCCCCCGGACTGATTAGAGACACAGGCTCCTCATA
CCAGAAGCAAATACAAATGCAGTTCCTTTCTGCAAACTGTGTTTTCTAAA
TTTTCTACAATTCAGACATTCTTGGATCCCCTAAAGAGTATTTGAAGTGA
ACATTTTTGTCTGGAACTAAAACCAAAATCTAAGAATTTGCGTTGTGGTC
TGGAAGTGCTCTCTGTGATTTTCTGTTGTGTTTCAACCTGATTGCTTGGC
AAATTCATGGGAGTGTCAGCCAACAGATTATAGCAATTGGTAACGGAGAA
CCTTTGCATCCTAGGGTTTTGATTCTTCAAATAGAACAGCCTGTAAAAAG
TTTTCTTCTAGGATTTCCTCTCTGATATGCACATTAAACTCTATGAAACT
GTAGGCTTAAAAACCCACAGTGGTNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNCCAC
AGTGGATACCTTCAAAGTGATTAAAAGAAGGTAACACAGGAAGCTAGTAT
TTTCTATTGCTGTTGTTTTTAATAATTATTTACCAAATGTTCTTTAATAT
AGGGCATCATAATCATTGACTCTGAGGGAAAGCTCAAGATACTGNNNNNN
NNNNNNNNNNNNNNNNNNNCCTTAGAGACTCCAAAGCTGTGATAAAGAGN
NNNNNNNNNNNNNNNNNNNNNNNNNNNNNNNNNNNNNNNNNNNNNNNNNN
NCCCGGCCCGCCTTTGTTCCTATTCATGGGTGCTCAGGCTCTCAGAATGA
GCACTCCTCTTTTGTTTTGTGTGTTCTGAGAATATTTAGATGGTGTACTG
ATGCCTTTTCAGGGCAACAGGGAAGGTGTCAGGGTGGCAAAGTGGAGGCT
GTGCTTTCAGCAGGACCTGTTACCCGTTTTATGTCATGTTTTCCTCCCAA
TTCACAAGGCATATTTTTGTTTGGTTTCCAGAAATAATCTTCAGTGGAGC
CCTGATCTTGGGGTGCACCAGAATGGGGGATTTCCAATGTTTCTGAGCTG
TTTCCCTTCTGGTGAACGAACCATCCTGGACGTGACAACCAGACCAATTT
TGGAAAGAGCTAGGGCCATTTGCTGGGCTGCCTAGTTTGGAACAGATTAA
TCTGCTCACCCCAGCAGTGGTCTTGCATTAAGTCAGAGTGCTACAAAGGC
TTTGAGGTCACTTCTTGAAAAGCTGTCAGCGTTTCCAGAGCCATTTAAGT
CTCTATTATGTCTTGGTAACTTCAGGTGTAGCTTGATGTGGTAGGACATT
AGGTGGTAGGTTCTCTGTGTATCACAATGGCATCTGGCATACAGGCATTC
TTACGAAATATTTCTTGTGTAGGTGAATTACTCTGAGGCAGTAAAGGTCA
CTTTGCAAATGTCTTAACAGTCTTGTAAACAGAGTGAAAAGCAGCAGCA
GCTGGCCTGTTTGGGAGTGTACTTTCCAGGTGTTCCTGCCCCATTTCTT
GGGCAGTATTATATTTACCCCCGAGCACTAGTTACTTCCCATGCTCGGCT
GACCCAAGGACAAACACAACGCTTTCTGGGCCTTCTCAGACAGGACACTG
CTTCTAGAGGCAGCTGTCACCTCCCGCGCCATCTCAGTACTGGGGTGCAA
ATCACATCTTCGGAATTACCAGCCAGAGCAAGAGAAAGCTTTCCACCAAT
CCAGTGCAAGTCTCTTTCTGTGTTAATTGACAGCCACCCTTGGCATGGAT
GAATGAATCCCAGCAACCAGCAGACTGAGTGCTGGAGTGCAGGCAGCTCA
TAACTGTCAGGCAAAAGAGCAAGAGGGTTTTAAGAGAGACTCCAGAAAGT
ATGGGATATATTAACCCTTGCACTGTCTTCTGGAATAGGAATGACATCTG
TTTGTATTAAAACAATTGTTCCGTTTAAGCACAGTTTGACAGCTCTGGAG
TGGGAGCTGGAGAGAGAACTTTGACTTCACTAGAACCTGTTGGCTAAGGT
TTTAGGGGCACAATATAGAAGGGTGTTGGATTCTAGAGAAGTGAAAGCAA
```

```
CCTTTTTGTACTCGTGTTGAAAACAGTGCCCTACTAGTATTAGAGTGTCT
CATTGATAGAGAGCCAATGACAACCAAGTCCCTACTCTCAGAGATGTTTT
AGAGTTACATTGCACGAATGCAAAGAAGCAACATAGGAACAGGTAATTAA
TAATAAAGTATAAACTGAGCAGATGTCTTGAAAGTATTCTAGGGTATGAA
AAGAATTCCTTCAGGATGCTGGTAGGCAGCAGGATCTCAAAGAATTAGTT
TTGAGATGAGGCAGAATGCTGGTAAACCACACGGGCAGTTACCTTGCTGT
GCCCCCTCATTTAGATGTGTGCCGAGCCCTGCAAGAACAGAAGCAGCTGT
TCCCCTTCCCACCATCATACTACAAGGTTAAGCCTAATCAGAATTTACTG
TATACCTCAAAAAAATTGTACAGCAGCTACCACACACGAGCACANNNNNN
NNNNNNNNNNNNNNNNNNNNNNNNNNNNNNNNNNNNNNNNNNNNNNNNNN
NNGTTCTTGTTGCTGTTGCTGTGTGATGCTGTCAGAGGCTTATGCCCTGA
GGGAGGGATCAAGGGAGTGGCTGAGGGTGGTCACAGAAGACAGATTCCGG
GGCATGTGGCCCGTACGAGGATGCCAAAATGCCACAGTCACACTCACCTC
AGAAGGGTGGGATTGGTGGGGGCAGAGAGGGGCGTTGAAATGTTTTGAAA
ATTATCTTCAAGAGTATGTGAAAAAATTGAGAATCTTGATCATTCTATCT
GAACATTTTCTTAGGAGGATTCTCCTTTTCTCTTTACATTCTTGATCAGC
TCTTGGGTAAAGACATGGCAGAGATAAGAGCGTGAGTACCAGTTCCTGGG
GTCAGCAGGCTCTGATCCTGCATGCAATAGAGAGCTCCAGTGTATTGGGA
AGGCTCCCAACTCGTTAGGAGAGTTGAGACATCGTATCTCTTGGGTGACA
GAATAAATTTTTCATGTCTATTAATTGGCCTAGGTTGACTTTAATGACAT
ATACTTTTCAAATGTGGGGCTGATGGAGACCTAAGCAGACAGATCTGTGG
GCCACCCCTTAGCCCTTTGCCGCTCTCCCAGGGCTCAGGATTCTGACCAC
AGCCTAGTCACCTGTCGCACACTGCTGTTTTTCAG (SEQ ID NO.: 2)
```

MGB-CEGP1 int 3.1

FIG. 1B CONT.

```
>CEGP1 intron 5, 2556 bases
GTAAGTATGGGCCAGTGCACACCTGCCATGGGAACCGTCGTATTCCACAG
GCTGCCTTCTGTGGCCCAGCTCAGAAGCACCACCTCATGGCACGGCTGCA
GCAGCAGGGAAGGCAGTTAGCACGGGATACCGACCTCTACCAAGTACTTG
TTCACTGCAGAAGGGTGGTCTCCCTTAGGGAAGGGAAATGATATTTTAAA
AAGGAACTCATCAGGAGGAAATGAAATTCAGGAGTAAGGAGTGTGAATGT
TGGGGGGCAGTTCTCCCTGTTCCCACAGAATAAAACCAAATGTCCTCATC
TGGCAATCACAGCTCTTTGCCACCAGGTCCTGCTTCCCCTATAAACCTCA
TCTGCCTCCTTTCCGCAGACACTACTCCCCTTGCCTTTGGAGAACAGCCC
AAATCCTTTGATGCCTCCAGGCCTTTCCCAAGCCCTCCTGCCTTCCTGGC
GTGGTGGACTCTCACTCAACCTTCAATATTCTGTTTAACTTCTAATAAGG
ATAAGCNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNCCATCCT
CTGCTATCAGAAGCCTCCTGGGTGCTTCAGACAGGGCAGCCATCTTGTAC
TTTGGCTCCCACAGCACTTTCCTCAGCTGTATAGCTCTGGGTTGACTTGT
GTGTTGATGTGTCTGTCTCCCAGGTATGAGCCCCTCCAAGTCAGGGAC
CTTGCCTCATTTTTCCTCTCAGTCCTCCCCTGGTACCTGCTATGGGATAT
GCTCAGTACACTTGTGTTTAATGAGTGGGTAAATGGGTGGCCTACACCAT
CGGGCCGCAGCTCCTGCACCACGATTGTAGTAACAAAACTCCACCTGGGA
ACAGGAAACCACTGGCAATTCATGGTGTTCCTAAACCACGATTTATGCCA
GGGGAAGCACTGAGGAGTTCCCTTTAGGAACCTTCCCAAAGCCATGGACA
GAAGACCCCTGCCATTTGGTGGGGATGGTGGTTTATGGTGAGTAGGAGAT
GAGGGGACAGTTTCACTGGTGAGGGACTTCTCTCCATTGTCTCCCTCACA
AAGCAGACTGCCACCCCAAAGCTGTCCAAGCCAAGGCTGGTGCCACCATC
ACACTCAAGCAACAGGTTCTGACATGCTCTTAGGGCCCCTCGAAGTCAGG
CTGTCCCTGAGGGCTTCCAGTGAGCTAGCAGAGTGGAGACCATTTTCCCA
CCTCCAGATCTTCGGAAGGAAGACCCAGACCCTCCAAGACTCACCTGCGG
GGCGAGACCCTCAACATTTCATAGTCTTTCAGGGAACAGTTGCTGAAGGG
GGCGGGGGGGTGGGCACCTGTAAGCTTGTTTTTAAAGATTTTAAATGTCT
```

MGB-CEGP1 int 4.1

FIG. 1C

TTAAGATATCACTGCTCAAATAATATTGTTCTGNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNCGTTGAGGAATTAACAAAGAA
AAAAACTAAGACCTAGAATCTCACCACATAACCAGCTGTTTCAATTTTTC
CATATTCCTATTTAGTTGTTGTTCATATGCATACACAATTTTTACATAGC
TATAATCACAGGACAACACAAATATGTAATTAGTTCTTTTGAATTAGAAA
AATTACAAAGGGCCTATGTAAAATGCAAACACTCCAAAGCATATAAAGAA
AACATGCAGTTTCCCGCCTCCCGTTTCCCTTGCCAGAGGTAACCACGGTT
AGCAGTTTGATGAATAGATAGTTTTGTAGTTGGCTTTTTTTCTTTTTGGC
CTATCATCAATACATTCATATATAGTCTTGATAATTACCAGTTACTGTCA
CGTTAATTGTGTGCAGAATCATCCTGTGATTATCCTTCCTTCTAACTAAT
CTAGATTGAATCTGATGAGAGAAATTCTGACATATATGTACAAATTAAAT
ATTGTCTGTTTTATTCCAGCATAAAGTGCTATAGCATTTCCCAAAGCCCC
AGTACAGCTGTATTAATAGGTAAACTTCTCTAGATAGAACAAAGCAGTAG
TCTAGAATCTCTTGGTATAATTTCCCTTATATAATAAAAGTCTCTCCCCC
AACTCTCCCATCTCCCTCTTCCTGTATGACTTTGTTTAAACCCATGTTTC
AGCATTTCTACAATTTGTATTGTAACTATCTGCATACACAGACACCACAG
GGTCTGACTTGGAGTTATGTCTTTCGTNNNNNNNNNNNNNNNNNNNNNNN
NNNNNNNNNNNNNNNNNNNNNNNNNNNNAATCAGAATTTCTCTGGAGCAAACAC
AGCCCTGTGTTTGTGGAAATCTCAGTGCTTTATGTATTGATTCATTTTGC
TGTCAG (SEQ ID NO.: 3)

FIG. 1C CONT.

>CEGP1 intron 6, 716 bases
GTGAGTGGCAACCCCAACACTGAGTGAGGGTCTGCACCAGCCTGCCTGTC
CCTACCCCTACCCCTTAATGGTGTTTAGCACAGATGCAGGCTGTTTCCTG
TGCATTTGCCCCCCCAGCAGGCCCTGTGCTGCTTCGCATGCTACAGTGGG
AGTGGTCTAGGCCTGTGGGGAAGGCCCCTCTCTCCCTGTGTGACCTTGGG
AAGCCCTTCCTCCTCTCCTGGACTAGGCTGCTCCTAACGCTGGTATTCCA
GAGACTGGCACAACACCTCCCAGGAGGCCAGGGCAGCACGAAGTTAGAGC
TGTTTATAATGATGCGGCACTTCTGGCCAGCAGGAGCCAGGGCCGTATAT
TTCTGGCGGGATGCCTGCCTTGCCCTTCACGGTGTGTCCTTCACTAGCTC
CATTTTAGAGGTTTCCAGGCCCAAGGCTCTTTTTCTCCTCGACTCAGGGG
ACTGAAGCTTGCATTCCCTAGTGTCTCTTTGGTCAGTGCAATATACCTCC
AAAATCTTTTCCATGTTTAATGTTTGCTAAGGATCTGTGGCCCTTTAACG
GGCTGTGTCTCCCACAGAGCCTCATTACAACACATTTTTATTGCGTGAAC
AGAGTCACATATCTTTCATTCCTCTTATGTCTGGGATTTCAGCAAACACA
GTTGTATGGGGATGAGCAATCTAACTCATTCAGTCTGAGAACCGTGCTCT
TTTGCTTCTCTTGTAG (SEQ ID NO.: 4)

CEGP1 int 5.1

FIG. 1D

>FOXM1 intron 3, 2041 bases
GTAATGTGTCCCACAGCAACCAAAATCAAGGTCAGCCCAGCCTGACAGTC
TCTCCAGTGCTGTACTGCAACTTGTATCTGGACAGCAGTTAAGTGCAAA
GGACACTAGAATGATAAACAAATGTATCTTTTAGATTGTGACTCAATCTT
ATTGAATCCAGGCAAAATCATTAAGAAGAGCTCCTTAACTACTTCATGTG
TTACTACCTAAAGTCCATGGAGGGTCTTCAATGTAGCACTCAAGCCCACT
TTTCTGCTACACTCAACAGCCGTCCTAGATGCCAGCAGCTAGAGTGGCTA
AGTAGTTTTATGAAAATGTCTTGATTAAAAAAAAAAATGCTGTCTGTGAG
CCTCATGACCCAAGATGTCATCTCCTGTAGCGTCACATAGCATTTCTAGT
GGGCAGGGGTTTTCCTTTCACTTCATTCATGGAAAGACCGAGATGCCTGT
GAGTCAACATAGCTCACGCAGTTGGTCGGTGTCAGAGCCACAAATGAGGT
CTTCTGACGGGTGCTCAATTCCAAGTCAAGTGTGCTTTGTTTTCCTCATG
GTAGAACTCNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN FOXM1 int 3.2

```
NNNNNNNNNNNNNNNNNNNNNNNNNNNNNNNNNNNNNNNNNNNNNNNNNN      FIG. 1E
NNNNNNNNNNNNNNNNNNNNNNNNNNNNNNNNNNNNNNNNNNNNNNNNNN
NNNNNNNNNNNNNNNNNNNNNNCCTCATGGTAGAACTATGNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNCATGGTAGAACTTTTAATTTTACTCCCTTCCATCAGCTTACTTTCCTA
GNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNTTAATTTCCTAGNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNTAATTCCC
TAGTTTCTTAATTTCTCTGAGCCACCTTTCTTGCTATTGATCACTACCTC
ACAGCCTTACTCTGCTTTTCTAGCCCCTGACAGCTATCTAGGTCTTTTCT
TTATCACAATCTAAGGTTGGCATCAGTCTTTATTCCCGTAG*AATAGATGG*    ┌──────────────────────┐
*GTTTATGGCTGAAGGTGAC***GGCTCTGCGGTGTGGAGTGTCAGGAGAGTTG**  │ MGB-FOXM1 int 3.2    │
CCAAGAGGGCTGCAAAGACACCAGACGAAGCCTGTGCTGAGCACAGTGGG    │ (underlined)         │
AGGGGCCTGAGGCTGGTTTCCCCATGTGTTTGAAGGGTGATGTTTCTGAA      │ FOXM1 int 3.1 (bold) │
TCTAAAGTAGCTGATAACCAGTTGTCTTGCTCTTCTTCCAG (SEQ ID NO.: 5) └──────────────────────┘

>FOXM1 intron 4, 993 bases
GTGAATGCCCTGCTTTCCTCTAAATAGGGCCTAAGTTGGAGGTTGTCATA      ┌──────────────────────────┐
G*CCATCTCAAAAGGAAACAAGTTCTGCTAGTGATGCTTTCATTTGATCAG*    │ FOXM1 int 4.1 (underlined)│
*GGGAGAGTTAGAAGCCAGCCACCC***AATTAGTGACTTGCACAAAACCCAGT** │ FOXM1 int 4.2 (bold)     │
GAATTAAGTACACTTGACAAATACCAAATGACACATTTTTGTGCCAGACC   └──────────────────────────┘
AGAGCAAGGAGAAGGCTGTTCTGACCCAACAGAAAGGGCTCCCCAGGGNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNTAC
AAGAAATTCTGGGAATGCTTGCTCTAAAAAAAGCCCTTCCTNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN      FIG. 1F
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNG
CCTGCCTTAGGCTGGAGACCAGAAGCTGAGCTACCAGAACGTCTTTTCAG
AAAGAAGTTATTTTGGTTTTTCAGAGTGCCCATAAGGCTGCTGGTAGCTG
TAACCATTCTCCTGGGAGGGGCAGTTGTCTGGGGTGTCTTTTGTCATCAG
TCAGGAATAAGTGTTTTTCCCAATCCGGTCAAATTGACCACGTTGGTGGT
AACTTCATCTCATTTCTCTCCCACAATGCCTGGCCGCCACCAG (SEQ ID NO.: 6)

>FOXM1 intron 5, 602 bases
GTAAGGTTCTTTCCCTCTGGCTCGGGGCTTGGCCTTGTTTTCCTTTCACT      ┌──────────────────────┐
GCTCAGCATGGCTTTAG*TGGACAGAGACAAGATGTGATGTGGGGAAGGGT*    │ MGB-FOXM1 int 5.1    │
*CCCTATGGCCATGTTTTGTCTAGGTGCCAGCCCTAGACACAGAACACCCT*    └──────────────────────┘
GAGGGTCAGGCACACACCCACTTCCCTCCCCTTCCATGGGCATCACAAGG
GCACACTGAGCAGAGCAGGGCACAGCAGGGGAGCATGCTGCAGCAGCCAC
```

AAGCGCATGGCACCAGCCTCAGGGGCGGCAGTTCGTTCGCTCACTTTTGT
GCCTAGCTTTTCTTTGCCACGCATATAGCTACCTGCTCTGGCATCCCCCA
GGGGTGTTGAGGACACGTGGGTGAAGCGGTAGTGCCACTCTGCCATCATG
TGTCTGTAGGCCACCCACCTGCCCACTCATCACAGTTTTGGAGACTGCTC
GCCTACGTCCATCCCCTCAGGTTGGCCTCCTCTCTCTGGGCTGTCATTAA
CTCAAGCACACACCACCAGAGCAGCTGGTGGGGTTTTGCCATCCCCTCTT
TACCTTATTGTGTTAACATAGGTTTCTTTCTCTCCCATCTGCCACAAGC
AG (SEQ ID NO.: 7)

FIG. 1G

>FOXM1 intron 7, 4656 bases
GTGGGTGTCCTATTTTCCTCTGAAGAGAGATTCTGGCCAATTAAGAATGT
TGGACCTTCAGCTTGCAAAGCACTCTGATAAGTGTTCCTTGAGAGCTTAT
AAATCTAGTTGGGTAGAAAAGGCATAAAAACATAGGGAAGTGTAATAGCA
TTAGAAGAGCTAAAAAGGTATTTGGATTACAATGTAAGTGGTGTCAGAAG
GCCCATAAATACCTGATGAGCTTGTAAGAATTCAGACAAAAGTGATTGTG
ATAGATGGGCTAGGATTATTAAGGAAGATACACAAGGGAGGCAGGCCTTA
GAAAGAGATGGATTTNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNGTGGATTTGANNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNGTAGATTTGGGTAAGCAAAC
AGGTGTAGAGAGAGCATGCTAATGGGCAGTGCCATGGAGGCGGGAAATGC
AGTTCGTACCTGGCAGTAGTAAAGTGACTGGGTCAGACTAACTNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNGTCTAGCTTGAGGGGAAGGTGAGAAGGGTAAATTCAGAGCC
AACTTGGATCAGCCATCAGATCTGCACTTAACACTGTTAAAGGGTTCTGT
GAGTACGGGCTGACATGTAACCAAAGTGAAAAGCTTCCCCCATCCCCTTC
AGAGAGATGAAAATAGCATAGAGTCTGGAGTTTAGAGCGACTTGGGTTTG
CNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNCATATTACACACAAAATTATACCACACATACATAATTTAGCGTAAATT
CATTCATGTGGCCGTAGCATGTGCCCTGTTTGGGTTTTCATGCAGTGGGT
TTTCTCCCCTTTCCTTTTTGGCTCCCTCTCCACCCTACCATCACCCACAT
CACCCCTACTCCCAAGATAACTGGTTGATAATTTATGATGCTTTCTTGCA
TATTTTATCAATGCTCTTAGTTATACTATACATGTATAGCGATAGCCATT
TTATATGTACACATACAACACACAGAACATTGATNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN MGB-FOXM1 int 7.1

FIG. 1H

MGB-FOXM1 int 7.2

```
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNGTTATCAATTTGTGAGAGCTCNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNTGTGAGAGNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNCCCTGTGAGAGCTCTTTGTTGT
TAAAATAATCTTCTTTCTTTTATGCTGAAGATATTTTTCTACTTCTATTG
TTTATCTCTTTACNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNTGTTTGTTGTTTCTTAACT
TTGTTTATGGTATCTCTTGCCACAGTAAAATTTTAAAGTTTTATGTAGTC
AAATGTCTCTCTTCTCTTTTACAGTTTCTGGGTTTCCAGTCTTGGTTAAG
AAGGTCACCCGCACCCTCAGATTGTATATGTAGTCTCCTAGATTCTCTTT
CAGGATTTGTATGATTTTAAGGTTTTCATTTTTTTTTANNNNNNNNNNN
NNNNNNNNNNNNNNNNNNNNNNNNNNNNNNNNNNNNNNNNNNNNNNNNN
NNNNNNNNNNNNNNNNNNNNNTAAGGTTCTTATTTTCATGCATTAAATCT
TTGTATACAGTGTAAGACAAGCATGCAATTTTATTTCCTCTCGGATGAAT
CCTATTATAATTATGCCACTACATACTACATACCCGCATCTTTTACCCCC
AGAATTGAACTACCAACTTCAACATACATCGTATTCTCATATTTAATAGA
TTTTAAGACTTCAAAACGACACAAAGAGGATCAGAACCCGTATGTGATAT
TTTTGTGCGTCCTGTCTGGTGACCGTTGGTTCACCTTATCTCTGTTTCCC
TTTCAG (SEQ ID NO.: 8)
```

FIG. 1H CONT.

MGB-FOXM1 int 7.3

```
>PRAME intron 2, 614 bases
GTAAGTTCGAGCCCTGATTCCTCCGCTTCCCCGCAGGGTGACCTTGGGCT
TGTGCCCCCGGCACCACCCCTGTCCCGGGTCCCTGTTTTCTCTCTGGAAA
TGGGTTGAAGACCAAAGAAAATAATGTGCGCCACTTGGGTCACCCCGGGC
CGCCTGCCCCGGAAAATTGGCCCCAGTTGAGGAGTTGTGGCTGTAAGGAT
GCCTTGAACCGAGGCGGCGGTGCTCGTGGTTGGAGCTCTCCAGGGTGGGT
GCGCATTTGTAATGCGGTGGATGCTCTGGGACTCGGCCCCTCTGAAGGTG
```

MGB-PRAME int 2.1

CTGGGGGTTGGGGACGGCCCAGGCAGTGGCGTAGGCGTCCTAGGAAGGCG
GGAGCAGAGGCAGAAATGTCGCTGCAAGACCGTAGTCAGGGTCCTTGACC
ACAGGGGTCACTTGTGACCAACCACATGGTCTGTTGTTCCTCCTGCCCCC  FIG. 1I
TGGTTCAGCCCAGGAAACACTGGTGCTCAGGTTTGGAGCCAGAGATTTGC
ACTGAAAGGGCGGGATTGAGTCGCCAGTTGTCAGTTTCCTCAGCAGTATT
TGCGGAGGTTTTCACAGGAGGCCGTTGCTTCGTAAATATTATACATGTAT
TCTTCTTTTTGGAG (SEQ ID NO.: 9)

>PRAME intron 4, 432 bases
GTA*AGGGTGACCTAGCAGCTTGGTGTGGGGCCCTGGGAACCTGAGCAGGA*
*TGCAGCTGGGGTCAGGGAGCATGGAGCGCCTAAGGCTGGGCCAGAGGCTC*     MGB-PRAME int 4.1
TGATGGTTGCCAGCAAGGAAGTTCAGGGAGGCCTTGGGGCTACTGCAGGG
GTCACTCTTGGAATGGGCTTCTGGACATGGGGCACTGATTAAAATGCAGA
GGTGTCTGAAGGAACATGCACCTGCTTCCTCCTGGTGGGGTGGGAATTGG
GGACCAGGAAGGATCCCAGGATCCTAGTGGGAAGGGAGCAGCTGATGCC
TGAAGTACGAAGTAAAAGTGCAGATCTAAGGTGGATGTCTGTTTGGTTCT    FIG. 1J
TACCTACATTATGAGACTCATGGTCTTATTTTGAGTTGATCTTAAAGCAT
CATCTCAGCTAATTACCTGTTTTTCCCCACAG (SEQ ID NO.: 10)

>STK15 intron 1, 3740 bases
GTACAAGGGGTTTGTTGAGTGGTGTTGACATGCGCGGGAGGGGTGGGTGG
GCTTCAGATTGGATTTTGTCCTCCGAGATCACCNNNNNNNNNNNNNNNNN     FIG. 1K
NNNNNNNNNNNNNNNNNNNNNNNNNNNNNNNNNNNNNNNNNNNNNNNNNN
NGGTAAGCGTACGGAGAACTTGCAGCTGGGGTGGGTGTTACAGAGGAAAA
GCAGGAGTGCGGTTTAACGGGGGCCGCTTTAGATAGAATAGCCTAAGAAG
GCCCTTGTCCTGGCTGGATGAGTGGGTGAATTGATGAATGAGAACCTCCT
TGCAGAGGCCTTCCCGGTCCNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNGGGATGCAG
ACCGGTGCATACAAATCGTCTGGGGACGTTAAAATGNNNNNNNNNNNNNN
NNNNNNNNNNNNNNNNNNNNNNNNNNNNNNNNNNNNNNNNNNNNNNNNNN
NNNNNNNNNNNNNNNNCACTGTCCTTAACTCT*CGTAATGTCTCTTCCTCTT*     MGB-STK15 int 1.1
*CCGTAACCTTCCTTGTCCCTTGAATTAAACGTTTTTCAGCAACCTACTCA*
GTTCGTCCTTCCCTTCATCTCTGCAGACATGCACAGGTCTGAGGGAGGAA
GGAATAAACCGTATAAACCTCCTGCGCTATTAGCCTAACAGCTTTTCTAT
TCAAAATAGTAGGACTTCTGGTTTGAACTGAATGGATCCTGTGAAAGTCA
TCNNNNNNNNNNNNNNNNNNNNNNNNNNNNNNNNNNNNNNNNAGTCTC
CTTGGCGTTGTCTCCAGAATTCTGGATTAGAATCTTATTCCATTCTGCTT
GTTATTCAATTTCCCTAGAAAGAAAGGTAGAATAAATTGGAGCAAATGCC
TGTAGCTTCTGTCAGAAGAATGTTGAATAAATGTTGTTAGGCCTATGTGA
TCTCATTAGACTGCTACTTAGAATTGTAAGGGAAGTAAAGCATTAGAGCA
TGTGTGAAATTAAATATTTGATTAACACAAGTGTGCATTTCCTTGTTGCT
GTTTATCAACTTTTACTTACCCACTGTTTTTTATAAGGGCTGCAGCCTG
TAGTCTGGGCCTGGCTTCATCATGGAATTATTTGCTTAATTGTAAAATGG
TAATCTTAANNNNNNNNNNNNNNNNNNNNNNNNNNNNNNNNNNNNNNNN
NNNNNNNNNGGATATTTGATAAGAAACTTCAGTGAANNNNNNNNNNNNNN
NNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN

```
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNGGGANNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNN
NNNNNNNNNNNNNNNNNNNGCAGGGAAAGCACATGCCTGTCCCTCCCTCATT
AGCTTCATTTGGACAAAACATGTAAAATCCGGTGTGTTGTGGAGGCCTTT
TGATTGGGGAACTGTAACGCTGCCTATCGAGCAACAGCACTTTAAGCAGG
TGGCTTTGTTCAAATTAAAGGTTCTTCTTTTTCTTTTCAG (SEQ ID NO.: 11)
```

FIG. 1K CONT.

```
>STK15 intron 2, 1622 bases
CTAAATTGAATAATCTGTAATCTCATTCACATTTATAAACCCACATGGAG
GTTGGTCTTGTCGGGAATTCTTTTCCGCCTTTACTTTGGATTTAAATTTAG
ATCCCTTACTGTGATCCTGGATATGAATTAGTCACTTTTCTCGTGTTCAG
TAACATTTTGCTGCTTCTTAGAGTAGCTTTTTTGTTCTGCTTTGTCTTAT
AATCGGCTGCTTAAGTTTCTATATCCCTCCACTGTATGCAGGATAATAGT
AATAATGCATCTGGCAGGAGTTCAAAACTTTTAAAATTGGCCATAAATAT
AAAATAATTAGAAAAAGGCTACCTTGAATTACTGTATTTGATTCTAAGTT
CCTATGATAACGGCCATTTAAAAAATTGCTCTATATTTAAAATGTTTCTT
TTTATTTGTCTTTGTCTGAATGCCTGCTGCGTTGTGGACAGTGTGCTAAT
TTCAGGAGTAACTGACTTTGTATTTGGAAGTCTTAACACCCTCTCTTTGT
AGAGCACTCATACCGTTGAGCTGGGGATGGACTTTGAGGCTTTCATTTCT
AGCACTTGTCCCTCACTTACAATGAGCTGTTGAAGCTGAAGGAAATCTCA
TCCCTCCTACCCCTTTTAGTTTGATTAGCTGAGGGTGTTAGAGTTAACTT
AACAATTTAAGGTTGTAATACAGTACTTACAGGCGTATAAATAATACATT
```

MGB-STK15 int 2.1

FIG. 1L

```
TCAANNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNTAATAATAATA
ATACATTTTAGTAGTAACTTTGTGAAGTGTCTACATTTGTTTCCTCTTTG
TCAGTTTTTTGCTCAATTCCATTTTGTCAATACTTGGAAAATGAAACATT
GGTTAATCAATAGTACAGTAATAAGCTTATTGTGGAAAATCTTCGATATA
TGAAAACTTAGACTCTTCTAAAACTTCATGAAGATAATACCACTGTTGAA
CGTTTTGACGTATTTTTTTTGGTCTTTTTCTTAAACGTATATTATCAAA
GAAATTTCAATGGAACTGAGATTTTGGCATAAAGTTTTTGTATCATAGCT
TTTTGCCAAATAGCAATGTAGTGTCTATTTCCAAATTATTGAGAAATTTT
AGAAAGTGTCTCCTTCATTAATGGATATTTGTTAATAAAGCATGATTTTT
AGGGGTGAGGAATTGGAGGGGATAGAAGGTATCATTCAGGTATTCTTAGC
CACATACTAACTATCCTCTGGAGGTACTGATTAAAATACCTTTTCACCTT
CCATCTCTTATCAGTGACATTCATTATTTTGCTATACTAGAGAACAAACT
TTGTGAAATTCTCAATATATTCATCTTTTGCTTTCATGAATGCCAGAAAG
TTTATTTTCTCTTCCATTCTAG
(SEQ ID NO.: 12)
```

FIG. 1L CONT.

```
>STK15 intron 4, 1093 bases
GTAAGCTTTCTTATTTACAAAGTTCTGTACTGTTCTACTAGAATATATTA
TTTCGTTGCAAATTTCGTTGTGGGAACTCTGGGGAAAAAAATGAGGCCTT
TATTTGCATTTAGAGGATATAAATGTTTCCAGATTTCCAATCTTAAAAAA
AATGGAATTTTGTGTAATGAGGTATTTTACTAGGAACTCAAGTGCTTTAA
AAAATGGCTTTCAAATTTAGAAAAAGCTTGTATGAATCTTTTATAGAAAT
GTGTGGAAGTTCCTCTCTGTCCTTAGAAATAACCACTACATATGGTTTAT
GCGTCTGTACTTTTTTATTGTACAAAAGTGCAAGTTTTTAAAAAATAGAA
TATGTTGCAGAACTATATACTCATATATGACTGAGGGTTTTGACAGTATT
ATAGTTTTAGTTCTTTATTGTAAAGGTTGGCTGTAATGTCTTCCCCAGGG
CTTTTCTAAAAGCCTCCTCTCAGTCTCTGAACTATCTGGACTCTAGAATG
TACCGGGAGGAGCGAGGAATGAACCCACAGACTCTTTTGCTTTTAGCGGT
CTAACAGAGGCTAAGAGTCTAAATCCACTGGTTCTCATGCCCCAGCTAGC
CTGTGGGCTCCATCCCGCTTCCATTAGTAACAGTGGCTCTGTCTCCACCA
CCAGAGTGGTTCTCCACCCAGAGAGAATTAGCACCTCTGGGACTGGAGGG
AGCAGCTGGGGTTAGTTTGAAACATGCCCCCAGATGGTCTGGAAGCATTC
CTCCCTCTCTGGTCACTTATCCTTTTTGTGGTCTTCAGCGTTGTCATGGC
CCTGTTCCTCTGAGCATAGTACGGGCTTGGGACATTTCCCATAGAGTGCT
TCAGGTCTAAAACCCGAGACTGCTCCTTGTCACTGACTCTCACACCTGAC
GGCAGCTAGGGACGTCAGGGTTTCATGTCGTGGCAGCTCTTTGATAGTGG
TTATTGCCTTGGTTCTTGCTGAGGATGCATATTGAGTGAAGTTGGAATAC
CAAATTATTTGTACAATCTGTCTGCTACTCATTGAAAATTTGTTAGAAAA
GCTTTGTTTTCTTCACATTCTAAAGTGTTCAAATTCCTCCTAG
(SEQ ID NO.: 13)
```

FIG. 1M

[MGB-STK15 int 4.1]

Figure 2

| Name | Sequence | SEQ ID NO: |
|---|---|---|
| MGB-CEGP1 int 1.F1 | AGCGCCTGTTCCGATCTG | 14 |
| MGB-CEGP1 int 1.R1 | AACCAAAGTTCTCTGCTGAAAACC | 15 |
| MGB-CEGP1 int 1.P1 | CCCTGAAGCAGCAAC | 16 |
| MGB-CEGP1 int 3.F1 | CTGTTGCTGTGTGATGCTGTCA | 17 |
| MGB-CEGP1 int 3.R1 | CCTCAGCCACTCCCTTGATC | 18 |
| MGB-CEGP1 int 3.P1 | TCAGGGCATAAGCCT | 19 |
| MGB-CEGP1 int 4.F1 | TCCCCTTGCCTTTGGAGAA | 20 |
| MGB-CEGP1 int 4.R1 | AAAGGCCTGGAGGCATCAA | 21 |
| MGB-CEGP1 int 4.P1 | CAGCCCAAATCCT | 22 |
| MGB-CEGP1 int 5.F1 | CTTAATGGTGTTTAGCACAGATGCA | 23 |
| MGB-CEGP1 int 5.R1 | CCACTGTAGCATGCGAAGCA | 24 |
| MGB-CEGP1 int 5.P1 | CAAATGCACAGGAAAC | 25 |
| FOXM1 int 3.F1 | GCTCTGCGGTGTGGAGTGT | 26 |
| FOXM1 int 3.R1 | CACAGGCTTCGTCTGGTGTCT | 27 |
| FOXM1 int 3.P1 | TGCAGCCCTCTTGGCAACTCTCCT | 28 |
| FOXM1 int 3.F2 | AAAATGCTGTCTGTGAGCCTCAT | 29 |
| FOXM1 int 3.R2 | AACCCCTGCCCACTAGAAATG | 30 |
| FOXM1 int 3.P2 | ACCCAAGATGTCATCTCCTGTAGCGTCACA | 31 |
| MGB-FOXM1 int 3.F2 | AATAGATGGGTTTATGGCTGAAGGT | 32 |
| MGB-FOXM1 int 3.R2 | CTCTTGGCAACTCTCCTGACACT | 33 |
| MGB-FOXM1 int 3.P2 | CCGCAGAGCCGTC | 34 |
| FOXM1 int 4.F1 | CCATCTCAAAAGGAAACAAGTTCTG | 35 |
| FOXM1 int 4.R1 | GGGTGGCTGGCTTCTAACTCT | 36 |
| FOXM1 int 4.P1 | CCCTGATCAAATGAAAGCATCACT | 37 |
| FOXM1 int 4.F2 | AGAAGCCAGCCACCCAATTA | 38 |
| FOXM1 int 4.R2 | TGTGTCATTTGGTATTTGTCAAGTGT | 39 |
| FOXM1 int 4.P2 | TGACTTGCACAAAACCCAGTGAATTA | 40 |
| MGB-FOXM1 int 5.F1 | TGGACAGAGACAAGATGTGATGTG | 41 |
| MGB-FOXM1 int 5.R1 | GCTGGCACCTAGACAAAACATG | 42 |
| MGB-FOXM1 int 5.P1 | CCATAGGGACCCTTC | 43 |
| MGB-FOXM1 int 7.F1 | GGTGTCCTATTTTCCTCTGAAGAGA | 44 |
| MGB-FOXM1 int 7.R1 | TGCAAGCTGAAGGTCCAACAT | 45 |
| MGB-FOXM1 int 7.P1 | TTCTGGCCAATTAAG | 46 |
| MGB-FOXM1 int 7.F2 | TCATTCATGTGGCCGTAGCAT | 47 |
| MGB-FOXM1 int 7.R2 | GGTGGAGAGGGAGCCAAAA | 48 |
| MGB-FOXM1 int 7.P2 | CCTGTTTGGGTTTTCA | 49 |
| MGB-FOXM1 int 7.F3 | AGAGGATCAGAACCCGTATGTGA | 50 |
| MGB-FOXM1 int 7.R3 | GGGAAACAGAGATAAGGTGAACCA | 51 |
| MGB-FOXM1 int 7.P3 | TGTGCGTCCTGTCTG | 52 |
| MGB-PRAME int 2.F1 | GGGTGACCTTGGGCTTGTG | 53 |
| MGB-PRAME int 2.R1 | CTTCAACCCATTTCCAGAGAGAA | 54 |
| MGB-PRAME int 2.P1 | CCCGGGTCCCTGTT | 55 |
| MGB-PRAME int 4.F1 | AGGGTGACCTAGCAGCTTGG | 56 |
| MGB-PRAME int 4.R1 | GCCTCTGGCCCAGCCTTA | 57 |
| MGB-PRAME int 4.P1 | TCCCTGACCCCAGCTG | 58 |
| MGB-STK15 int 1.F1 | CGTAATGTCTCTTCCTCTTCCGTAA | 59 |
| MGB-STK15 int 1.R1 | ACGAACTGAGTAGGTTGCTGAAAA | 60 |
| MGB-STK15 int 1.P1 | TCAAGGGACAAGGAAG | 61 |
| MGB-STK15 int 2.F1 | CATTCACATTTATAAACCCACATGGA | 62 |
| MGB-STK15 int 2.R1 | AATCCAAAGTAAAGGCGGAAAGA | 63 |
| MGB-STK15 int 2.P1 | TGGTCTTGTCGGGAAT | 64 |
| MGB-STK15 int 4.F1 | GCGAGGAATGAACCCACAGA | 65 |
| MGB-STK15 int 4.R1 | GCATGAGAACCAGTGGATTTAGACT | 66 |
| MGB-STK15 int 4.P1 | CGCTAAAAGCAAAAGA | 67 |

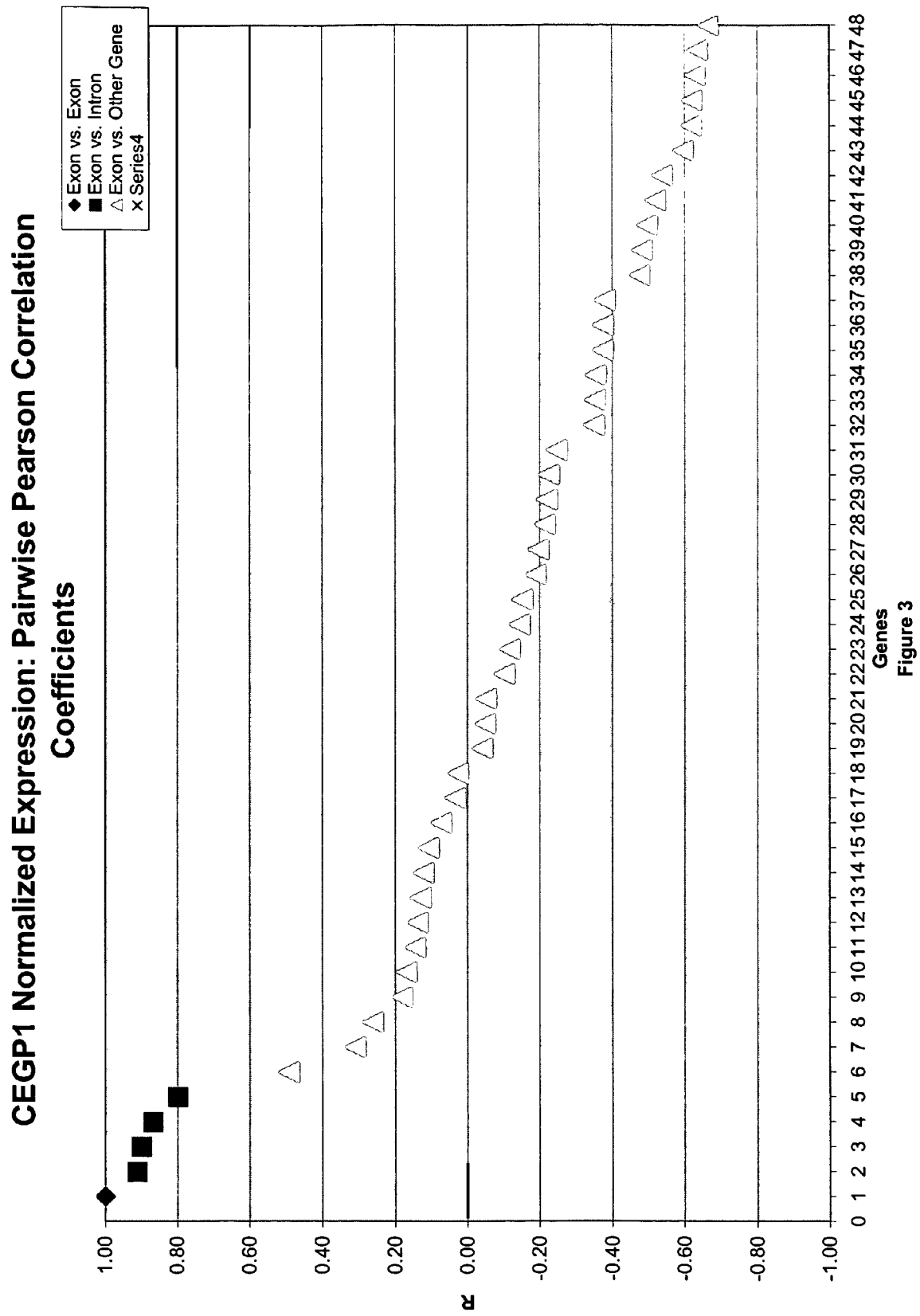

Figure 6

| Gene Name | Sequence ID | Sequence Source | GHIallgenes2-03.txt Accession Number |
|---|---|---|---|
| 18srRNA | M10098 | NCBI | M10098 |
| 28srRNA | M11167 | NCBI | M11167 |
| A-Catenin | NM_001903 | NCBI | NM_001903 |
| ABCB1 | NM_000927 | NCBI | NM_000927 |
| ACTG2 | NM_001615 | NCBI | NM_001615 |
| AD024 | NM_020675 | NCBI | NM_020675 |
| AIB1 | NM_006534 | NCBI | NM_006534 |
| AK055699 | AK055699 | NCBI | AK055699 |
| AKAP-2 | NM_007203 | NCBI | NM_007203 |
| AKAP12 | NM_005100 | NCBI | NM_005100 |
| AKT1 | NM_005163 | NCBI | NM_005163 |
| AKT2 | NM_001626 | NCBI | NM_001626 |
| AKT3 | NM_005465 | NCBI | NM_005465 |
| ALDH10 | U75289 | NCBI | U75289 |
| ALDH12 | AK074266 | NCBI | AK074266 |
| ALDH1A1 | NM_000689 | NCBI | NM_000689 |
| ALDH1A3 | NM_000693 | NCBI | NM_000693 |
| ALDH2 | NM_000690 | NCBI | NM_000690 |
| ALDH3 | BC004370 | NCBI | BC004370 |
| ALDH3A1 | NM_000691 | NCBI | NM_000691 |
| ALDH3B1 | NM_000694 | NCBI | NM_000694 |
| ALDH3B2 | NM_000695 | NCBI | NM_000695 |
| ALDH4 | NM_003748 | NCBI | NM_003748 |
| ALDH5 | NM_000692 | NCBI | NM_000692 |
| ALDH7 | U10868 | NCBI | U10868 |
| ALDH8A1 | NM_022568 | NCBI | NM_022568 |
| AluSx | NM_AluSx | GHI Custom | NM_AluSx |
| AMFR | NM_001144 | NCBI | NM_001144 |
| annexin I | NM_000700 | NCBI | NM_000700 |
| annexin II | NM_004039 | NCBI | NM_004039 |
| AP2B1 | NM_001282 | NCBI | NM_001282 |
| APC | NM_000038 | NCBI | NM_000038 |
| APN | NM_001150 | NCBI | NM_001150 |
| APP | AY011354 | NCBI | AY011354 |
| APP | M33112 | NCBI | M33112 |
| AREG | NM_001657 | NCBI | NM_001657 |
| ARG | NM_005158 | NCBI | NM_005158 |
| ASH1 | NM_018489 | NCBI | NM_018489 |
| B-actin | NM_001101 | NCBI | NM_001101 |
| B-Catenin | NM_001904 | NCBI | NM_001904 |
| B2M | NM_004048 | NCBI | NM_004048 |
| BAD | NM_004322 | NCBI | NM_004322 |
| BAD | AK023420 | NCBI | AK023420 |
| BAD | NM_032989 | NCBI | NM_032989 |

FIG. 6 CONT.

| Gene Name | Sequence ID | Sequence Source | GHIallgenes2-03.txt Accession Number |
|---|---|---|---|
| BAG1 | NM_004323 | NCBI | NM_004323 |
| Bak | NM_001188 | NCBI | NM_001188 |
| Bax | NM_004324 | NCBI | NM_004324 |
| BBC3 | NM_014417 | NCBI | NM_014417 |
| BCAR1 | NM_014567 | NCBI | NM_014567 |
| BCAR3 | NM_003567 | NCBI | NM_003567 |
| Bcl2 | NM_000633 | NCBI | NM_000633 |
| BCL2-related | BC017197 | NCBI | BC017197 |
| BCL2L10 | NM_020396 | NCBI | NM_020396 |
| BCL2L11 | NM_006538 | NCBI | NM_006538 |
| BCL2L12 | NM_052842 | NCBI | NM_052842 |
| BOX | NM_001191 | NCBI | NM_001191 |
| BCRP | NM_004827 | NCBI | NM_004827 |
| BECN1 | NM_003766 | NCBI | NM_003766 |
| BFGF | NM_007083 | NCBI | NM_007083 |
| BG675392 | BG675392 | NCBI | BG675392 |
| BID | NM_001196 | NCBI | NM_001196 |
| BIK | NM_001197 | NCBI | NM_001197 |
| BIN1 | NM_004305 | NCBI | NM_004305 |
| BIM | NM_000057 | NCBI | NM_000057 |
| BNIP1 | NM_013979 | NCBI | NM_013979 |
| BNIP2 | NM_004330 | NCBI | NM_004330 |
| BNIP3 | NM_004052 | NCBI | NM_004052 |
| BNIP3L | NM_004331 | NCBI | NM_004331 |
| BPAG1 | NM_015548 | NCBI | NM_015548 |
| BRAF | NM_004333 | NCBI | NM_004333 |
| BRCA1 | NM_007295 | NCBI | NM_007295 |
| BRCA2 | NM_000059 | NCBI | NM_000059 |
| BRK | NM_005975 | NCBI | NM_005975 |
| BRMS1 | AF159141 | NCBI | AF159141 |
| BRS3 | NM_001727 | NCBI | NM_001727 |
| BTC | NM_001729 | NCBI | NM_001729 |
| BTF3 | NM_001207 | NCBI | NM_001207 |
| BUB1 | NM_004336 | NCBI | NM_004336 |
| c-abl | NM_005157 | NCBI | NM_005157 |
| c-kit | NM_000222 | NCBI | NM_000222 |
| c-myb | NM_005375 | NCBI | NM_005375 |
| C20 orf1 | NM_012112 | NCBI | NM_012112 |
| C20orf103 | NK-012261 | NCBI | NM_012261 |
| c20orf108 | NM_080821 | NCBI | NM_080821 |
| CA9 | NM_001216 | NCBI | NM_001216 |
| CACNA2D2 | NM_006030 | NCBI | NM_006030 |
| Cad17 | NM_004063 | NCBI | NM_004063 |
| CASP8 | NM_033357 | NCBI | NM_033357 |
| CCNA2 | NM_001237 | NCBI | NM_001237 |
| CCNB1 | NM_031966 | NCBI | NM_031966 |
| CCNB2 | NM_004701 | NCBI | NM_004701 |
| CCND1 | NM_001758 | NCBI | NM_001758 |

FIG. 6 CONT.

| Gene Name | Sequence ID | Sequence Source | GHIallgenes2-03.txt Accession Number |
|---|---|---|---|
| CCND3 | NM_001760 | NCBI | NM_001760 |
| CCNE1 | NM_001238 | NCBI | NM_001238 |
| CCNE2 | NM_057749 | NCBI | NM_057749 |
| CCNE2 variant 1 | NM_057749var1 | NCBI | NM_057749 |
| CCNE2 variant 3 | NM_004702 | NCBI | NM_004702 |
| CD105 | NM_000118 | NCBI | NM_000118 |
| CD134 | NM_003327 | NCBI | NM_003327 |
| CD18 | NM_000211 | NCBI | NM_000211 |
| CD31 | NM_000442 | NCBI | NM_000442 |
| CD3z | NM_000734 | NCBI | NM_000734 |
| CD40 | NM_000074 | NCBI | NM_000074 |
| CD44E | X55150 | NCBI | X55150 |
| CD44s | M59040 | NCBI | M59040 |
| CD44v3 | AJ251595v3 | NCBI | AJ251595v3 |
| CD44v6 | AJ251595v6 | NCBI | AJ251595v6 |
| CD68 | NM_001251 | NCBI | NM_001251 |
| CD82 | NM_002231 | NCBI | NM_002231 |
| CD9 | NM_001769 | NCBI | NK-001769 |
| CDC20 | NM_001255 | NCBI | NM_001255 |
| cdc25A | NM_001789 | NCBI | NM_001789 |
| CDC25B | NM_021874 | NCBI | NM_021874 |
| CDH1 | NM_004360 | NCBI | NM_004360 |
| CDX2 | NM_001265 | NCBI | NM_001265 |
| CEACAM6 | NM_002483 | NCBI | NM_002483 |
| CEGP1 | NM_020974 | NCBI | NM_020974 |
| CEGP1 intron 1 | NM_020974int1 | NCBI | NM_020974int1 |
| CEGP1 intron 2 | NM_020974int2 | NCBI | NM_020974int2 |
| CEGP1 intron 3 | NM_020974int3 | NCBI | NM_020974int3 |
| CEGP1 intron 4 | NM_020974int4 | NCBI | NM_020974int4 |
| CEGP1 intron 5 | NM_020974int5 | NCBI | NM_020974int5 |
| CEGP1 intron 7 | NM_020974int7 | NCBI | NM_020974int7 |
| CGA | NM_001275 | NCBI | NM_001275 |
| CHAF1B | NM_005441 | NCBI | NM_005441 |
| chk1 | NM_001274 | NCBI | NM_001274 |
| chk2 | NM_007194 | NCBI | NM_007194 |
| CIAP1 | NM_001166 | NCBI | NM_001166 |
| CIAP2 | NM_001165 | NCBI | NM_001165 |
| CKAP4 | NM_006825 | NCBI | NM_006825 |
| Claudin | 4 NM_001305 | NCBI | NM_001305 |
| cMet | NM_000245 | NCBI | NM_000245 |
| cMYC | NM_002467 | NCBI | NM_002467 |
| CNN | NM_001299 | NCBI | NM_001299 |
| COL1A1 | NM_000088 | NCBI | NM_000088 |
| COL1A2 | NM_000089 | NCBI | NM_000089 |
| Contig 27882 | AK000618 | NCBI | AK000618 |
| Contig 36744 | XM_087225 | NCBI | XM-087225 |
| Contig 51037 | XM_058945 | NCBI | XM_058945 |
| Contig38438 | AI744123 | NCBI | AI744123 |

FIG. 6 CONT.

| Gene Name | Sequence ID | Sequence Source | GHIallgenes2-03.txt Accession Number |
|---|---|---|---|
| Contig44799 | Contig44799 | Rosetta Contigs | Contig44799 |
| Contig46653 | Contig46653 | Rosetta Contigs | Contig46653 |
| Contig47405 | Contig47405 | Rosetta Contigs | Contig47405 |
| COX2 | NM_000963 | NCBI | NM_000963 |
| CRBP | NM_002899 | NCBI | NM_002899 |
| cripto | NM_003212 | NCBI | NM_003212 |
| CRK7 | NM_016507 | NCBI | NM_016507 |
| CRMP1 | NM_001313 | NCBI | NM_001313 |
| CSF1 | NM_000757 | NCBI | NM_000757 |
| CSF1R | NM_005211 | NCBI | NM_005211 |
| CSF3 | NM_000759 | NCBI | NM_000759 |
| CSNK1D | NM_001893 | NCBI | NM_001893 |
| CSTF1 | NM_001324 | NCBI | NM_001324 |
| CTSB | NM_001908 | NCBI | NM_001908 |
| CTSD | NM_001909 | NCBI | NM_001909 |
| CTSH | NM_004390 | NCBI | NM_004390 |
| CTSL | NM_001912 | NCBI | NM_001912 |
| CTSL2 | NM_001333 | NCBI | NM_001333 |
| Cyclin C | NM_005190 | NCBI | NM_005190 |
| Cyclin G1 | NM_004060 | NCBI | NM_004060 |
| Cyclin G2 | NM_004354 | NCBI | NM_004354 |
| Cyclin K | BC015935 | NCBI | BC015935 |
| CYP | NM_006347 | NCBI | NM_006347 |
| CYP11B1 | NM_000497 | NCBI | NM_000497 |
| CYP17 | NM_000102 | NCBI | NM_000102 |
| CYP1A1 | NM_000499 | NCBI | NM_000499 |
| CYP1A2 | NM_000761 | NCBI | NM_000761 |
| CYP1B1 | NM_000104 | NCBI | NM_000104 |
| CYP21A2 | NM_000500 | NCBI | NM_000500 |
| CYP24 | NM_000782 | NCBI | NM_000782 |
| CYP27A1 | NM_000784 | NCBI | NM_000784 |
| CYP27B1 | NM_000785 | NCBI | NM_000785 |
| CYP2A13 | NM_000766 | NCBI | NM_000766 |
| CYP2A6 | NM_000762 | NCBI | NM_000762 |
| CYP2A7 | NM_000764 | NCBI | NM_000764 |
| CYP2A7 | NM_030589 | NCBI | NM_030589 |
| CYP2C18 | NM_000772 | NCBI | NM_000772 |
| CYP2C19 | NM_000769 | NCBI | NM_000769 |
| CYP2C8 | NM_030878 | NCBI | NM_030878 |
| CYP2C8 | NM_000770 | NCBI | NM_000770 |
| CYP2C9 | NM_000771 | NCBI | NM_000771 |
| CYP2D6 | NM_000106 | NCBI | NM_000106 |
| CYP2E | NM_000773 | NCBI | NM_000773 |
| CYP2F1 | NM_000774 | NCBI | NM_000774 |
| CYP2S1 | NM_030622 | NCBI | NM_030622 |
| CYP39A1 | NM_016593 | NCBI | NM_016593 |
| CYP3A4 | NM_017460 | NCBI | NM_017460 |
| CYP3A43 | NM_022820 | NCBI | NM_022820 |

FIG. 6 CONT.

| Gene Name | Sequence ID | Sequence Source | GHIallgenes2-03.txt Accession Number |
|---|---|---|---|
| CYP4F12 | NM_023944 | NCBI | NM_023944 |
| CYP4F2 | NM_001082 | NCBI | NM_001082 |
| CYP51 | NM_000786 | NCBI | NM_000786 |
| CYP7A1 | NM_000780 | NCBI | NM_000780 |
| CYP7B1 | NM_004820 | NCBI | NM_004820 |
| CYP8B1 | NM_004391 | NCBI | NM_004391 |
| DAPK1 | NM_004938 | NCBI | NM_004938 |
| DBC2 | NM_015178 | NCBI | NM_015178 |
| DCC_exons18-23 | X76132-18-23 | NCBI | X76132_18-23 |
| DCC_exons6-7 | X76132_6-7 | NCBI | X76132_6-7 |
| DCK | NM_000788 | NCBI | NM_000788 |
| DCR3 | NM_016434 | NCBI | NM_016434 |
| DHFR | NM_000791 | NCBI | NM_000791 |
| DHPS | NM_013407 | NCBI | NM_013407 |
| DIABLO | NM_019887 | NCBI | NM_019887 |
| DKFZp564 | XM_047080 | NCBI | XM_047080 |
| DKFZp586M0723 | AL050227 | NCBI | AL050227 |
| DNMT3A | NM_022552 | NCBI | NM_022552 |
| DPYD | NM_000110 | NCBI | NM_000110 |
| DR4 | NM_003844 | NCBI | NM_003844 |
| DR5 | NM_003842 | NCBI | NM_003842 |
| E2F1 | NM_005225 | NCBI | NM_005225 |
| EDN1 endothelin | NM_001955 | NCBI | NM_001955 |
| EGF | NM_001963 | NCBI | NM_001963 |
| EGFR | NM_005228 | NCBI | NM_005228 |
| EGFRd27 | EGFRd27 | GHI Custom | EGFRd27 |
| EIF4E | NM_001968 | NCBI | NM_001968 |
| EIF4EL3 | NM_004846 | NCBI | NM_004846 |
| EMP1 | NM_001423 | NCBI | NM_001423 |
| EMS1 | NM_005231 | NCBI | NM_005231 |
| EN01 | NM_001428 | NCBI | NM_001428 |
| EpCAM | NM_002354 | NCBI | NM_002354 |
| EPHX1 | NM_000120 | NCBI | NM_000120 |
| ER2 | NM_001437 | NCBI | NM_001437 |
| ErbB3 | NM_001982 | NCBI | NM_001982 |
| ERBB4 | NM_005235 | NCBI | NM_005235 |
| ERCC1 | NM_001983 | NCBI | NM_001983 |
| EREG | NM_001432 | NCBI | NM_001432 |
| ERK1 | Z11696 | NCBI | Z11696 |
| ERK2 | NM_002745 | NCBI | NM_002745 |
| ERRa | NM_004451 | NCBI | NM_004451 |
| ESM1 | NM_007036 | NCBI | NM_007036 |
| EstR1 | NM_000125 | NCBI | NM_000125 |
| F2 | NM_000506 | NCBI | NM_000506 |
| F2R | NM_001992 | NCBI | NM_001992 |
| F2RL2 | NM_004101 | NCBI | NM_004101 |
| fas | NM_000043 | NCBI | NM_000043 |
| fas1 | NM_000639 | NCBI | NM_000639 |

FIG. 6 CONT.

| Gene Name | Sequence ID | Sequence Source | GHIallgenes2-03.txt Accession Number |
|---|---|---|---|
| FBXO5 | NM_012177 | NCBI | NM_012177 |
| FGF 19 | NM_005117 | NCBI | NM_005117 |
| FGF1 | NM_000800 | NCBI | NM_000800 |
| FGF18 | NM_003862 | NCBI | NM_003862 |
| FGF2 | NM_002006 | NCBI | NM_002006 |
| FGF8 | NM_033163 | NCBI | NM_033163 |
| FGFR 2 | NM_023028 | NCBI | NM_023028 |
| FGFR 3 | NM_000142 | NCBI | NM_000142 |
| FGFR1 | NM_023109 | NCBI | NM_023109 |
| FGFR4 | NM_002011 | NCBI | NM_002011 |
| FHIT | NM_002012 | NCBI | NM_002012 |
| FKBP4 | NM_002014 | NCBI | NM_002014 |
| FL310713 | NM_018189 | NCBI | NM_018189 |
| FLJ20354 | NM_017779 | NCBI | NM_017779 |
| FLT1 | NM_002019 | NCBI | NM_002019 |
| FN1 | NM_002026 | NCBI | NM_002026 |
| FOLR1 | NM_016730 | NCBI | NM_016730 |
| FOXM1 | NM_021953 | NCBI | NM_021953 |
| FOXM1 intron 3 | NM_021953 int3 | NCBI | NM_021953 int3 |
| FOXM1 intron 4 | NM_021953 int4 | NCBI | NM_021953 int4 |
| FOXM1 intron 5 | NM_021953 int5 | NCBI | NM_021953 int5 |
| FOXM1 intron 7 | NM_021953 int7 | NCBI | NM_021953 int7 |
| FPPS | NM_002004 | NCBI | NM_002004 |
| FRPI | NM_003012 | NCBI | NM_003012 |
| Furin | NM_002569 | NCBI | NM_002569 |
| FUS | NM_004960 | NCBI | NM_004960 |
| FUT1 | NM_000148 | NCBI | NM_000148 |
| FUT2 | NM_000511 | NCBI | NM_000511 |
| G-Catenin | NM_002230 | NCBI | NM_002230 |
| GAMMA | NM_003890 | NCBI | NM_003890 |
| GAPDH | NM_002046 | NCBI | NM_002046 |
| GATA3 | NM_002051 | NCBI | NM_002051 |
| GCLC | NM_001498 | NCBI | NM_001498 |
| GCLM | NM_002061 | NCBI | NM_002061 |
| GGPS1 | NM_004837 | NCBI | NM_004837 |
| GGT | X98922 | NCBI | X98922 |
| gp130 | NM_002184 | NCBI | NM_002184 |
| GPC1 | NM_002081 | NCBI | NM_002081 |
| GPC3 | NM_004484 | NCBI | NM_004484 |
| GPX1 | NM_000581 | NCBI | NM_000581 |
| GPX2 | NM_002083 | NCBI | NM_002083 |
| GPX3 | NM_002084 | NCBI | NM_002084 |
| GPX4 | NM_002085 | NCBI | NM_002085 |
| GRB7 | NM_005310 | NCBI | NM_005310 |
| GRO1 | NM_001511 | NCBI | NM_001511 |
| GRP | NM_002091 | NCBI | NM_002091 |
| GRPR | NM_005314 | NCBI | NM_005314 |
| GSN | NM_000177 | NCBI | NM_000177 |

FIG. 6 CONT.

| Gene Name | Sequence ID | Sequence Source | GHIallgenes2-03.txt Accession Number |
|---|---|---|---|
| GSTM1 | NM_000561 | NCBI | NM_000561 |
| GSTM3 | NM_000849 | NCBI | NM_000849 |
| GSTp | NM_000852 | NCBI | NM_000852 |
| GSTT1 | NM_000853 | NCBI | NM_000853 |
| GSTT2 | NM_000854 | NCBI | NM_000854 |
| GUS | NM_000181 | NCBI | NM_000181 |
| H2AFZ | NM_002106 | NCBI | NM_002106 |
| Ha-Ras | NM_005343 | NCBI | NM_005343 |
| HB-EGF | NM_001945 | NCBI | NM_001945 |
| hCRA a | U78556 | NCBI | U78556 |
| hENT1 | NM_004955 | NCBI | NM_004955 |
| Hepsin | NM_002151 | NCBI | NM_002151 |
| HER2 | NM_004448 | NCBI | NM_004448 |
| her2P | J05264 | NCBI | J05264 |
| HGF | M29145 | NCBI | M29145 |
| HIF1A | NM_001530 | NCBI | NM_001530 |
| HLA-DPB1 | NM_002121 | NCBI | NM_002121 |
| HLA-G | NM_002127 | NCBI | NM_002127 |
| HNF3A | NM_004496 | NCBI | NM_004496 |
| HNRPAB | NM_004499 | NCBI | NM_004499 |
| HOXA5 | NM_019102 | NCBI | NM_019102 |
| HOXB7 | NM_004502 | NCBI | NM_004502 |
| IBSP | NM_004967 | NCBI | NM_004967 |
| Id-3 | NM_002167 | NCBI | NM_002167 |
| ID1 | NM_002165 | NCBI | NM_002165 |
| ID2 | NM_002166 | NCBI | NM_002166 |
| IER3 | NM_052815 | NCBI | NM_052815 |
| IGF1 | NM_000618 | NCBI | NM_000618 |
| IGF1R | NM_000875 | NCBI | NM_000875 |
| IGF2 | NM_000612 | NCBI | NM_000612 |
| IGFBP1 | XM004688 | NCBI | XM_004688 |
| IGFBP2 | NM_000597 | NCBI | NM_000597 |
| IGFBP2(XM) | XM_002636 | NCBI | XM_002636 |
| IGFBP3 | NM_000598 | NCBI | NM_000598 |
| IGFBP4 | XM_049937 | NCBI | XM_049937 |
| IGFBP5 | AY052629 | NCBI | AY052629 |
| IGFBP5 | NM_000599 | NCBI | NM_000599 |
| IGFBP6 | NM_002178 | NCBI | NM_002178 |
| IGFBP7 | NM_001553 | NCBI | NM_001553 |
| IL10 | NM_000572 | NCBI | NM_000572 |
| IL6 | NM_000600 | NCBI | NM_000600 |
| ILT-2 | NM_006669 | NCBI | NM_006669 |
| ING1 | NM_005537 | NCBI | NM_005537 |
| INSM1 | NM_002196 | NCBI | NM_002196 |
| IRS1 | NM_005544 | NCBI | NM_005544 |
| ITGA3 | NM_002204 | NCBI | NM_002204 |
| ITGA7 | NM_002206 | NCBI | NM_002206 |
| ITGB3 | NM_000212 | NCBI | NM_000212 |

FIG. 6 CONT.

| Gene Name | Sequence ID | Sequence Source | GHIallgenes2-03.txt Accession Number |
|---|---|---|---|
| k-ras | NM_033360 | NCBI | NM_033360 |
| KB1527G9 8q23 | KB1527G9 | NCBI | KB1527G9 |
| KDR | NM_002253 | NCBI | NM_002253 |
| Ki-67 | NM_002417 | NCBI | NM_002417 |
| KIAA1209 | AJ420468 | NCBI | AJ420468 |
| KitIng | NM_000899 | NCBI | NM_000899 |
| KLK10 | NM_002776 | NCBI | NM_002776 |
| KLK11 | NM_006853 | NCBI | NM_006853 |
| KNSL2 | BC000712 | NCBI | BC000712 |
| KRT4 | NM_002272 | NCBI | NM_002272 |
| KRT14 | NM_000526 | NCBI | NM_000526 |
| KRT17 | NM_000422 | NCBI | NM_000422 |
| KRT18 | NM_000224 | NCBI | NM_00.0224 |
| KRT19 | NM_002276 | NCBI | NM_002276 |
| KRT5 | NM_000424 | NCBI | NM_000424 |
| KRT8 | NM_002273 | NCBI | NM_002273 |
| LAMC2 | NM_005562 | NCBI | NM_005562 |
| LAMP2 | NM_013995 | NCBI | NM_013995 |
| LMNB1 | NM_005573 | NCBI | NM_005573 |
| LMYC | NM_012421 | NCBI | NM_012421 |
| LOC51038 | NM_015858 | NCBI | NM_015858 |
| LOT1 variant 1 | NM_002656 | NCBI | NM_002656 |
| Lot1 variant 2 | NM_006718 | NCBI | NM_006718 |
| LPL | NM_000237 | NCBI | NM_000237 |
| LTA | NM_000595 | NCBI | NM_000595 |
| M20259 | M20259 | NCBI | M20259 |
| MAGEE 1 | NM_016249 | NCBI | NM_016249 |
| MAPK4 | NM_002747 | NCBI | NM_002747 |
| Maspin | NM_002639 | NCBI | NM_002639 |
| MCJ | NM_013238 | NCBI | NM_013238 |
| MCL1 | NM_021960 | NCBI | NM_021960 |
| MCM2 | NM_004526 | NCBI | NM_004526 |
| MCM3 | NM_002388 | NCBI | NM_002388 |
| MCM6 | NM_005915 | NCBI | NM_005915 |
| MCM7 | NM_005916 | NCBI | NM_005916 |
| MCP1 | NM_002982 | NCBI | NM_002982 |
| MDM2 | NM_002392 | NCBI | NM_002392 |
| MDS028 | NM_018463 | NCBI | NM_018463 |
| MEL | NM_005370 | NCBI | NM_005370 |
| MELK | NM_014791 | NCBI | NM_014791 |
| Mgb1 | NM_002411 | NCBI | NM_002411 |
| MGMT | NM_002412 | NCBI | NM_002412 |
| MGST1 | NM_020300 | NCBI | NM_020300 |
| MLH1 | NM_000249 | NCBI | NM_000249 |
| MLL | NM_005933 | NCBI | NM_005933 |
| MMP12 | NM_002426 | NCBI | NM_002426 |
| MMP2 | NM_004530 | NCBI | NM_004530 |
| MMP9 | NM_004994 | NCBI | NM_004994 |

FIG. 6 CONT.

| Gene Name | Sequence ID | Sequence Source | GHIallgenes2-03.txt Accession Number |
|---|---|---|---|
| MRP1 | NM_004996 | NCBI | NM_004996 |
| MRP2 | NM_000392 | NCBI | NM_000392 |
| MRP3 | NM_003786 | NCBI | NM_003786 |
| MRP4 | NM_005845 | NCBI | NM_005845 |
| MSH2 | NM_000251 | NCBI | NM_000251 |
| MSH3 | NM_002439 | NCBI | NM_002439 |
| MSH6 | NM_000179 | NCBI | NM_000179 |
| MT3 | NM_005954 | NCBI | NM_005954 |
| MTA1 | NM_004689 | NCBI | NM_004689 |
| MUC1 | NM_002456 | NCBI | NM_002456 |
| MUC1 | J05582 | NCBI | J05582 |
| MUC3 | AF007194 | NCBI | AF007194 |
| MVP | NM_017458 | NCBI | NM_017458 |
| MYBL2 | NM_002466 | NCBI | NM_002466 |
| MYH11 | NM_002474 | NCBI | NM_002474 |
| MYLK | NM_053025 | NCBI | NM_053025 |
| MYRIP | NM_015460 | Incyte Diagnostic | NM_015460 |
| NADPHP450 | AF258341 | NCBI | AF258341 |
| NCAM1 | NM_000615 | NCBI | NM_000615 |
| NEK2 | NM_002497 | NCBI | NM_002497 |
| NFKBp50 | NM_003998 | NCBI | NM_003998 |
| NFKBp65 | NM_021975 | NCBI | NM_021975 |
| NMB | NM_021077 | NCBI | NM_021077 |
| NMBR | NM_002511 | NCBI | NM_002511 |
| NME1 | NM_000269 | NCBI | NM_000269 |
| NMU | NM_006681 | NCBI | NM_006681 |
| NMYC | NM_005378 | NCBI | NM_005378 |
| NPDO09 | NM_020686 | NCBI | NM_020686 |
| NR4A1 | NM_002135 | NCBI | NM_002135 |
| NRG1 | NM_013957 | NCBI | NM_013957 |
| NRP1 | NM_003873 | NCBI | NM_003873 |
| NRP2 | NM_003872 | NCBI | NM_003872 |
| ODC1 | NM_002539 | NCBI | NM_002539 |
| OPN, osteopontin | NM_000582 | NCBI | NM_000582 |
| ORC3 | NM_012381 | NCBI | NM_012381 |
| Osteonectin | NM_003118 | NCBI | NM_003118 |
| P14ARF | S78535 | NCBI | S78535 |
| p14ARF | NM_000077P14 | NCBI | NM_000077 |
| p16-INK4 | L27211 | NCBI | L27211 |
| P16INK4 | NM_000077 | NCBI | NM_000077 |
| p21 | NM_000389 | NCBI | NM_000389 |
| p27 | NM_004064 | NCBI | NM_004064 |
| P40 | NM_006824 | NCBI | NM_006824 |
| P53 | NM_000546 | NCBI | NM_000546 |
| p53R2 | AB036063 | NCBI | AB036063 |
| p63 | NM_003722 | NCBI | NM_003722 |
| P66 | AB032976 | NCBI | AB032976 |
| PAI1 | NM_000602 | NCBI | NM_000602 |

FIG. 6 CONT.

| Gene Name | Sequence ID | Sequence Source | GHIallgenes2-03.txt Accession Number |
|---|---|---|---|
| PBGD | X04217 | NCBI | X04217 |
| PCNA | NM_002592 | NCBI | NM_002592 |
| PCP4 | NM_006198 | NCBI | NM_006198 |
| PDGFA | NM_002607 | NCBI | NM_002607 |
| PDGFB | NM_002608 | NCBI | NM_002608 |
| PDGFC | NM_016205 | NCBI | NM_016205 |
| PDGFD | NM_025208 | NCBI | NM_025208 |
| PDGFRa | NM_006206 | NCBI | NM_006206 |
| PDGFRb | NM_002609 | NCBI | NM_002609 |
| PECI | NM_006117 | NCBI | NM_006117 |
| PGK1 | NM_000291 | NCBI | NM_000291 |
| PI3K | NM_002646 | NCBI | NM_002646 |
| PI3Kc2A | NM_002645 | NCBI | NM_002645 |
| PIK3R1 | M61906 | NCBI | M61906 |
| Pin1 | NM_006221 | NCBI | NM_006221 |
| PKCe | NM_005400 | NCBI | NM_005400 |
| PKLR | NM_000298 | NCBI | NM_000298 |
| PLAUR | NM_002659 | NCBI | NK-002659 |
| PLK | NM_005030 | NCBI | NM_005030 |
| PMS1 | NM_000534 | NCBI | NM_000534 |
| PMS2 | NM_000535 | NCBI | NM_000535 |
| PPARG | NM_005037 | NCBI | NM_005037 |
| PPM1D | NM_003620 | NCBI | NM_003620 |
| PR | NM_000926 | NCBI | NM_000926 |
| PRAME | NM_006115 | NCBI | NM_006115 |
| PRAME intron 1 | NM_006115int1 | NCBI | NM_006115int1 |
| PRAME intron 2 | NM_006115int2 | NCBI | NM_006115int2 |
| PRAME intron 3 | NM_006115int3 | NCBI | NM_006115int3 |
| PRAME intron 4 | NM_006115int4 | NCBI | NM_006115int4 |
| PRAME intron 5 | NM_006115int5 | NCBI | NM_006115int5 |
| PREP | NM_002726 | NCBI | NM_002726 |
| PRKCD | NM_006254 | NCBI | NM_006254 |
| PRKCG | NM_002739 | NCBI | NM_002739 |
| PRO2000 | NM_014109 | NCBI | NM_014109 |
| pS2 | NM_003225 | NCBI | NM_003225 |
| PTDO16 | NM_016125 | NCBI | NM_016125 |
| PTEN | NM_000314 | NCBI | NM_000314 |
| PTHLH | NM_002820 | NCBI | NM_002820 |
| PTPD1 | NM_007039 | NCBI | NM_007039 |
| PTTG1 | NM_004219 | NCBI | NM_004219 |
| PUNC | AK095529 | NCBI | AK095529 |
| Q9BQI9 | NM_031474 | NCBI | NM_031474 |
| Q9BSD3 | NM_031465 | NCBI | NM_031465 |
| RAB27B | NM_004163 | NCBI | NM_004163 |
| RAD51C | NM_058216 | NCBI | NM_058216 |
| RAD54L | NM_003579 | NCBI | NM_003579 |
| RANBP2 | NM_006267 | NCBI | NM_006267 |
| RARA | NM_000964 | NCBI | NM_000964 |

FIG. 6 CONT.

| Gene Name | Sequence ID | Sequence Source | GHIallgenes2-03.txt Accession Number |
|---|---|---|---|
| RARB | NM_016152 | NCBI | NM_016152 |
| RASSF1 | NM_007182 | NCBI | NM_007182 |
| RB1 | NM_000321 | NCBI | NM_000321 |
| RBM5 | NM_005778 | NCBI | NM_005778 |
| RBP4 | NM_006744 | NCBI | NM_006744 |
| RERG | NM_032918 | NCBI | NM_032918 |
| RFC | NM_003056 | NCBI | NM_003056 |
| RFC4 | NM_002916 | NCBI | NM_002916 |
| rhoc | NM_005167 | NCBI | NM_005167 |
| RIZ1 | NM_012231 | NCBI | NM_012231 |
| RNase P | RNaseP | GHI Custom | RNaseP |
| RPL19 | NM_000981 | NCBI | NM_000981 |
| RPLPO | NM_001002 | NC5I | NM_001002 |
| RPS6KB1 | NM_003161 | NCBI | NM_003161 |
| RRM1 | NM_001033 | NCBI | NM_001033 |
| RUNX1 | NM_001754 | NCBI | NM_001754 |
| SDC1 | NM_002997 | NCBI | NM_002997 |
| SEMA3B | NM_004636 | NCBI | NM_004636 |
| SEMA3F | NM_004186 | NCBI | NM_004186 |
| SERPINC1 | NM_000488 | NCBI | NM_000488 |
| SIR2 | NM_012238 | NCBI | NM_012238 |
| SLC19A3 | NM_025243 | NCBI | NM_025243 |
| SLC20A1 | NM_005415 | NCBI | NM_005415 |
| SLC2A3 | NM_006931 | NCBI | NM_-006931 |
| Smad4 | NM_005359 | NCBI | NM_005359 |
| SNRPF | NM_003095 | NCBI | NM_003095 |
| SPRY1 | AK026960 | NCBI | AK026960 |
| SPRY2 | NM_005842 | NCBI | NM_005842 |
| Src | NM_004383 | NCBI | NM_004383 |
| STAT1 | NM_007315 | NCBI | NM_007315 |
| STAT3 | NM_003150 | NCBI | NM_003150 |
| STAT5A | NM_003152 | NCBI | NM_0031-52 |
| STAT5B | NM_012448 | NCBI | NM_012448 |
| STC1 | NM_003155 | NCBI | NM_003155 |
| STC2 | AK027663 | NCBI | AK027663 |
| STC2 | NM_003714 | NCBI | NM_003714 |
| STK11 | NM_000455 | NCBI | NM_000455 |
| STK15 | NM_003600 | NCBI | NM_003600 |
| STK15 intron 1 | NM_003600int1 | NCBI | NM_003600int1 |
| STK15 intron 2 | NM_003600int2 | NCBI | NM_003600int2 |
| STK15 intron 3 | NM_003600int3 | NCBI | NM_003600int3 |
| STK15 intron 4 | NM_003600int4 | NCBI | NM_003600int4 |
| STK15 intron 6 | NM_003600int6 | NCBI | NM_003600int6 |
| STMY3 | NM_005940 | NCBI | NM_005940 |
| SUHW1 | NM_080740 | NCBI | NM_080740 |
| SURF6 | NM_006753 | NCBI | NM_006753 |
| Surfact A1 | NM_005411 | NCBI | NM_005411 |
| SURV | NM_001168 | NCBI | NM_001168 |

FIG. 6 CONT.

| Gene Name | Sequence ID | Sequence Source | GHIallgenes2-03.txt Accession Number |
|---|---|---|---|
| SXR | NM_003889 | NCBI | NM_003889 |
| SYK | NM_003177 | NCBI | NM_003177 |
| TAGLN | NM_003186 | NCBI | NM_003186 |
| TBD | NM_016261 | NCBI | NM_016261 |
| TBP | NM_003194 | NCBI | NM_003194 |
| TBX2 | NM_005994 | NCBI | NM_005994 |
| TEK | NM_000459 | NCBI | NM_000459 |
| TERC | U86046 | NCBI | U86046 |
| TERT | NM_003219 | NCBI | NM_003219 |
| TFF3 | NM_003226 | NCBI | NM_003226 |
| TFRC | NM_003234 | NCBI | NM_003234 |
| TGFA | NM_003236 | NCBI | NM_003236 |
| TGFb1 | NM_000660 | NCBI | NM_000660 |
| TGFB3 | NM_003239 | NCBI | NM_003239 |
| TGFBR2 | NM_003242 | NCBI | NM_003242 |
| Thrombospondin 1 | NM_003246 | NCBI | NM_003246 |
| Thymosin B | NM_021992 | NCBI | NM_021992 |
| TIE | NM_005424 | NCBI | NM_005424 |
| TIMP1 | NM_003254 | NCBI | NM_003254 |
| TIMP2 | NM_003255 | NCBI | NM_003255 |
| TIMP3 | NM_000362 | NCBI | NM_000362 |
| TITF1 | NM_003317 | NCBI | NM_003317 |
| TJP1 | NM_003257 | NCBI | NM_003257 |
| TK1 | NM_003258 | NCBI | NM_003258 |
| TNF | NM_000594 | NCBI | NM_000594 |
| TNFRSF11A | NM_003839 | NCBI | NM_003839 |
| TNFRSF11B | NM_002546 | NCBI | NM_002546 |
| TNFSF11 | NM_003701 | NCBI | NM_003701 |
| TNFSF11 | NM_033012 | NCBI | NM_033012 |
| TOP2A | NM_001067 | NCBI | NM_001067 |
| TOP2AF | AF071738 | NCBI | AF071738 |
| TOP2B | NM_001068 | NCBI | NM_001068 |
| TP | NM_001953 | NCBI | NM_001953 |
| TP53BP1 | NM_005657 | NCBI | NM_005657 |
| TP53BP2 | NM_005426 | NCBI | NM_005426 |
| TRAIL | NM_003810 | NCBI | NM_003810 |
| TS | NM_001071 | NCBI | NM_001071 |
| TSC2 | NM_000548 | NCBI | NM_000548 |
| TULP3 | NM_003324 | NCBI | NM_003324 |
| upa | NM_002658 | NCBI | NM_002658 |
| VCAM1 | NM_001078 | NCBI | NM_001078 |
| VDR | NM_000376 | NCBI | NM_000376 |
| VEGF | NM_003376 | NCBI | NM_003376 |
| VEGFB | NM_003317 | NCBI | NM_003377 |
| VEGFC | NM_005429 | NCBI | NM_005429 |
| vim | NM_003380 | NCBI | NM_003380 |
| WISP1 | NM_003882 | NCBI | NM_003882 |
| Wnt-5a | NM_003392 | NCBI | NM_003392 |

FIG. 6 CONT.

| Gene Name | Sequence ID | Sequence Source | GHIallgenes2-03.txt Accession Number |
|---|---|---|---|
| Wnt-5b | NM_032642 | NCBI | NM_032642 |
| wwox | NM_016373 | NCBI | NM_016373 |
| XIAP | NM_001167 | NCBI | NM_001167 |
| XIST | M97168 | NCBI | M97168 |
| YB-1 | NM_004559 | NCBI | NM_004559 |
| ZNF217 | NM_006526 | NCBI | NM_006526 |

USE OF INTRONIC RNA TO MEASURE GENE EXPRESSION

The present invention claims the benefit under 35 U.S.C. §119(e) of provisional application Ser. No. 60/448,991 filed on Feb. 20, 2003, the entire disclosure of which is hereby expressly incorporated by reference.

BACKGROUND OF THE INVENTION

Field of the Invention

It is well recognized that gene expression within cells and tissues can indicate the physiologic and or pathologic status of the cell, tissue or patient. For several decades, gene expression, as measured by immunohistochemical analysis of protein markers, has been used to make treatment decisions. For example, levels of estrogen receptor and progesterone receptor measured this way are now routinely used to select breast cancer patients for treatment with anti-estrogen drugs.

More recent research literature provides evidence that tissue levels of mRNA species have diagnostic and prognostic value. This is a promising development because the technologies for measurement of cellular RNA levels, as exemplified by multiple RT-PCR and DNA array platforms, can be very sensitive, specific and quantitative. RT-PCR is recognized as generally more sensitive than DNA array technology. However, RT-PCR probe/primer design and selection can be challenging, because multiple criteria exist for optimal performance. This challenge is particularly great when the sample RNA to be studied comes from fixed, wax-embedded tissue, because such RNA tends to be highly fragmented (K.Specht et al., Am. J. Pathol 158: 419-29 [2001]; T. E. Godfrey et al., J. Mol. Diagnostics 2:84-91 [2000]).

It is accepted practice to measure the expression of any given gene by assaying the level of any of its transcribed, spliced, mature mRNA sequences (exon, as opposed to intron, sequence). In theory, an exon is defined as any segment of an interrupted gene that is represented in the mature RNA product, and an intron is defined as a segment of DNA that is transcribed but removed from within the transcript by splicing together the exons on either side of it [B. Lewin. Genes IV, Cell Press, Cambridge Mass. 1990]. The rationale for the accepted practice of using exon sequences is theoretically straightforward because the mature RNAs [mRNAs] encode proteins, which define cell phenotypes, whereas intronic RNA is considered to have comparatively little influence on cell phenotype. Moreover, the prevailing view is that introns are rapidly degraded and therefore more difficult to detect than exon sequences {see introductions of the following articles: Thomas et al., J. Virol. 76:532-40 [2002]; Clement et al., J. Biol. Chem. 276:16919-30 [2001]; Sharp et al., Ann. Rev. Biochem. 55:1119-1150 [1986]}.

The present invention concerns the use of intronic RNA for measuring gene expression. It will be shown that intronic RNA sequences tend to be readily detected by RT-PCR, even using extensively degraded RNA from fixed tissues. Furthermore, they tend to correlate in their expression with their respective exons. The latter point is particularly unexpected because little or no evidence exists that the ratio of the overall rate constants for synthesis and turnover of transcribed intron and exon sequences are similar. In fact, the scientific literature provides evidence for the complexity of pre-mRNA and spliced intron turnover. For example, pre-mRNA can exist in multiple kinetic pools (Elliott and Rosbash, Exp. Cell Res. 229:181-8 [1996]), with subpopulations containing intron RNAs that are not efficiently spliced out and are transported to the cytoplasm as "immature" mRNA species, where they can decay at rates different than nuclear intron RNA sequences (Wang et al., Proc. Natl. Acad. Sci. USA 94:4360-5 [1997]). Furthermore, certain spliced intron RNAs seem to enter the cytoplasm in lariat structure (Clement et al., RNA 5:206-20 [1999]).

SUMMARY OF THE INVENTION

The present invention is based on experimental evidence demonstrating that transcribed intron sequences, which by definition are present in heterogeneous nuclear RNA but typically are not incorporated into mRNA, have diagnostic and prognostic utility. This is a significant discovery for several reasons. Typically, intron sequences are longer than exon sequences, by twenty fold or more. Thus, introns, given their much greater average length, provide proportionally increased opportunity for optimal gene expression probe design, for example, in the case of RT-PCR, creation of probe/primer sets that possess better technical performance. Independently, because intron sequences evolve more rapidly than exon sequences, intronic RNAs are well-suited to monitor the expression of different closely related members of a gene family.

In one aspect, the invention concerns a single-stranded oligonucleotide molecule comprising or complementary to a target sequence within a transcribed intronic RNA sequence of a target gene, wherein the expression of the intronic RNA sequence has been determined to roccelate with the expression of an exonic mRNA sequence within the target gene.

The single-stranded oligonucleotide molecule can, for example, be a PCR primer or probe. The target sequence typically, but not necessarily, is at least about 55 nucleotide bases long, or at least about 60 nucleotide bases long.

In an embodiment, the single-stranded oligonucleotide molecule is a PCR primer, which is about 17- to 30 nucleotide bases in length.

In another embodiment, the PCR primer contains about 20% to about 80% G+C bases.

In yet another embodiment, the PCR primer has a melting temperature (Tm) of between about 50° C. to about 70° C.

In a further embodiment, the single-stranded oligonucleotide molecule is a PCR probe, which may be detectably labeled, for example with a reporter fluorescent dye and a quencher fluorescent dye.

In a further specific embodiment, the target gene is CEGP1, FGXM1, PRAME, or STK15.

In another specific embodiment, the target gene is selected from the genes listed in FIG. 6.

In a still further specific embodiment, the target gene is selected from the group consisting of B-actin, BAG1, bcl-2, CCNB1, CD68,CEGP1, CTSL2, EstR1, GAPDH, GUS, GRB7, HER2, Ki-67, MYBL2, PR, RPLPO, STK15, STMY3, SURVIVIN, and TFRC.

In another aspect, the invention concerns a method for monitoring gene expression in a biological sample, comprising:
  (a) providing a polynucleotide complementary to an intronic RNA sequence within a target gene, wherein the expression of such intronic RNA sequence correlates with the expression of an exonic mRNA sequence within the target gene;
  (b) hybridizing the polynucleotide to the intronic RNA sequence to form a polynucleotide-intronic RNA complex; and
  (c) detecting the polynucleotide-intronic RNA complex.

In a particular aspect, expression of the target gene is measured by RT-PCR, in which case an intron-based primer/probe set can be used in the above process.

In another aspect, the invention concerns methods of using intron-based sequences to design and create primer-probe sets for RT-PCR. Such primers and probes are particularly suitable to detect and quantify levels of intron RNA in fixed, paraffin-embedded tissue (FPET) specimens, for high sensitivity gene expression analysis. Accordingly, in a further aspect, the invention concerns using intron-based primer-probe sets in gene expression profiling assays, such as gene expression analysis of FPET samples to diagnose and/or predict the prognosis of various pathologic conditions.

In particular, the invention concerns a method of preparing a single-stranded oligonucleotide molecule for amplification of a target gene, and measuring the level of an intronic RNA species comprising:

(a) identifying at least one intron sequence within the target gene, wherein the expression of the intron sequence correlates with the expression of an exon sequence within the target gene;

(b) preparing a single-stranded oligonucleotide molecule that corresponds to at least a portion of the transcribed intron sequence; and (c) using the oligonucleotide molecule to measure gene expression.

Just as before, gene expression can be measured, for example, by RT-PCR, in which case an intron-based primer/probe set (consisting of two primers and a probe) is used to measure gene expression.

If the oligonucleotide is a forward primer, it is typically designed to comprise 5'-sequences of a target sequence within the transcribed intron sequence. If the oligonucleotide is a reverse primer, it is typically designed to complement 5'-sequences of a target sequence downstream of the forward primer within the transcribed intron sequence. It is important to identify and use a sufficiently long target sequence for PCR amplification. The target sequence generally should be at least about 50 nucleotide bases long, in particular at least 55 nucleotide bases long, in some embodiments at least about 60 nucleotide bases long. The PCR primers and probes are designed following well known principles. Thus, the PCR primer is typically 17-30 nucleotide bases in length, and usually contains about 20% to 80% G+C bases. It is desirable to design PCR primers with a melting temperature (Tm) between about 50° C. and about 70° C.

When the single-stranded oligonucleotide molecule is a PCR probe, it is usually designed to comprise or complement an internal portion of a target sequence within the transcribed intron sequence. For TaqMan® amplification, the PCR probe is labeled with a reporter fluorescent dye and a quencher moiety.

In another aspect, the invention concerns a method for measuring the expression of a gene by amplifying a target gene by polymerase chain reaction (PCR) comprising:

(a) identifying at least one target intron sequence within the target gene, wherein the expression of the intron sequence correlates with the expression of a corresponding exon sequence within the target gene; and (b) amplifying the transcribed target intron sequence using an intron-specific PCR primer/probe set.

The target intron sequence is typically at least about 50 bases long, and the PCR primer and probe set is designed to correspond to unique sequences within the transcribed target intron sequence.

In yet another aspect, the invention concerns a method for amplifying RNA fragments in a sample representing at least one gene of interest, comprising the steps of:

(a) contacting the sample with at least one set of PCR primers and probe; and (b) performing PCR amplification, wherein the PCR primers and probe are designed based upon an intron sequence identified within the gene of interest, and wherein the expression of the intron sequence correlates with the expression of an exon sequence within the gene of interest.

In particular embodiment, the PCR primers and probe are typically designed based upon a unique sequence within the intron identified. In another embodiment, the sample comprises fragmented RNA representing multiple genes of interest, and is contacted with a pool of PCR primers and probes designed based upon unique sequences within introns present in the genes of interest.

In a preferred embodiment, the amplification is performed on a fixed, paraffin-embedded tissue (FPET) sample, which can, for example, originate from a tumor biopsy obtained from a human patient. The tumor can be any kind of solid tumor, such as, for example, breast cancer, lung cancer, or colorectal cancer. The tumor tissue can be harvested by a variety of methods, including fine needle biopsy, core biopsy or resection.

In a particular embodiment, the invention concerns methods using intron-based PCR primer-probe sets in gene expression analysis to predict the likelihood of recurrent disease for patients with early breast cancer.

In a further aspect, the invention concerns an array comprising a plurality of polynucleotides hybridizing to target genes of interest, wherein preferably at least 70% of the polynucleotides comprises intron sequences.

In yet another aspect, the invention concerns intron-based amplicon sequences, and their use in gene expression analysis.

In a particular embodiment the invention concerns gene expression analysis of a biological sample representative of invasive breast cancer based on determining the expression levels of the RNA transcripts or expression products of a gene or gene set selected from the group consisting of:

(a) Bcl2, cyclinG1, NFKBp65, NME1, EPHX1, TOP2B, DR5, TERC, Src, DIABLO;

(b) Ki67, XIAP, hENT1, TS, CD9, p27, cyclinG1, pS2, NFKBp65, CYP3A4;

(c) GSTM1, XIAP, Ki67, TS, cyclinG1, p27, CYP3A4, pS2, NFKBp65, ErbB3;

(d) PR, NME1, XIAP, upa, cyclinG1, Contig51037, TERC, EPHX1, ALDH1A3, CTSL;

(e) CA9, NME1, TERC, cyclinG1, EPHX1, DPYD, Src, TOP2B, NFKBp65, VEGFC;

(f) TFRC, XIAP, Ki67, TS, cyclinG1, p27, CYP3A4, pS2, ErbB3, NFKBp65;

(g) Bcl2, PRAME, cyclinG1, FOXM1, NFKBp65, TS, XIAP, Ki67, CYP3A4, p27;

(h) FOXM1, cyclinG1, XIAP, Contig51037, PRAME, TS, Ki67, PDGFRa, p27, NFKBp65;

(i) PRAME, FOXM1, cyclinG1, XIAP, Contig51037, TS, Ki6, PDGFRa, p27, NFKBp65;

(j) Ki67, XIAP, PRAME, hENT1, contig51037, TS, CD9, p27, ErbB3, cyclinG1;

(k) STK15, XIAP, PRAME, PLAUR, p27, CTSL, CD18, PREP, p53, RPS6KB1;

(l) GSTM1, XIAP, PRAME, p27, Contig51037, ErbB3, GSTp, EREG, ID1, PLAUR;

(m) PR, PRAME, NME1, XIAP, PLAUR, cyclinG1, Contig51037, TERC, EPHX1, DR5;
(n) CA9, FOXM1, cyclinG1, XIAP, TS, Ki67, NFKBp65, CYP3A4, GSTM3, p27;
(o) TFRC, XIAP, PRAME, p27, Contig51037, ErbB3, DPYD, TERC, NME1, VEGFC; and
(p) CEGP1, PRAME, hENT1, XIAP, Contig51037, ErbB3, DPYD, NFKBp65, ID1, TS, including the use of intron-based sequences.

In another embodiment, the invention concerns gene expression analysis of a biological sample representative of ER-positive breast cancer based on determining the expression levels of the RNA transcripts or expression products of a gene or gene set selected from the group consisting of:
(a) PRAME, p27, IGFBP2, HIF1A, TIMP2, ILT2, CYP3A4, ID1, EstR1, DIABLO;
(b) Contig51037, EPHX1, Ki67, TIMP2, cyclinG1, DPYD, CYP3A4, TP, AIB1, CYP2C8;
(c) Bcl2, hENT1, FOXM1, Contig51037, cyclinG1, Contig46653, PTEN, CYP3A4, TIMP2, AREG;
(d) HIF1A, PRAME, p27, IGFBP2, TIMP2, ILT2, CYP3A4, ID1, EstR1, DIABLO;
(e) IGF1R, PRAME, EPHX1, Contig51037, cyclinG1, Bcl2, NME1, PTEN, TBP, TIMP2;
(f) FOXM1, Contig51037, VEGFC, TBP, HIF1A, DPYD, RAD51C, DCR3, cyclinG1, BAG1;
(g) EPHX1, Contig51037, Ki67, TIMP2, cyclinG1, DPYD, CYP3A4, TP, AIB1, CYP2C8;
(h) Ki67, VEGFC, VDR, GSTM3, p27, upa, ITGA7, rhoC, TERC, Pin1;
(i) CDC25B, Contig51037, hENT1, Bcl2, HLAG, TERC, NME1, upa, ID1, CYP;
(j) VEGFC, Ki67, VDR, GSTM3, p27, upa, ITGA7, rhoC, TERC, Pin1;
(k) CTSB, PRAME, p27, IGFBP2, EPHX1, CTSL, BAD, DR5, DCR3, XIAP;
(l) DIABLO, Ki67, hENT1, TIMP2, ID1, p27, KRT19, IGFBP2, TS, PDGFB;
(m) p27, PRAME, IGFBP2, HIF1A, TIMP2, ILT2, CYP3A4, ID1, EstR1, DIABLO;
(n) CDH1; PRAME, VEGFC; HIF1A; DPYD, TIMP2, CYP3A4, EstR1, RBP4, p27;
(o) IGFBP3, PRAME, p27, Bcl2, XIAP, EstR1, Ki67, TS, Src, VEGF;
(p) GSTM3, PRAME, p27, IGFBP3, XIAP, FGF2, hENT1, PTEN, EstR1, APC;
(q) hENT1, Bcl2, FOXM1, Contig51037, CyclinG1, Contig46653, PTEN, CYP3A4, TIMP2, AREG;
(r) STK15, VEGFC, PRAME, p27, GCLC, hENT1, ID1, TIMP2, EstR1, MCP1;
(s) NME1, PRAM, p27, IGFBP3, XIAP, PTEN, hENT1, Bcl2, CYP3A4, HLAG;
(t) VDR, Bcl2, p27, hENT1, p53, PI3KC2A, EIF4E, TFRC, MCM3, ID1;
(u) EIF4E, Contig51037, EPHX1, cyclinG1, Bcl2, DR5, TBP, PTEN, NME1, HER2;
(v) CCNB1, PRAME, VEGFC, HIF1A, hENT1, GCLC, TIMP2, ID1, p27, upa;
(w) ID1, PRAME, DIABLO, hENT1, p27, PDGFRa, NME1, BIN1, BRCA1, TP;
(x). FBXO5, PRAME, IGFBP3, p27, GSTM3, hENT1, XIAP, FGF2, TS, PTEN;
(y) GUS, HIA1A, VEGFC, GSTM3, DPYD, hENT1, EBXO5, CA9, CYP, KRT18; and
(z) Bclx, Bcl2, hENT1, Contig51037, HLAG, CD9, ID1, BRCA1, BIN1, HBEGF, including the use of intron-based sequences.

In a further embodiment, the cancer is breast cancer, and the gene(s) analyzed is/are selected from the group consisting of: FOXM1; PRAME; SKT15, Ki-67; CA9; NME1; SURV; TFRC; YB-1; RPS6KB1; Src; Chk1; CCNB1; Chk2; CDC25B; CYP3A4; EpCAM; VEGFC; hENT1; BRCA2; EGFR; TK1; VDR; Blc12; CEGP1; GSTM1; PR; BBC3; GATA3; DPYD; GSTM3; ID1; EstR1; p27; XIAP; IGF1R; AK055699; P13KC2A; TGFB3; BAGI1; pS2; WISP1; HNF3A; and NFKBp65.

In a still further embodiment, invention concerns gene expression analysis of a biological sample representative of invasive breast cancer, based on determining the expression levels of the RNA transcripts or expression products of a gene or gene set selected from the group consisting of:
(a) p53 BP2, Bcl2, BAD, EPHX1, PDGFRβ, DIABLO, XIAP, YB1, CA9, and KRT8;
(b) GRB7, CD68, TOP2A, Bcl2, DIABLO, CD3, ID1, PPM1D, MCM6, and WISP1;
(c) PR, p53BP2, PRAME, DIABLO, CTSL, IGFBP2, TIMP1, CA9, MMP9, and COX2;
(d) CD68, GRB7, TOP2A, Bcl2, DIABLO, CD3, ID1, PPM1D, MCM6, and WISP1;
(e) Bcl2, p53 BP2, BAD, EPHX1, PDGFRβ, DIABLO, XIAP, YB1, CA9, and KRT8;
(f) KRT14, KRT5, PRAME, p53BP2, GUS1, AIB1, MCM3, CCNE1, MCM6, and ID1;
(g) PRAME, p53 BP2, EstR1, DIABLO, CTSL, PPM1D, GRB7, DAPK1, BBC3, and VEGFB;
(h) CTSL2, GRB7, TOP2A, CCNB1, Bcl2, DIABLO, PRAME, EMS1, CA9, and EpCAM;
(i) EstR1, p53BP2, PRAME, DIABLO, CTSL, PPMLD, GRB7, DAPK1, BBC3, and VEGFB;
(j) Chk1, PRAME, p53BP2, GRB7, CA9, CTSL, CCNB1, TOP2A, tumor size, and IGFBP2;
(k) IGFBP2, GRB7, PRAME, DIABLO, CTSL, β-Catenin, PPM1D, Chk1, WISP1, and LOT1;
(l) HER2, p53BP2, Bcl2, DIABLO, TIMP1, EPHX1, TOP2A, TRAIL, CA9, and AREG;
(m) BAG1, p53 BP2, PRAME, IL6, CCNB1, PAI1, AREG, tumor size, CA9, and Ki67;
(n) CEGP1, p53BP2, PRAME, DIABLO, Bcl2, COX2, CCNE1, STK15, and AKT2, and FGF18;
(o) STK15, p53BP2, PRAME, IL6, CCNE1, AKT2, DIABLO, cMet, CCNE2, and COX2;
(p) KLK10, EstR1, p53BP2, PRAME, DIABLO, CTSL, PPM1D, GRB7, DAPK1, and BBC3;
(q) AIB1, p53BP2, Bcl2, DIABLO, TIMP1, CD3, p53, CA9, GRB7, and EPHXL
(r) BBC3, GRB7, CD68, PRAME, TOP2A, CCNB1, EPHX1, CTSL GSTM1, and APC;
(s) CD9, GRB7, CD68, TOP2A, Bcl2, CCNB1, CD3, DIABLO, ID1, and PPM1D;
(t) EGFR, KRT14, GRB7, TOP2A, CCNB1, CTSL, Bcl2, TP, KLK10, and CA9;
(u) HIF1α, PR, DIABLO, PRAME, Chk1, AKT2, GRB7, CCNE1, TOP2A, and CCNB1;
(v) MDM2, p53BP2, DIABLO, Bcl2, AIB1, TIMP1, CD3, p53, CA9, and HER2;
(w) MYBL2, p53BP2, PRAME, IL6, Bcl2, DIABLO, CCNE1, EPHX1, TIMP1, and CA9;
(x) p27, p53BP2, PRAME, DIABLO, Bcl2, COX2, CCNE1, STK15, AKT2, and ID1;
(y) RAD51, GRB7, CD68, TOP2A, CIAP2, CCNB1, BAG1, IL6, FGFR1, and p53BP2;
(z) SURV, GRB7, TOP2A, PRAME, CTSL, GSTM1, CCNB1, VDR, CA9; and CCNE2;

(aa) TOP2B, p53BP2, DIABLO, Bcl2, TIMP1, AIB1, CA9, p53, KRT8, and BAD;

(ab) ZNF217, GRB7, p53BP2, PRAME, DIABLO, Bcl2, COX2, CCNE1, APC4, and β-Catenin.

In a different embodiment, the invention concerns gene expression analysis of a biological sample, using intron-based polynucleotide sequences hybridizing to at least one genes selected from the group consisting of: CD68; CTSL; FBXO5; SURV; CCNB1; MCM2; Chk1; MYBL2; HIF1A; cMET; EGFR; TS; STK15, IGFR1; BC12; HNF3A; TP53BP2; GATA3; BBC3; RAD51C; BAG1; IGFBP2; PR; CD9; RB1; EPHX1; CEGP1; TRAIL; DR5; p27; p53; MTA; RIZ1; ErbB3; TOP2B; EIF4E, CD68; CTSL; FBXO5; SURV; CCNB1; MCM2; Chk1; MYBL2; HIF1A; cMET; EGFR; TS; and STK15.

Gene expression analysis may be performed in an array format, and the array preferably is a high-density array, comprising at least 100, more preferably at least 150, even more preferably, 200 sequences in a 5-10μ section.

BRIEF DESCRIPTION OF THE DRAWINGS

FIGS. 1A-M show masked intron sequences for the CEGP1, FOXM1, PRAME, and STK15 genes. Amplicons used for RT-PCR are shown in italics.

FIG. 2 shows primer/probe sets for CEGP1, FOXM1, PRAME, and STK15. Sequences of forward and reverse primers are indicated by "F" and "R," respectively. Sequences of primers are designated with "P."

FIG. 3 shows correlation coefficients [R] for co-expression of CEGP1 exon RNA with 47 other RNA sequences. Symbols: diamond=CEGP1 exon self vs. self (=1.0 by definition); squares=CEGP1 introns; triangles=sequences of other genes.

FIG. 6 shows an exemplary set of genes, the expression of which can be analyzed by the methods of the present invention.

DETAILED DESCRIPTION OF THE PREFERRED EMBODIMENT

A. Definitions

Figure 4:
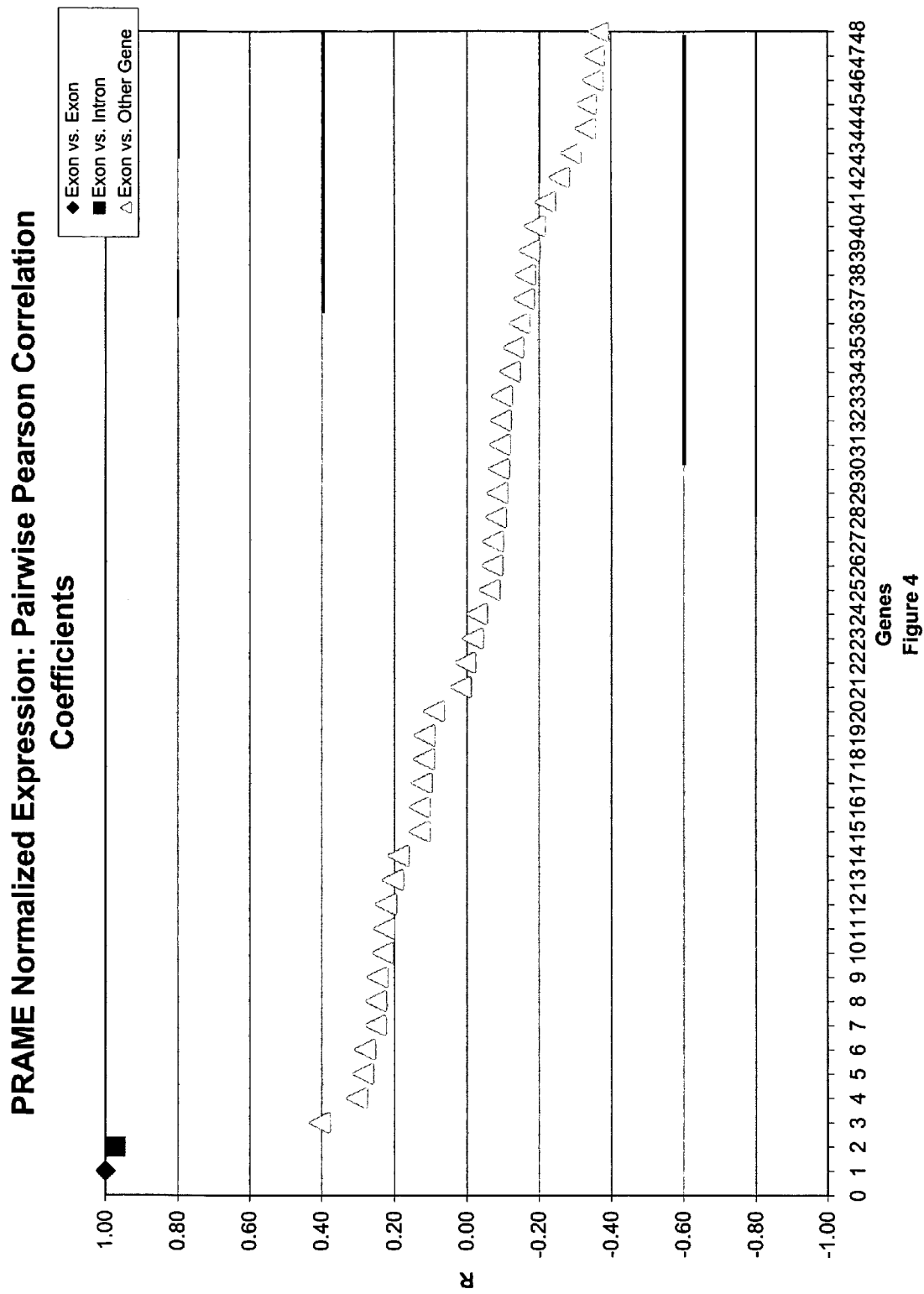
FIG. 4 shows correlation coefficients [R] for co-expression of PRAME exon RNA with 47 other RNA sequences. Symbols: diamond—PRAME exon self vs. self (=1.0 by definition); squares=PRAME introns; triangles=sequences of other genes.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the niRNA sequence of a gene as defined by Ref. Seq ID numbers. Operationally, intron sequences are the intervening sequences within the genomic DNA of a gene, bracketed by exon sequences and having GT and AG splice consensus sequences at their 5' and 3' boundaries.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is at a higher or lower level in one patient or test subject relative to another, for example, in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The term "normalized" with regard to a gene transcript or a gene expression product refers to the level of the transcript or gene expression product relative to the mean levels of transcripts/products of a set of reference genes, wherein the reference genes are either selected based on their minimal variation across, patients, tissues or treatments ("housekeeping genes"), or the reference genes are the totality of tested genes. In the latter case, which is commonly referred to as "global normalization", it is important that the total number of tested genes be relatively large, preferably greater than 50. Specifically, the term 'normalized' with respect to an RNA transcript refers to the transcript level relative to the mean of transcript levels of a set of reference genes. More specifically, the mean level of an RNA transcript as measured by Taq-Man® RT-PCR refers to the Ct value minus the mean Ct values of a set of reference gene transcripts.

The term "over-expression" with regard to an RNA transcript is used to refer to the level of the transcript determined by normalization to the level of reference mRNAs, which might be all measured transcripts in the specimen or a particular reference set of mRNAs.

The terms "expression threshold," and "defined expression threshold" are used interchangeably and refer to the level of a gene or gene product in question above which the gene or gene product serves as a predictive marker for patient response or resistance to a drug,. The threshold typically is defined experimentally from clinical studies. The expression threshold can be selected either for maximum sensitivity (for example, to detect all responders to a drug), or for maximum selectivity (for example to detect only responders to a drug), or for minimum error.

The phrase "gene amplification" refers to a process by which multiple copies of a gene or gene fragment are formed in a particular cell or cell line. The duplicated region (a stretch of amplified DNA) is often referred to as "amplicon." Often, the amount of the messenger RNA (mRNA) produced, i.e., the level of gene expression, also increases in the proportion of the number of copies made of the particular gene expressed.

The term "prognosis" is used herein to refer to the prediction of the likelihood of cancer-attributable death or progression, including recurrence, metastatic spread, and drug resistance, of a neoplastic disease, such as breast cancer. The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following sugery and/or termination of chemotherapy or other treatment modalities is likely.

The term "long-term" survival is used herein to refer to survival for at least 3 years, more preferably for at least 5 years, most preferably for at least 10 years following surgery or other treatment.

The term "increased resistance" to a particular drug or treatment option, when used in accordance with the present invention, means decreased response to a standard dose of the drug or to a standard treatment protocol.

The term "decreased sensitivity" to a particular drug or treatment option, when used in accordance with the present invention, means decreased response to a standard dose of the drug or to a standard treatment protocol, where decreased response can be compensated for (at least partially) by increasing the dose of drug, or the intensity of treatment.

"Patient response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation, dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in, 0.2×SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The term "housekeeping gene" refers to a group of genes that codes for proteins whose activities are essential for the maintenance of cell function. These genes are typically similarly expressed in all cell types. Housekeeping genes include, without limitation, glyceraldehyde-3-phosphate dehydrogenase (GAPDH), Cypl, albumin, actins, e.g. β-actin, tubulins, cyclophilin, hypoxantine phsophoribosyltransferase (HRPT), L32. 28S, and 18S.

According to the present invention, a polynucleotide or oligonucleotide molecule "corresponds to" a target sequence, such as an intron sequence or transcribed intronic RNA, if it incorporates or is complementary to such sequence.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Polymerase Chain Reaction (PCR)

The purpose of the polymerase chain reaction (PCR) is to make copies of a gene in order to provide larger amounts of nucleic acid for further use. PCR is a process based on a specialized polymerase enzyme (e.g. Taq DNA polymerase), which can synthesize a complementary strand to a given DNA strand in a mixture containing the four dNTP's (sATP, dCTP, dGTP, dTTP) and two oligonucleotide primers flanking the target sequence to be amplified. The two oligonucleotide primers are used to generate an amplicon typical of a PCR reaction. A third oligonucleotide, or probe, is designed to detect the nucleotide sequence located between the two PCR primers. Although the probe design might differ, in the Taq-Man® PCR method probe signals are controlled by the proximity of a reporter fluorescent dye and a quencher fluorescent dye. Any laser-induced emission from the reporter dye is quenched by the quenching dye when the two dyes are located close together as they are on the probe. During the amplification reaction, the polymerase enzyme (e.g. Taq DNA polymerase) cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The starting material for PCR can be DNA, cDNA, mRNA or any other polynucleotide that needs to be amplified. Since the PCR requires single-stranded DNA as template, if the starting material is double-stranded DNA, it needs to be denatured in order to produce single-stranded DNA.

As RNA cannot serve as a template for PCR, if the starting material is RNA, the first step is the reverse transcription of the RNA template into cDNA, followed by its exponential amplification in a PCR reaction. This version of PCR is generally referred to as reverse transcriptase PCR (RT-PCR). The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances. For example, RNA extracted from a tissue sample (e.g. FPET) can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. In this case, the probe is designed to be non-extendible by Taq DNA polymerase enzyme. TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescence signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs frequently used to normalize patterns of gene expression are mRNAs for the housekeeping genes glyceraldehyde-3-phosphate-dehydrogenase (GAPDH) and β-actin.

For further details of real time quantitative PCR see also Held et al., *Genome Research* 6:986-994 (1996). PCR is described in U.S. Pat. Nos. 4,683,202, 4,683,195; 4,965,188; and 5,075,216, the entire disclosures of which are hereby expressly incorporated by reference.

2. Introns and RNA Splicing

Most genes in higher eukaryotes contain more than 100,000 nucleotide pairs, some containing more than 2 million nucleotide pairs. This is significantly longer than the nucleotide sequence required to encode an average size protein (300-400 amino acids), which is in the order of about 1000 nucleotides. Most of the extra length consists of noncoding (intron) sequences that interrupt the coding (exon) sequences within the gene sequence. Most of higher eukaryotic genes coding for mRNA, tRNA and some coding for rRNA are interrupted by intron sequences. Genes for mRNA typically have 0 to 60 introns; while genes for tRNA typically include 0 or 1 intron.

When mRNA is transcribed from DNA, at first both exon and intron sequences are transcribed into the so-called heterogeneous nuclear RNA (hnRNA) or immature RNA or pre-mRNA. However, before the RNA exits the nucleus, intron sequences are often deleted from the transcribed mRNA as a result of a process known as RNA splicing. The process of intron removal involves a precise looping process controlled by a specific nucleotide sequence abutting the exons. Almost all introns can be identified by specific consensus sequences. The first two bases of an intron are always GU, while the last two bases are always AG, but the 5' and 3' splice sites typically have consensus sequences that extend beyond the GU and AG motifs. Splicing of mRNA takes place on a particle called spliceosome, while tRNA and rRNA are spliced by mechanisms that do not involve spliceosomes.

Introns are typically much longer than exons (sequences that are present in the mRNA). An average eukaryotic exon is about 150 nucleotides long, while a single human intron can be as long as close to 500,000 nucleotides, but typically are about 2000-4000 nucleotides. In general, a eukaryotic gene contains much more intron than exon sequences, as illustrated by the following table (Molecular Biology of the Cell, Bruce Alberts et al., eds., $3^{rd}$ edition, Garland Publishing Company, New York, N.Y., 1994, p. 340):

TABLE 1

| Gene | Gene Size ($\times 10^3$ nucleotides) | MRNA Size ($\times 10^3$ nucleotides) | Number of Introns |
|---|---|---|---|
| β-globin | 1.5 | 0.6 | 2 |
| Insulin | 1.7 | 0.4 | 2 |
| Proteinase C | 11 | 1.4 | 7 |
| Albumin | 25 | 2.1 | 14 |
| Catalase | 34 | 1.6 | 12 |
| LDL receptor | 45 | 5.5 | 17 |
| Factor VIII | 186 | 9 | 25 |
| Thyroglobulin | 300 | 8.7 | 36 |

In a particular embodiment of the present invention, intron sequences within a gene of interest are subjected to a selection process to identify intronic RNA sequence or sequences that co-express with exon RNA (i.e., mRNA) sequences of the same gene. Such selected intron sequences, the expression of which correlates with the expression of exon sequences, have especially desirable properties as potential diagnostic markers: (1) because of their favorable technical performance (specifically, optimizing assay specificity and sensitivity); and, (2) whatever biomedical importance attaches to the mRNA level of the gene is also attached to the cellular levels of intronic sequences. For example, high levels of an mRNA species that encodes a potent growth factor are likely to correlate with high rate of growth of a cell. Intronic sequences having cellular levels that correlate with mRNA levels of this same gene have the same likelihood to correlate with high growth rate of a cell. Such selected intronic sequences can then be used to screen valuable tissue specimens to search for clinical correlations and diagnostic, predictive or prognostic significance.

An exemplary process for selecting intron sequences that co-express with the mRNA of the same gene is as follows. Briefly, for any gene of interest, a set of relevant tissues from a population of patients of interest are assayed to measure the levels of a set of intronic and mRNA sequences. The intronic sequences found to have the highest Pearson correlation coefficient for co-expression with exon RNA (mRNA) sequences are then selected. The number of patients studied in this process is preferably at least above 50 and more preferably at least about 100.

In a specific example, the biomedical issue of interest regards patients with breast cancer and the gene of interest can be the tumor growth marker Ki-67. In this case, tumors from 50 or more breast cancer patients are used for measurement of Ki-67 mRNA levels and the levels of sequences from multiple Ki-67 introns, and the introns having the highest Pearson correlation coefficient for co-expressing with exon RNA are selected.

An advantage of this process is that the selection of the preferred intronic sequence can be carried out with tissue specimens that are relatively easily obtained and abundant (for example, specimens that lack valuable attached clinical records). Because such tissue can provide large amounts of RNA to screen, it will be possible to detect gene expression signals from even suboptimal probes. The highly sensitive and specific assays based on the selected intronic sequences then can be used to screen valuable tissue specimens, for example, specimens attached to important clinical information, such as disease recurrence, death, or response to defined therapeutic drugs or treatment regimens.

3. Gene Expression Profiling Using Intron-based PCR Primer/Probe Sets

At present, PCR primers and probes are designed based upon the mRNA or cDNA sequence, without considering the intron sequences. Indeed, introns are usually regarded as "packaging" material that is removed during splicing and generally rapidly degraded.

The present invention is based on the unanticipated experimental finding that intron RNAs can be readily detected by RT-PCR, even using highly degraded RNA from fixed, paraffin-embedded tissue specimens. In particular, it has been found that in gene expression profiling for a given gene RT-PCR signals from intron-based probe/primer sets can be as large, or larger, than the signals from exon-based RT-PCR signals. While this finding is supported by a few recent findings with certain mRNA species, it is not in accord with the prevailing view that introns are very rapidly degraded following splicing (Thomas et al., *J. Virol.* 76:532-40 [2002]; Clement et al., *J. Biol. Chem.* 276:16919-30 [2001]; Sharp et al., *Ann. Rev. Biochem.* 55:1119-1150 [1986]).

Also unexpectedly, the experimental findings underlying the present invention indicate that intronic RNA can be used for gene expression profiling, because the tissue amounts of expressed intron and exon sequences tend to be correlated. This result is unanticipated because scant or no evidence exists that the ratio of the overall rate constants for synthesis and turnover of transcribed intron and exon sequences are similar. In fact, the scientific literature provides evidence for the complexity of pre-mRNA and spliced intron turnover. For example, pre-mRNA can exist in multiple kinetic pools (Elliott and Rosbash, *Exp. Cell Res.* 229:181-8 [1996]), with subpopulations containing intron RNAs that are not efficiently spliced out and are transported to the cytoplasm in "immature" mRNA species, where they can decay at rates different than nuclear intron RNA sequences (Wang et al., *Proc. Natl. Acad. Sci. USA* 94:4360-5 [1997]). Evidence exists that certain spliced intron RNAs enter the cytoplasm in lariat structure (Clement et al., *RNA* 5:206-20 [1999]).

Finally, data presented here indicate that intron sequences can serve as diagnostic or prognostic molecular markers. Examining four mRNAs previously demonstrated to be prognostic in cancer, it is shown that their corresponding intron sequences are also prognostic, and in the same directions as the parent transcribed exon sequences (i.e., either positively or negatively prognostic).

In brief, the approach of the invention has been demonstrated as follows. Co-pending application Ser. No. 10/388,360, filed on Mar. 12, 2003 (PCT/US03/07713), the entire disclosure of which is hereby expressly incorporated by reference, describes a set of genes that predict likelihood of breast cancer recurrence. In that study, the levels of transcribed exon sequences in fixed paraffin-embedded breast cancer tissue specimens from 146 patients were measured by RT-PCR using exon-based PCR primer/probe sets. In the study described here, RT-PCR assays were created to measure the levels of transcribed intron sequences within four of the previously identified marker genes, and then used to screen RNA from 60 fixed paraffin-embedded biopsy specimens (representing 60 different patients, a subset of the patients evaluated in the previous study). The data presented in the examples below show that for each gene the introns and exons are co-expressed, and that the introns predict risk of disease recurrence as predicted by the previous exon-based data.

4. Design of Intron-Based PCR Primers and Probes

According to one aspect of the present invention, PCR primers and probes are designed based upon intron sequences present in the gene to be amplified. Accordingly, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N. J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: PCR *Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T.N. Primerselect: Primer and probe design. *Methods Mol. Biol.* 70:520-527 (1997), the entire disclosures of which are hereby expressly incorporated by reference.

5. Applications

The methods of the present invention, and specifically, the intron-based PCR primers and probes herein, utility in all fields where amplification of a nucleic acid (including RNA, DNA and, in general, all oligo- and poly nucleotides) representing a gene or a gene fragment is required. Thus the PCR primers and probes designed in accordance with the present invention can be used to amplify individual genes, or multiple genes present in a biological sample for the purpose of gene expression profiling by any methodology including, without limitation, gene expression profiling relying on quantitative PCR (e.g. quantitative RT-PCR), and microarray analysis, and bead-based assays.

For example, in a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at least 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Agilent's microarray technology.

An important aspect of the present invention is to use intron-based gene amplification as part of gene expression profiling to match patients to best drugs or drug combinations, and to provide prognostic information. For example, the measured expression of genes in cancer tissue (e.g. biopsied breast cancer tissue) can be used to predict the likelihood of long-term, disease-free survival of patients following surgery and/or other cancer therapy, or to predict patient response to a particular therapeutic approach. For this purpose it is typically necessary to correct for (normalize away) both differences in the amount of RNA assayed and variability in the quality of the RNA used. Therefore, the assays of the invention usually measure and incorporate the expression of certain normalizing genes, including well known reference genes, such as GAPDH and cyp1. Alternatively, normalization can be based on the mean or median signal (Ct) of all of the assayed genes or a large subset thereof (global normalization approach). On a gene-by-gene basis, the measured normalized amount of a patient tumor niRNA is compared to the amount found in a cancer, e.g. breast cancer tissue reference set. The number (N) of cancer, e.g. breast cancer, tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different fixed, paraffin-embedded (FPE) breast cancer tissue specimens. Unless noted otherwise, normalized expression levels for each mRNA/tested tumor/patient will be expressed as a percentage of the expression level measured in the reference set. More specifically, the reference set of a sufficiently high number (e.g., 40) tumors yields a distribution of normalized levels of each mRNA species. The level measured in a particular tumor sample to be analyzed falls at some percentile within this range, which can be determined by methods well known in the art.

In a Phase II study of gene expression in paraffin-embedded, fixed tissue samples of invasive breast carcinoma, the overexpression of any of the following genes in the breast cancer tissue was found to indicate a reduced likelihood of survival without cancer recurrence following surgery: FOXM1; PRAME; SKT15, Ki-67; CA9; NME1; SURV; TFRC; YB-1; RPS6KB1; Src; Chk1; CCNB1; Chk2; CDC25B; CYP3A4; EPCAM; VEGFC; hENT1; BRCA2; EGFR; TK1; VDR.

In the same study, the overexpression of any of the following genes in breast cancer indicates a better prognosis for survival without cancer recurrence following surgery: Blc12; CEGP1; GSTM1; PR; BBC3; GATA3; DPYD; GSTM3; ID1; EstR1; p27; XIAP; IGF1R; AK055699; P13KC2A; TGFB3; BAGl1; pS2; WISP1; HNF3A; NFKBp65.

In this same Phase II study of gene expression in paraffin-embedded, fixed tissue samples of ER-positive breast cancer, overexpression of the following genes was indicative of a reduced likelihood of survival without cancer recurrence following surgery: PRAME; FOXM1; EPHX1; HIF1A; VEGFC; Ki-67; VDR; NME1. Some of these genes (PRAME; FOXM1; VEGFC; Ki-67; VDR; and NME1) were also identified as indicators of poor prognosis in the previous analysis, not limited to ER-positive breast cancer. The overexpression of the remaining genes (EPHX1 and HIF1A) was found to be negative indicator of disease free survival in ER-positive breast cancer only. Overexpression of the following genes in ER-positive cancer was found to be indicative of a better prognosis for survival without cancer recurrence following surgery: Bcl-2; DIABLO; IGF1R; GSTM3. Of the latter genes, Bcl-2; IGFR1; and GSTM3 have also been identified as indicators of good prognosis in the previous analysis, not limited to ER-positive breast cancer. The overexpression of DIABLO appeared to be positive indicator of disease free survival in ER-positive breast cancer only. For further details see, co-pending application Ser. No. 60/427090, filed on Nov. 15, 2002, the entire disclosure of which is hereby expressly incorporated by reference.

The studies described above were performed essentially as described in Example 2 below, except gene amplification was studied using exon-based amplicons. For further details, see copending application Ser. No. 60/364,890 filed on Mar. 13, 2002, the entire disclosure of which is hereby expressly incorporated by reference. As attested by the data set forth in Example 2, the data obtained using intron-based amplicons show excellent correlation with the earlier data, and typically provide the added benefit of increased sensitivity.

The findings of the previous Phase II study of invasive breast ductal carcinoma were subjected to multivariate stepwise analysis, using the Cox Proportional Hazards Model using the following equation:

$$RR = \exp[\text{coef}(geneA) \times Ct(geneA) + \text{coef}(geneB) \times Ct(geneB) + \text{coef}(geneC) \times Ct(geneC) + \ldots].$$

In this equation, coefficients for genes that are predictors of beneficial outcome are positive numbers and coefficients for genes that are predictors of unfavorable outcome are negative numbers. The "Ct" values in the equation are $\Delta Ct$s, i.e. reflect the difference between the average normalized Ct value for a population and the normalized $\Delta Ct$ measured for the patient in question. The convention used in the analysis has been that ΔCts below and above the population average have positive signs and negative signs, respectively (reflecting greater or lesser mRNA abundance). The relative risk (RR) calculated by solving this equation indicated if the patient has an enhanced or reduced chance of long-term survival without cancer recurrence.

In a multivariate analysis, using an interrogation set including a reduced number of genes, the following ten-gene sets have been identified as having particularly strong predictive value of patient survival without cancer recurrence following surgical removal of primary tumor.

1. Bcl2, cyclinG1, NFKBp65, NME1, EPHX1, TOP2B, DR5, TERC, Src, DIABLO;
2. Ki67, XIAP, hENT1, TS, CD9, p27, cyclinG1, pS2, NFKBp65, CYP3A4;
3. GSTM1, XIAP, Ki67, TS, cyclinG1, p27, CYP3A4, pS2, NFKBp65, ErbB3;
4. PR, NME1, XIAP, upa, cyclinG1, Contig51037, TERC, EPHX1, ALDH1A3, CTSL;
5. CA9, NME1, TERC, cyclinG1, EPHX1, DPYD, Src, TOP2B, NFKBp65, VEGFC;
6. TFRC, XIAP, Ki67, TS, cyclinG1, p27, CYP3A4, pS2, ErbB3, NFKBp65.

In a multivariate analysis, using an interrogation set including all genes identified, the following ten-gene sets have been identified as having particularly strong predictive value of patient survival without cancer recurrence following surgical removal of primary tumor.

1. Bcl2, PRAME, cyclinG1, FOXM1, NFKBp65, TS, XIAP, Ki67, CYP3A4, p27;
2. FOXM1, cyclinG1, XIAP, Contig51037, PRAME, TS, Ki67, PDGFRa, p27, NFKBp65;
3. PRAME, FOXM1, cyclinG1, XIAP, Contig51037, TS, Ki6, PDGFRa, p27, NFKBp65;
4. Ki67, XIAP, PRAME, hENT1, contig51037, TS, CD9, p27, ErbB3, cyclinG1;
5. STK15, XIAP, PRAME, PLAUR, p27, CTSL, CD18, PREP, p53, RPS6KB1;
6. GSTM1, XIAP, PRAME, p27, Contig51037, ErbB3, GSTp, EREG, ID1, PLAUR;
7. PR, PRAME, NME1, XIAP, PLAUR, cyclinG1, Contig51037, TERC, EPHX1, DR5;
8. CA9, FOXM1, cyclinG1, XIAP, TS, Ki67, NFKBp65, CYP3A4, GSTM3, p27;
9. TFRC, XIAP, PRAME, p27, Contig51037, ErbB3, DPYD, TERC, NME1, VEGFC;
10. CEGP1, PRAME, hENT1, XIAP, Contig51037, ErbB3, DPYD, NFKBp65, ID1, TS.

Using the same multivariate analysis approach for ER-positive breast cancer, the following ten-gene sets have been identified as having particularly strong predictive value of patient survival without cancer recurrence following surgical removal of primary tumor.

1. PRAME, p27, IGFBP2, HIF1A, TIMP2, ILT2, CYP3A4, ID1, EstR1, DIABLO;
2. Contig51037, EPHX1, Ki67, TIMP2, cyclinG1, DPYD, CYP3A4, TP, AIB1, CYP2C8;
3. Bcl2, hENT1, FOXM1, Contig51037, cyclinG1, Contig46653, PTEN, CYP3A4, TIMP2, AREG;
4. HIF1A, PRAME, p27, IGFBP2, TIMP2, ILT2, CYP3A4, ID1, EstR1, DLABLO;
5. IGF1R, PRAME, EPHX1, Contig51037, cyclinG1, Bcl2, NME1, PTEN, TBP, TIMP2;
6. FOXM1, Contig51037, VEGFC, TBP, HIF1A, DPYD, RAD51C, DCR3, cyclinG1, BAG1;
7. EPHX1, Contig51037, Ki67, TIMP2, cyclinG1, DPYD, CYP3A4, TP, AIB1, CYP2C8;
8. Ki67, VEGFC, VDR, GSTM3, p27, upa, ITGA7, rhoC, TERC, Pin1;
9. CDC25B, Contig51037, hENT1, Bcl2, HLAG, TERC, NME1, upa, ID1, CYP;
10. VEGFC, Ki67, VDR, GSTM3, p27, upa, ITGA7, rhoC, TERC, Pin1;
11. CTSB, PRAME, p27, IGFBP2, EPHX1, CTSL, BAD, DR5, DCR3, XIAP;
12. DIABLO, Ki67, hENT1, TIMP2, ID1, p27, KRT19, IGFBP2, TS, PDGFB;
13. p27, PRAME, IGFBP2, HIF1A, TIMP2, ILT2, CYP3A4, ID1, EstR1, DIABLO;
14. CDH1; PRAME, VEGFC; HIF1A; DPYD, TIMP2, CYP3A4, EstR1, RBP4, p27;
15. IGFBP3, PRAME, p27, Bcl2, XIAP, EstR1, Ki67, TS, Src, VEGF;
16. GSTM3, PRAME, p27, IGFBP3, XIAP, FGF2, hENT1, PTEN, EstR1, APC;
17. hENT1, Bcl2, FOXM1, Contig51037, CyclinG1, Contig46653, PTEN, CYP3A4, TIMP2, AREG;
18. STK15, VEGFC, PRAME, p27, GCLC, hENT1, ID1, TIMP2, EstR1, MCP1;
19. NME1, PRAM, p27, IGFBP3, XIAP, PTEN, hENT1, Bcl2, CYP3A4, HLAG;
20. VDR, Bcl2, p27, hENT1, p53, PI3KC2A, EIF4E, TFRC, MCM3, ID1;
21. EIF4E, Contig51037, EPHX1, cyclinG1, Bcl2, DR5, TBP, PTEN, NME1, HER2;
22. CCNB1, PRAME, VEGFC, HIF1A, hENT1, GCLC, TIMP2, ID1, p27, upa;
23. ID1, PRAME, DIABLO, hENT1, p27, PDGFRa, NME1, BIN1, BRCA1, TP;
24. FBXO5, PRAME, IGFBP3, p27, GSTM3, hENT1, XIAP, FGF2, TS, PTEN;
25. GUS, HIA1A, VEGFC, GSTM3, DPYD, hENT1, FBXO5, CA9, CYP, KRT18;
26. Bclx, Bcl2, hENT1, Contig51037, HLAG, CD9, ID1, BRCA1, BIN1, HBEGF.

In view of the excellent correlation between exon-based and intron-based gene expression profiling results (see Example 2), the same gene sets are expected to have similar prognostic value when gene expression profiling is based on the quantitation of RT-PCR signals from intron-based primer/probe sets.

Further details of the invention will be apparent from the following non-limiting examples.

EXAMPLE 1

Design and Use of Intron-Specific PCR Primer/Probe Sets

RNA was extracted from formalin-fixed, paraffin-embedded (FPET) breast cancer biopsy specimens (Clinomics Biosciences Inc., Pittsfield, MA) as follows. Three 10 μm sections were cut and placed in a 1.5 ml tube. Paraffin was removed by xylene extraction (1 ml, 3 times) followed by ethanol wash (1 ml, twice). RNA was isolated from sectioned tissue blocks using the MasterPure™ Purification kit (Epicentre, Madison, Wis). RNA was quantitated by the RiboGreen Fluorescence method (Molecular Probes). Twenty FPET RNA samples were then pooled and used as described below.

First-strand cDNA was synthesized using Qiagen's Omniscript Reverse Transcriptase with pooled gene specific primers (reverse primers shown in FIG. 2) random hexamers and RNase Inhibitor, using pooled FPET RNA (400 ng). A no reverse transcriptase (RT) reaction was also performed with 150 ng of pooled FPET RNA, sufficient RNA to perform the Taqman amplification at 5 ng/well.

TABLE 2

| Reagents | RT Vol (µl) | No RT Vol (µl) | Final conc |
|---|---|---|---|
| 10X Buffer RT | 4 | 2 | 1X |
| dNTP mix, 5 mM each dNTP | 4 | 2 | 500 µM each |
| ABI Random hexamer, 50 µM | 1 | 0.5 | 1.25 µM |
| GSP pool, 1 µM | 2 | 1 | 50 nM |
| ABI RNase Inhibitor, 20 U/µl | 1 | 1 | 20 U/rxn |
| Omniscript RT, 4 U/µl | 2 | 0 | 8 U or 0 U/rxn |
| Nuclease free water | 10 | 5.5 | |
| Pooled FPET RNA (164 ng/µl) | 16 | 8 | 65.6 ng/µl |
| Total vol | 40 | 20 | |

Reaction conditions: 37° C., 60 min, 93° C., 5 min

TaqMan Assay

TaqMan assays for the 48-gene panel were carried out in triplicate wells with reaction volume of 25 µl and RNA input of 5 ng per assay. A "no RT" reaction for each gene was carried out in a single well as a control to verify that RNA rather than DNA signals were being measured. Real time quantitation was performed on the ABI 7700 using the following parameters:

Cycling conditions: 95° C., 10 min for one cycle, 95° C., 20 sec followed by 60° C., 45 sec, 40 cycles.

Volume reaction: 25 µl.

Dye layer setting: FAM, (the passive reference is ROX)

Results

Intron specific Taqman primer-probe sets were designed based on masked introns of CEGP1, FOXM1, PRAME and STK15.genes, To delineate intron sequences within the genes, the NCBI reference sequence for each mRNA (NM_XXXXXX) was aligned to the human genome using the BLAST-like alignment tool (BLAT) program available at the University of Santa Cruz on-line genome resource site (http://genome.ucsc.edu). Intron sequences were then searched for repetitive sequences using the Repeat Masker program available on-line through the Baylor College of Medicine (http://searchlauncher.bcm.tmc.edu/seq-util/seg-util.html). Repeat sequences, such as Alu repeats, are identified by this program and masked. It is important to exclude these sequences prior to designing primer-probes because they yield strong, non-specific signals. The masked intron sequences (FIGS. 1A-M) were then used to design Taqman primer-probe sets using Primer Express (ABI). Other programs suitable for primer-probe sets include, for example, the newer primer probe design program for MGB assays-by-design (ABI). The amplicons for each primer-probe set are delineated in bold font in FIG. 1. Each specific primer-probe set is shown in FIG. 2.

The intron-specific primer-probe sets (test genes) were used together with their corresponding exon-specific primer-probe set (references gene) in standard Taqman gene expression profile experiments using pooled FPET RNA. Normalized expression was calculated by the formula $2^{\Delta Ct}$ where $\Delta Ct$ is the difference between the Cts of the test gene primer-probe set and the reference gene primer-probe sets [Ct (reference)–Ct (test)].

EXAMPLE 2

A Phase II Study of Gene Expression in Premalignant and Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival.

Study Design

Molecular assays were performed on paraffin-embedded, formalin-fixed primary breast tumor tissues obtained from 60 individual patients diagnosed with breast cancer. All patients underwent surgery with diagnosis of invasive carcinoma of the breast. Patients were included in the study only if histopathologic assessment, performed as described in the Materials and Methods section, indicated adequate amounts of tumor tissue and homogeneous pathology.

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, all tumor blocks were subjected to the same characterization, as described above, and the block most representative of the pathology was used for analysis.

Gene Expression Analysis mRNA was extracted and purified from fixed, paraffin-embedded tissue samples, and prepared for gene expression analysis as described above.

Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for expression of 48 different RNA sequences representing products of 37 different genes. The threshold cycle (Ct) values for each patient were normalized based on the median of all genes for that particular patient. Clinical outcome data were available for all patients from a review of registry data and selected patient charts.

Outcomes were classified as:

| | | |
|---|---|---|
| 0 | died due to breast cancer or to unknown cause or alive with breast cancer recurrence; |
| 1 | alive without breast cancer recurrence or died due to a cause other than breast cancer |

Analysis was performed by:

Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

For each gene a Cox Proportional Hazards model (see, e.g. Cox, D. R., and Oakes, D. (1984), *Analysis of Survival Data*, Chapman and Hall, London, N.Y.) was defined with time to recurrence or death as the dependent variable, and the expression level of the gene as the independent variable. The genes that have a p-value <0.05 in the Cox model were identified. For each gene, the Cox model provides the relative risk (RR) of recurrence or death for a unit change in the expression of the gene. One can choose to partition the patients into subgroups at any threshold value of the measured expression (on the Ct scale), where all patients with expression values above the threshold have higher risk, and all patients with expression values below the threshold have lower risk, or vice versa, depending on whether the gene is an indicator of poor (RR>1.01) or good (RR<1.01) prognosis. Thus, any threshold value will define subgroups of patients with respectively increased or decreased risk.

Table 3, below, shows pairwise correlation of expression (presented by correlation coefficients) between the tested introns and exons for the genes CEGP1, FOXM1, PRAME, and STK15. For two of the four genes, CEGP1 and PRAME, introns were found that yielded correlation coefficients [for co-expression with their respective exons] above 0.90. In the case of STK15, one intron correlated with exon expression with a correlation coefficient ~0.80. For FOXM1, intron:exon expression correlations were significantly lower. In this last case, however, it seems likely that actual expression may be highly correlated but not detectable for a technical reason. Expression of the FOXM1 exon in many patients was beneath the detection threshold of the assay, which potentially prevents detection of high correlations that may exist. If this hypothesis is correct, FOXM1 introns would still register as negative clinical prognostic markers as previously demonstrated for FOXM1. As shown later, this result occurs.

Figure 5:
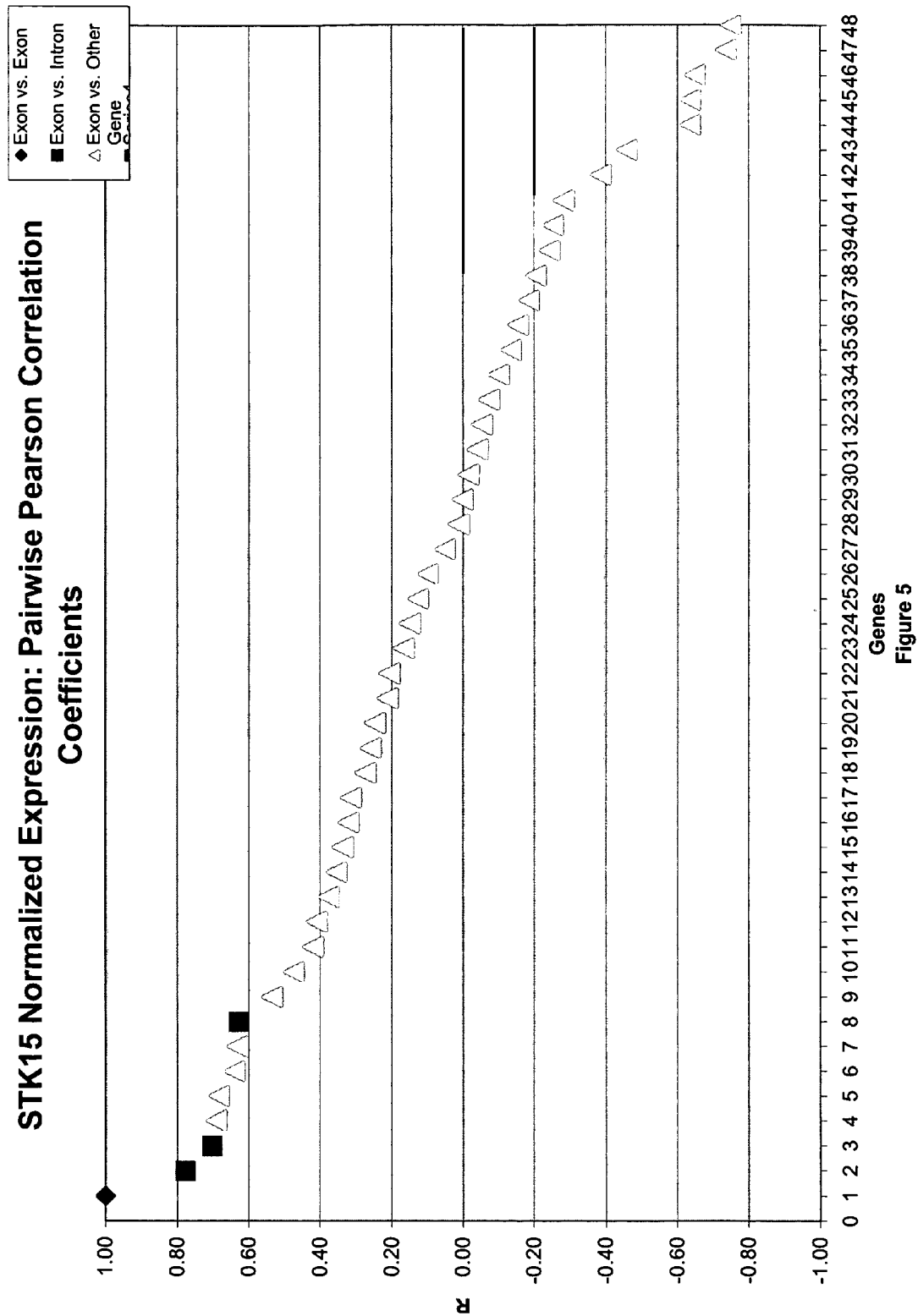
FIG. 5 shows correlation coefficients [R] for co-expression of STK15 exon RNA with 47 other RNA sequences. Symbols: diamond—STK15 exon self vs. self (=1.0 by definition); squares=STK15 introns; triangles=sequences of other genes.

FIGS. 3, 4 and 5 show that the pairwise correlation of expression of the tested RNAs against CEGP1, PRAME and STK15 exon RNAs. As shown, respective introns of these genes yielded the highest correlations. It is noteworthy that the panel of 48 genes included genes that we selected, by several bioinformatics-based strategies, as particularly likely to correlate in expression with CEGP1, PRAME, STK15, and FOXM1. Those non-intron-based strategies were most successful in the case of STK15, as several candidate genes had expression correlation coefficients in the range of 0.6-0.7.

TABLE 3

Correlations between Intron and Exon Expression for Four Genes

ExpressionCorrelation Coefficient {R}

|  | CEGP1intron1.1 | CEGP1intron3.1 | CEGP1intron4.1 | CEGP1intron5.1 | CEGP1.2 |
|---|---|---|---|---|---|
| CEGP1intron1.1 | 1.00 |  |  |  |  |
| CEGP1intron3.1 | 0.89 | 1.00 |  |  |  |
| CEGP1intron4.1 | 0.97 | 0.82 | 1.00 |  |  |
| CEGP1intron5.1 | 0.91 | 0.87 | 0.88 | 1.00 |  |
| CEGP1.2 | 0.91 | 0.80 | 0.90 | 0.87 | 1.00 |

|  | FOXM1intron3.3 | FOXM1intron5.1 | FOXM1intron7.1 | FOXM1.1 |
|---|---|---|---|---|
| FOXM1intron3.3 | 1.00 |  |  |  |
| FOXM1intron5.1 | 0.48 | 1.00 |  |  |
| FOXM1intron7.1 | 0.54 | 0.73 | 1.00 |  |
| FOXM1.1 | 0.44 | 0.33 | 0.38 | 1.00 |

|  | STK15intron1.1 | STK15intron2.1 | STK15intron4.1 | STK15.2 |
|---|---|---|---|---|
| STK15intron1.1 | 1.00 |  |  |  |
| STK15intron2.1 | 0.78 | 1.00 |  |  |
| STK15intron4.1 | 0.69 | 0.74 | 1.00 |  |
| STK15.2 | 0.63 | 0.70 | 0.78 | 1.00 |

|  | PRAMEintron2.1 | PRAME.3 |
|---|---|---|
| PRAMEintron2.1 | 1.00 |  |
| PRAME.3 | 0.97 | 1.00 |

Table 4, below, shows the impact upon patient survival of expression of CEGP1, FOXM1, PRAME, and STK15, exons and introns. The parent exons all had statistically significant impact on relative risk [RR], as we previously determined, except in the case of FOXM1. Because the present study evaluated 60 patients from the original 146 patient group, the FOXM1 marker may have fallen from significance because the statistical hazard of examining a reduced data set. Very notably, for all four tested genes, intron expression significantly impacted RR, and in the same direction as the parent exons.

TABLE 4

Cox Model Results for 60 Patients with Breast Cancer

Prognostic Correlations

| Gene | Coef | RR = exp(coef) | se(coef) | z | p |
|---|---|---|---|---|---|
| CEGP1.2 | −0.202 | 0.817 | 0.050 | −4.024 | 0.00006 |
| CEGP1intron1.1 | −0.329 | 0.720 | 0.087 | −3.771 | 0.00016 |
| CEGP1intron3.1 | −0.261 | 0.770 | 0.078 | −3.335 | 0.00085 |

TABLE 4-continued

Cox Model Results for 60 Patients with Breast Cancer

| | Prognostic Correlations | | | | |
|---|---|---|---|---|---|
| Gene | Coef | RR = exp(coef) | se(coef) | z | p |
| CEGP1intron4.1 | −0.275 | 0.760 | 0.073 | −3.774 | 0.00016 |
| CEGP1intron5.1 | −0.312 | 0.732 | 0.082 | −3.817 | 0.00014 |
| FOXM1.1 | 0.175 | 1.192 | 0.136 | 1.289 | 0.19700 |
| FOXM1intron3.3 | 0.304 | 1.355 | 0.120 | 2.523 | 0.01160 |
| FOXM1intron5.1 | 0.514 | 1.673 | 0.195 | 2.639 | 0.00832 |
| FOXM1intron7.1 | 0.546 | 1.726 | 0.182 | 2.993 | 0.00276 |
| PRAME.3 | 0.125 | 1.133 | 0.054 | 2.294 | 0.02180 |
| PRAMEintron2.1 | 0.125 | 1.133 | 0.052 | 2.397 | 0.01650 |
| STK15.2 | 0.692 | 1.998 | 0.201 | 3.450 | 0.00056 |
| STK15intron1.1 | 0.357 | 1.429 | 0.149 | 2.400 | 0.01640 |
| STK15intron2.1 | 0.391 | 1.479 | 0.154 | 2.536 | 0.01120 |
| STK15intron4.1 | 0.410 | 1.506 | 0.133 | 3.084 | 0.00204 |

A common perception exists that steady state levels of transcribed exon sequences greatly exceed those of transcribed intron sequences (Sharp et al. *Ann. Rev. Biochem.* 55: 1119-50 [1986]). Nevertheless, our examination of CEGP1, FoxM1, PRAME and STK15 exon and intron expression, using TaqMan[TM] RT-PCR to assay RNA from fixed paraffin-embedded breast cancer tissue, demonstrated that intron and exon signal intensities were in the same range, and in all cases in the useful detection range of the assay [data not shown]. The detection of intronic RNA in this study is all the more notable because the tissue used was fixed in formalin, which degrades RNA, and thus substantially limits the ability to detect RNA (T. E. Godfrey et al. *J. Mol. Diag.* 2: 84-91 [2000]). In the case of CEGP1 three of the tested introns yielded lower signals and one a higher signal than the exon. In the case of FOXM1, five of nine tested introns yielded higher signals than the exon. In the case of PRAME signal intensities from the tested intron and exon were nearly identical. Finally, for STK15 all introns had signal intensities that were ¼ to 1/20 those of the exon, but were still in the useful range of the assay. Thus, these results indicate that steady state levels of expressed introns are adequate for use of intron RNAs as molecular markers.

All references cited throughout the disclosure, including the examples, are hereby expressly incorporated by reference for their entire disclosure.

While the present invention has been described with reference to what is considered to be specific embodiments, it is to be understood that the invention is not so limited. To the contrary, the invention is intended to cover various modifications and equivalents included within the spirit and scope of the appended claims. For example, while the disclosure includes various breast cancer-associated genes and gene sets, similar genes and gene sets and methods concerning other types of cancer are specifically within the scope herein.

---

SEQUENCE LISTING

<160> NUMBER OF SEQ ID NOS: 67

<210> SEQ ID NO 1
<211> LENGTH: 1566
<212> TYPE: DNA
<213> ORGANISM: Homo sapiens
<220> FEATURE:
<221> NAME/KEY: misc_feature
<222> LOCATION: (802)...(1027)
<223> OTHER INFORMATION: n= a, t, c, or g
<220> FEATURE:
<221> NAME/KEY: misc_feature
<222> LOCATION: (1126)...(1518)
<223> OTHER INFORMATION: n= a, t, c, or g
<220> FEATURE:
<221> NAME/KEY: intron
<222> LOCATION: (0)...(0)
<223> OTHER INFORMATION: MGB-CEGP1 int 1.1

<400> SEQUENCE: 1

```
gtgagtgtcc ggccgcgggg gcgcacctgg cacagcaggc agggccagga agagtgttta      60
ggtccccggc ggagtccaga gccggcgcg cggggctcgg ggctggcggc tgcagctccg     120
cgggggcctc tgctccccc gggacctcac ccgccggccg ggccaaggcg ccacgaccgc     180
tggggccctg agtccttcgg cccggcctcg gaccggagc tgctgacggt tcccgccccg     240
gtccggatgc ctccagagcg cctgctagtc agaccgtcgc cggcgagcag gcaggagggt     300
gcggaccctg gccttggggt cccgcgcctc agcgtaggcg gggaaactga gggccgggcc     360
gggcacatcc gcgaggcggt ggcagctttg ccgtttcttt ctttgggggc cggcaagttc     420
tgctgatggc ttcggggtgg gctccagaga cttttctgtc agcggaacag cgcctgttcc     480
gatctgggaa ttaccctgaa gcagcaacaa gcctaggttt tcagcagaga actttggttt     540
ccagagagga ctctggacgt gctgtgctta ctggacttgc aatactttca aaatgctttt     600
```

-continued

```
gtttttaatt aatatcctgg agtagtgtca acccaggaaa tacttctgcc aaggcgggtt    660
tccaggttga gaggatgggc aggggtggga gtgcagggggg ccggccatgg ggacaccatc   720
cccgcttcgc agcatctgag agccctggat gacatctgct ccgatcccgg ggcagacttc   780
ccataaatac tctaaaccag cnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnctc tgagctccga gaaagctgac agacagctgc ttggtgttca gagcttgtct   1080
gtccgtttgg tcctttcctc ctttagcggg catgtaggta ctattnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnca catggcctgg gagcctgtac caggtgtcag ctgtgctctt   1560
ttgcag                                                              1566

<210> SEQ ID NO 2
<211> LENGTH: 4985
<212> TYPE: DNA
<213> ORGANISM: Homo sapiens
<220> FEATURE:
<221> NAME/KEY: misc_feature
<222> LOCATION: (83)...(253)
<223> OTHER INFORMATION: n= a, t, c, or g
<220> FEATURE:
<221> NAME/KEY: misc_feature
<222> LOCATION: (1975)...(2296)
<223> OTHER INFORMATION: n= a, t, c, or g
<220> FEATURE:
<221> NAME/KEY: misc_feature
<222> LOCATION: (2445)...(2468)
<223> OTHER INFORMATION: n= a, t, c, or g
<220> FEATURE:
<221> NAME/KEY: misc_feature
<222> LOCATION: (2499)...(2551)
<223> OTHER INFORMATION: n= a, t, c, or g
<220> FEATURE:
<221> NAME/KEY: misc_feature
<222> LOCATION: (4295)...(4352)
<223> OTHER INFORMATION: n= a, t, c, or g
<220> FEATURE:
<221> NAME/KEY: intron
<222> LOCATION: (0)...(0)
<223> OTHER INFORMATION: MGB-CEGP1 int 3.1

<400> SEQUENCE: 2
gtacctctgc ccagctgtgg atgggggcag agccacatct gagaccctct cccttgcacg     60
cgcacacaca cactgactct agnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnatcttta catagaatac atttcaaaca tgactagatg tctcaggagc    300
aatatagtgg atgatctgcc aagttttttca aaaaggtgct gaaaaccaca gcaccagtat    360
gagcctgctc cctgctctgg gtgggtaggg aggaggctgg atccttccca tgcagacttt    420
```

```
caatgaagtg ccctgttttc agccccaagc tagatccggc ccttccatgt tttgcatttt      480
tgagctccga ggggcagaag ggctccctcc ctggactttc cgtgctgtgg tttccttcgc      540
ctacgtcacc atttatcatt cctctgtaaa tttgccggaa actcttctct tctgatgtcc      600
ttctcttcat tctctttgct ttgagtttat accttttttc attcctctgt tacttagtag      660
attcttgaga ggaaggggca ttaagtacat gtggccaatc agttattttt aactgaatgt      720 catccttta actcttccct gctctttctt aagctaaaga gtcacatttt ggtggctgtg       780
ttcctcttgg agttgcatct gcctattttt aggggaagtg ccctaaatac tagcctatta      840 accccttttgg ccatgtgctg cttattcttt cccattactt aagaatgagg tcattttaat    900
ttcttctact atttaatcac aaatttatag attgttttaa tcctggtctt ggtaactttt      960
caagggtttc ttcatggaag atgattttg tctcattttc caaggatggc agctcacacc      1020
ttatacttaa ctagaatacc tgtttgggta ccaagaaaaa ttgtcagagg aaccccagg      1080 ggccaatggg tttgatggct atcatcaccc agagcctgct cattctcagc gtttggggcg     1140
gggaagtcac acatactggc tttgatcagg cagatttcct atcttgtgcc aggtgtggcc     1200
cttgataaag tagcagttgg gtttcatttt cctgccaggt tctctggggt cattggtgtg     1260
ccctgcactc ttgtccaatg taggccaaat tcgagatggg aatgaattag gaggccagtg     1320
gcacagagtg atccgaatct cagggcatct ctccttttga ttgctcaaag ctgcttcctg     1380
ggaagtcact ttggcttcct ctgcaggtgg ctggggaggg atgtgggaac tgcaggttaa     1440
agccatcgct tgagccctca cggtctgggt cccacccagt tacaaagcag ctggtagcga     1500
ttaagatcac ctcttatccc tgtacttcca gagccctggc tcagccccac tctcccctcc     1560
tgcaagcccc cggactgatt agagacacag gctcctcata ccagaagcaa atacaaatgc     1620
agttcctttc tgcaaactgt gttttctaaa ttttctacaa ttcagacatt cttggatccc     1680
ctaaagagta tttgaagtga acattttgt ctggaactaa aaccaaaatc taagaatttg      1740
cgttgtggtc tggaagtgct ctctgtgatt ttctgttgtg tttcaacctg attgcttggc     1800
aaattcatgg gagtgtcagc caacagatta tagcaattgg taacgagaa cctttgcatc      1860 ctagggtttt gattcttcaa atagaacagc ctgtaaaaag ttttcttcta ggatttcctc     1920
tctgatatgc acattaaact ctatgaaact gtaggcttaa aaaccacag tggtnnnnnn      1980 nnnnnnnnnn nnnnnnnnnn nnnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn     2100
nnnnnnnnnn nnnnnnnnnn nnnnnnnnnn nnnnnnnnnn nnnnnnnnnn nnnnnnnnnn     2160
nnnnnnnnnn nnnnnnnnnn nnnnnnnnnn nnnnnnnnnn nnnnnnnnnn nnnnnnnnnn     2220
nnnnnnnnnn nnnnnnnnnn nnnnnnnnnn nnnnnnnnnn nnnnnnnnnn nnnnnnnnnn     2280
nnnnnnnnnn nnnnnnccac agtggatacc ttcaaagtga ttaaaagaag gtaacacagg     2340
aagctagtat tttctattgc tgttgttttt aataattatt taccaaatgt tctttaatat     2400
agggcatcat aatcattgac tctgagggaa agctcaagat actgnnnnnn nnnnnnnnnn     2460
nnnnnnnncc ttagagactc caaagctgtg ataaagagnn nnnnnnnnnn nnnnnnnnnn     2520
nnnnnnnnnn nnnnnnnnnn nnnnnnnnnn ncccggcccg cctttgttcc tattcatggg     2580
tgctcaggct ctcagaatga gcactcctct tttgttttgt gtgttctgag aatatttaga     2640
tggtgtactg atgcctttc agggcaacag ggaaggtgtc agggtggcaa agtggaggct      2700
gtgctttcag caggacctgt tacccgtttt atgtcatgtt ttcctcccaa ttcacaaggc     2760
```

```
atatttttgt ttggtttcca gaaataatct tcagtggagc cctgatcttg gggtgcacca    2820
gaatggggga tttccaatgt ttctgagctg tttcccttct ggtgaacgaa ccatcctgga    2880
cgtgacaacc agaccaattt tggaaagagc tagggccatt tgctgggctg cctagtttgg    2940
aacagattaa tctgctcacc ccagcagtgg tcttgcatta agtcagagtg ctacaaaggc    3000
tttgaggtca cttcttgaaa agctgtcagc gtttccagag ccatttaagt ctctattatg    3060
tcttggtaac ttcaggtgta gcttgatgtg gtaggacatt aggtggtagg ttctctgtgt    3120
atcacaatgg catctggcat acaggcattc ttacgaaata tttcttgtgt aggtgaatta    3180
ctctgaggca gtaaaggtca cttttgcaaat gtcttaacag tcttgtaaac agagtgaaaa    3240
agcagcagca gctggcctgt ttgggagtgt actttccagg tgttcctgcc cccatttctt    3300
gggcagtatt atatttaccc ccgagcacta gttacttccc atgctcggct gacccaagga    3360
caaacacaac gctttctggg ccttctcaga caggacactg cttctagagg cagctgtcac    3420
ctcccgcgcc atctcagtac tggggtgcaa atcacatctt cggaattacc agccagagca    3480
agagaaagct ttccaccaat ccagtgcaag tctctttctg tgttaattga cagccaccct    3540
tggcatggat gaatgaatcc cagcaaccag cagactgagt gctggagtgc aggcagctca    3600
taactgtcag gcaaaagagc aagagggttt taagagagac tccagaaagt atgggatata    3660
ttaacccttg cactgtcttc tggaatagga atgacatctg tttgtattaa acaattgtt    3720
ccgtttaagc acagtttgac agctctggag tgggagctgg agagagaact ttgacttcac    3780
tagaacctgt tggctaaggt tttaggggca caatatagaa gggtgttgga ttctagagaa    3840
gtgaaagcaa cctttttgta ctcgtgttga aaacagtgcc ctactagtat tagagtgtct    3900
cattgataga gagccaatga caaccaagtc cctactctca gagatgtttt agagttacat    3960
tgcacgaatg caaagaagca acataggaac aggtaattaa taataaagta taaactgagc    4020
agatgtcttg aaagtattct agggtatgaa aagaattcct tcaggatgct ggtaggcagc    4080
aggatctcaa agaattagtt ttgagatgag gcagaatgct ggtaaaccac acgggcagtt    4140
accttgctgt gccccctcat ttagatgtgt gccgagccct gcaagaacag aagcagctgt    4200
tccccttccc accatcatac tacaaggtta agcctaatca gaatttactg tatacctcaa    4260
aaaaattgta cagcagctac cacacacgag cacannnnnn nnnnnnnnnn nnnnnnnnnn    4320
nnnnnnnnnn nnnnnnnnnn nnnnnnnnnn nngttcttgt tgctgttgct gtgtgatgct    4380
gtcagaggct tatgccctga gggagggatc aagggagtgg ctgagggtgg tcacagaaga    4440
cagattccgg ggcatgtggc ccgtacgagg atgccaaaat gccacagtca cactcacctc    4500
agaagggtgg gattggtggg ggcagagagg ggcgttgaaa tgttttgaaa attatcttca    4560
agagtatgtg aaaaaattga gaatcttgat cattctatct gaacattttc ttaggaggat    4620
tctccttttc tctttacatt cttgatcagc tcttgggtaa agacatggca gagataagag    4680
cgtgagtacc agttcctggg gtcagcaggc tctgatcctg catgcaatag agagctccag    4740
tgtattggga aggctcccaa ctcgttagga gagttgagac atcgtatctc ttgggtgaca    4800
gaataaattt ttcatgtcta ttaattggcc taggttgact ttaatgacat atactttca    4860
aatgtggggc tgatggagac ctaagcagac agatctgtgg gccacccctt agccctttgc    4920
cgctctccca gggctcagga ttctgaccac agcctagtca cctgtcgcac actgctgttt    4980
ttcag                                                                4985

<210> SEQ ID NO 3
<211> LENGTH: 2556
```

```
<212> TYPE: DNA
<213> ORGANISM: Homo sapiens
<220> FEATURE:
<221> NAME/KEY: misc_feature
<222> LOCATION: (507)...(743)
<223> OTHER INFORMATION: n= a, t, c, or g
<220> FEATURE:
<221> NAME/KEY: misc_feature
<222> LOCATION: (1584)...(1678)
<223> OTHER INFORMATION: n= a, t, c, or g
<220> FEATURE:
<221> NAME/KEY: misc_feature
<222> LOCATION: (2428)...(2474)
<223> OTHER INFORMATION: n= a, t, c, or g
<220> FEATURE:
<221> NAME/KEY: intron
<222> LOCATION: (0)...(0)
<223> OTHER INFORMATION: MGB-CEGP1 int 4.1

<400> SEQUENCE: 3
gtaagtatgg gccagtgcac acctgccatg ggaaccgtcg tattccacag gctgccttct      60
gtggcccagc tcagaagcac cacctcatgg cacggctgca gcagcaggga aggcagttag     120
cacgggatac cgacctctac caagtacttg ttcactgcag aagggtggtc tcccttaggg     180
aagggaaatg atattttaaa aaggaactca tcaggaggaa atgaaattca ggagtaagga     240
gtgtgaatgt tggggggcag ttctccctgt tcccacagaa taaaaccaaa tgtcctcatc     300
tggcaatcac agctctttgc caccaggtcc tgcttcccct ataaacctca tctgcctcct     360
ttccgcagac actactcccc ttgcctttgg agaacagccc aaatcctttg atgcctccag     420
gcctttccca agccctcctg ccttcctggc gtggtggact ctcactcaac cttcaatatt     480
ctgtttaact tctaataagg ataagcnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnccatcct ctgctatcag aagcctcctg ggtgcttcag     780
acagggcagc catcttgtac tttggctccc acagcacttt cctcagctgt atagctctgg     840
gttgacttgt gtgttgatgt gtctgtctcc ccaggtatga gccccctcca agtcagggac     900
cttgcctcat ttttcctctc agtcctcccc tggtacctgc tatgggatat gctcagtaca     960
cttgtgttta atgagtgggt aaatgggtgg cctacaccat cgggccgcag ctcctgcacc    1020
acgattgtag taacaaaact ccacctggga acaggaaacc actggcaatt catggtgttc    1080
ctaaaccacg atttatgcca ggggaagcac tgaggagttc cctttaggaa ccttcccaaa    1140
gccatggaca gaagacccct gccatttggt ggggatggtg gtttatggtg agtaggagat    1200
gaggggacag tttcactggt gagggacttc tctccattgt ctccctcaca aagcagactg    1260
ccaccccaaa gctgtccaag ccaaggctgg tgccaccatc acactcaagc aacaggttct    1320
gacatgctct tagggcccct cgaagtcagg ctgtccctga gggcttccag tgagctagca    1380
gagtggagac cattttccca cctccagatc ttcggaagga agaccagac cctccaagac     1440
tcacctgcgg ggcgagaccc tcaacatttc atagtctttc agggaacagt tgctgaaggg    1500
ggcgggggg tgggcacctg taagcttgtt tttaaagatt ttaaatgtct ttaagatatc     1560
actgctcaaa taatattgtt ctgnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnncg    1680
tttgaggaat taacaaagaa aaaaactaag acctagaatc tcaccacata accagctgtt    1740
```

-continued

```
tcaatttttc catattccta tttagttgtt gttcatatgc atacacaatt tttacatagc    1800
tataatcaca ggacaacaca aatatgtaat tagttctttt gaattagaaa aattacaaag    1860
ggcctatgta aaatgcaaac actccaaagc atataaagaa acatgcagt ttcccgcctc    1920 ccgtttccct tgccagaggt aaccacggtt agcagtttga tgaatagata gttttgtagt    1980 tggcttttt tcttttggc ctatcatcaa tacattcata tatagtcttg ataattacca    2040
gttactgtca cgttaattgt gtgcagaatc atcctgtgat tatccttcct tctaactaat    2100
ctagattgaa tctgatgaga gaaattctga catatatgta caaattaaat attgtctgtt    2160
ttattccagc ataaagtgct atagcatttc ccaaagcccc agtacagctg tattaatagg    2220
taaacttctc tagatagaac aaagcagtag tctagaatct cttggtataa tttcccttat    2280
ataataaaag tctctccccc aactctccca tctccctctt cctgtatgac tttgtttaaa    2340
cccatgtttc agcatttcta caatttgtat tgtaactatc tgcatacaca gacaccacag    2400
ggtctgactt ggagttatgt ctttcgtnnn nnnnnnnnn nnnnnnnnn nnnnnnnnn      2460 nnnnnnnnnn nnnnaatcag aatttctctg gagcaaacac agccctgtgt tgtggaaat    2520 ctcagtgctt tatgtattga ttcattttgc tgtcag                             2556
```

<210> SEQ ID NO 4
<211> LENGTH: 716
<212> TYPE: DNA
<213> ORGANISM: Homo sapiens
<220> FEATURE:
<221> NAME/KEY: intron
<222> LOCATION: (0)...(0)
<223> OTHER INFORMATION: MGB-CEGP1 int 5.1

<400> SEQUENCE: 4

```
gtgagtggca accccaacac tgagtgaggg tctgcaccag cctgcctgtc cctaccccta     60
ccccttaatg gtgtttagca cagatgcagg ctgtttcctg tgcatttgcc cccccagcag    120
gccctgtgct gcttcgcatg ctacagtggg agtggtctag gcctgtgggg aaggcccctc    180
tctccctgtg tgaccttggg aagcccttcc tcctctcctg gactaggctg ctcctaacgc    240
tggtattcca gagactggca caacacctcc caggaggcca gggcagcacg aagttagagc    300 tgttataat gatgcggcac ttctggccag caggagccag ggccgtatat ttctggcggg    360
atgcctgcct tgcccttcac ggtgtgtcct tcactagctc catttagag gtttccaggc    420 ccaaggctct ttttctcctc gactcagggg actgaagctt gcattcccta gtgtctcttt    480
ggtcagtgca atatacctcc aaaatctttt ccatgtttaa tgtttgctaa ggatctgtgg    540
ccctttaacg ggctgtgtct cccacagagc ctcattacaa cacatttta ttgcgtgaac    600 agagtcacat atctttcatt cctcttatgt ctgggatttc agcaaacaca gttgtatggg    660
gatgagcaat ctaactcatt cagtctgaga accgtgctct tttgcttctc ttgtag       716
```

<210> SEQ ID NO 5
<211> LENGTH: 2041
<212> TYPE: DNA
<213> ORGANISM: Homo sapiens
<220> FEATURE:
<221> NAME/KEY: misc_feature
<222> LOCATION: (559)...(869)
<223> OTHER INFORMATION: n= a, t, c, or g
<220> FEATURE:
<221> NAME/KEY: misc_feature
<222> LOCATION: (888)...(1052)
<223> OTHER INFORMATION: n= a, t, c, or g
<220> FEATURE:
<221> NAME/KEY: misc_feature
<222> LOCATION: (1102)...(1380)
<223> OTHER INFORMATION: n= a, t, c, or g
<220> FEATURE:
<221> NAME/KEY: misc_feature
<222> LOCATION: (1393)...(1692)
<223> OTHER INFORMATION: n= a, t, c, or g
<220> FEATURE:
<221> NAME/KEY: intron
<222> LOCATION: (1841)...(1907)
<223> OTHER INFORMATION: FOXM1 int 3.2
<220> FEATURE:
<221> NAME/KEY: intron
<222> LOCATION: (1871)...(1936)
<223> OTHER INFORMATION: FOXM1 int 3.1

<400> SEQUENCE: 5

| | | | | | |
|---|---|---|---|---|---|
| gtaatgtgtc | ccacagcaac | caaaatcaag | gtcagcccag | cctgacagtc | tctccagtgc | 60 |
| tgtactgcaa | cttgtatctg | ggacagcagt | taagtgcaaa | ggacactaga | atgataaaca | 120 |
| aatgtatctt | ttagattgtg | actcaatctt | attgaatcca | gcaaaatca | ttaagaagag | 180 |
| ctccttaact | acttcatgtg | ttactaccta | aagtccatgg | agggtcttca | atgtagcact | 240 |
| caagcccact | tttctgctac | actcaacagc | cgtcctagat | gccagcagct | agagtggcta | 300 |
| agtagtttta | tgaaaatgtc | ttgattaaaa | aaaaaaatgc | tgtctgtgag | cctcatgacc | 360 |
| caagatgtca | tctcctgtag | cgtcacatag | catttctagt | gggcagggggt | tttccttttca | 420 |
| cttcattcat | ggaaagaccg | agatgcctgt | gagtcaacat | agctcacgca | gttggtcggt | 480 |
| gtcagagcca | caaatgaggt | cttctgacgg | gtgctcaatt | ccaagtcaag | tgtgctttgt | 540 |
| tttcctcatg | gtagaactcn | nnnnnnnnnn | nnnnnnnnnn | nnnnnnnnnn | nnnnnnnnnn | 600 |
| nnnnnnnnnn | nnnnnnnnnn | nnnnnnnnnn | nnnnnnnnnn | nnnnnnnnnn | nnnnnnnnnn | 660 |
| nnnnnnnnnn | nnnnnnnnnn | nnnnnnnnnn | nnnnnnnnnn | nnnnnnnnnn | nnnnnnnnnn | 720 |
| nnnnnnnnnn | nnnnnnnnnn | nnnnnnnnnn | nnnnnnnnnn | nnnnnnnnnn | nnnnnnnnnn | 780 |
| nnnnnnnnnn | nnnnnnnnnn | nnnnnnnnnn | nnnnnnnnnn | nnnnnnnnnn | nnnnnnnnnn | 840 |
| nnnnnnnnnn | nnnnnnnnnn | nnnnnnnnnc | ctcatggtag | aactatgnnn | nnnnnnnnnn | 900 |
| nnnnnnnnnn | nnnnnnnnnn | nnnnnnnnnn | nnnnnnnnnn | nnnnnnnnnn | nnnnnnnnnn | 960 |
| nnnnnnnnnn | nnnnnnnnnn | nnnnnnnnnn | nnnnnnnnnn | nnnnnnnnnn | nnnnnnnnnn | 1020 |
| nnnnnnnnnn | nnnnnnnnnn | nnnnnnnnnn | nncatggtag | aactttaat | tttactcccct | 1080 |
| tccatcagct | tactttccta | gnnnnnnnnn | nnnnnnnnnn | nnnnnnnnnn | nnnnnnnnnn | 1140 |
| nnnnnnnnnn | nnnnnnnnnn | nnnnnnnnnn | nnnnnnnnnn | nnnnnnnnnn | nnnnnnnnnn | 1200 |
| nnnnnnnnnn | nnnnnnnnnn | nnnnnnnnnn | nnnnnnnnnn | nnnnnnnnnn | nnnnnnnnnn | 1260 |
| nnnnnnnnnn | nnnnnnnnnn | nnnnnnnnnn | nnnnnnnnnn | nnnnnnnnnn | nnnnnnnnnn | 1320 |
| nnnnnnnnnn | nnnnnnnnnn | nnnnnnnnnn | nnnnnnnnnn | nnnnnnnnnn | nnnnnnnnnn | 1380 |
| ttaatttcct | agnnnnnnnn | nnnnnnnnnn | nnnnnnnnnn | nnnnnnnnnn | nnnnnnnnnn | 1440 |
| nnnnnnnnnn | nnnnnnnnnn | nnnnnnnnnn | nnnnnnnnnn | nnnnnnnnnn | nnnnnnnnnn | 1500 |
| nnnnnnnnnn | nnnnnnnnnn | nnnnnnnnnn | nnnnnnnnnn | nnnnnnnnnn | nnnnnnnnnn | 1560 |
| nnnnnnnnnn | nnnnnnnnnn | nnnnnnnnnn | nnnnnnnnnn | nnnnnnnnnn | nnnnnnnnnn | 1620 |
| nnnnnnnnnn | nnnnnnnnnn | nnnnnnnnnn | nnnnnnnnnn | nnnnnnnnnn | nnnnnnnnnn | 1680 |
| nnnnnnnnnn | nntaattccc | tagtttctta | atttctctga | gccaccttttc | ttgctattga | 1740 |
| tcactacctc | acagccttac | tctgcttttc | tagcccctga | cagctatcta | ggtcttttct | 1800 |
| ttatcacaat | ctaaggttgg | catcagtctt | tattcccgta | gaatagatgg | gtttatggct | 1860 |

```
gaaggtgacg gctctgcggt gtggagtgtc aggagagttg ccaagagggc tgcaaagaca    1920
ccagacgaag cctgtgctga gcacagtggg aggggcctga ggctggtttc cccatgtgtt    1980
tgaagggtga tgtttctgaa tctaaagtag ctgataacca gttgtcttgc tcttcttcca    2040
g                                                                     2041
```

<210> SEQ ID NO 6
<211> LENGTH: 993
<212> TYPE: DNA
<213> ORGANISM: Homo sapiens
<220> FEATURE:
<221> NAME/KEY: intron
<222> LOCATION: (52)...(124)
<223> OTHER INFORMATION: FOXM1 int 4.1
<220> FEATURE:
<221> NAME/KEY: intron
<222> LOCATION: (110)...(185)
<223> OTHER INFORMATION: FOXM1 int 4.2
<220> FEATURE:
<221> NAME/KEY: misc_feature
<222> LOCATION: (249)...(397)
<223> OTHER INFORMATION: n= a, t, c, or g
<220> FEATURE:
<221> NAME/KEY: misc_feature
<222> LOCATION: (442)...(749)
<223> OTHER INFORMATION: n= a, t, c, or g

<400> SEQUENCE: 6

```
gtgaatgccc tgctttcctc taaatagggc ctaagttgga ggttgtcata gccatctcaa      60
aaggaaacaa gttctgctag tgatgctttc atttgatcag gggagagtta gaagccagcc     120
acccaattag tgacttgcac aaaacccagt gaattaagta cacttgacaa ataccaaatg     180
acacattttt gtgccagacc agagcaagga gaaggctgtt ctgacccaac agaaagggct     240
ccccagggnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnntac aagaaattct gggaatgctt     420
gctctaaaaa aagcccttcc tnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnng cctgccttag gctggagacc agaagctgag     780
ctaccagaac gtcttttcag aaagaagtta ttttggtttt tcagagtgcc cataaggctg     840
ctggtagctg taaccattct cctgggaggg gcagttgtct ggggtgtctt ttgtcatcag     900
tcaggaataa gtgttttttcc caatccggtc aaattgacca cgttggtggt aacttcatct     960
catttctctc ccacaatgcc tggccgccac cag                                  993
```

<210> SEQ ID NO 7
<211> LENGTH: 602
<212> TYPE: DNA
<213> ORGANISM: Homo sapiens
<220> FEATURE:
<221> NAME/KEY: intron
<222> LOCATION: (0)...(0)
<223> OTHER INFORMATION: FOXM1 int 5.1

<400> SEQUENCE: 7

```
gtaaggttct ttccctctgg ctcggggctt ggccttgttt tcctttcact gctcagcatg      60
```

-continued

```
gctttagtgg acagagacaa gatgtgatgt ggggaagggt ccctatggcc atgttttgtc    120
taggtgccag ccctagacac agaacaccct gagggtcagg cacacaccca cttccctccc    180
cttccatggg catcacaagg gcacactgag cagagcaggg cacagcaggg gagcatgctg    240
cagcagccac aagcgcatgg caccagcctc aggggcggca gttcgttcgc tcacttttgt    300
gcctagcttt tctttgccac gcatatagct acctgctctg gcatccccca ggggtgttga    360
ggacacgtgg gtgaagcggt agtgccactc tgccatcatg tgtctgtagg ccacccacct    420
gcccactcat cacagttttg gagactgctc gcctacgtcc atcccctcag gttggcctcc    480
tctctctggg ctgtcattaa ctcaagcaca caccaccaga gcagctggtg gggttttgcc    540
atcccctctt taccttattg tgttaacata ggtttctttc tctccccatc tgccacaagc    600
ag                                                                    602

<210> SEQ ID NO 8
<211> LENGTH: 4656
<212> TYPE: DNA
<213> ORGANISM: Homo sapiens
<220> FEATURE:
<221> NAME/KEY: intron
<222> LOCATION: (0)...(0)
<223> OTHER INFORMATION: FOXM1 int 7.1
<220> FEATURE:
<221> NAME/KEY: misc_feature
<222> LOCATION: (316)...(615)
<223> OTHER INFORMATION: n= a, t, c, or g
<220> FEATURE:
<221> NAME/KEY: misc_feature
<222> LOCATION: (626)...(930)
<223> OTHER INFORMATION: n= a, t, c, or g
<220> FEATURE:
<221> NAME/KEY: misc_feature
<222> LOCATION: (1044)...(1259)
<223> OTHER INFORMATION: n= a, t, c, or g
<220> FEATURE:
<221> NAME/KEY: misc_feature
<222> LOCATION: (1452)...(1802)
<223> OTHER INFORMATION: n= a, t, c, or g
<220> FEATURE:
<221> NAME/KEY: misc_feature
<222> LOCATION: (2085)...(3116)
<223> OTHER INFORMATION: n= a, t, c, or g
<220> FEATURE:
<221> NAME/KEY: misc_feature
<222> LOCATION: (3138)...(3433)
<223> OTHER INFORMATION: n= a, t, c, or g
<220> FEATURE:
<221> NAME/KEY: misc_feature
<222> LOCATION: (3442)...(3728)
<223> OTHER INFORMATION: n= a, t, c, or g
<220> FEATURE:
<221> NAME/KEY: misc_feature
<222> LOCATION: (3814)...(4081)
<223> OTHER INFORMATION: n= a, t, c, or g
<220> FEATURE:
<221> NAME/KEY: misc_feature
<222> LOCATION: (4289)...(4371)
<223> OTHER INFORMATION: n= a, t, c, or g

<400> SEQUENCE: 8
gtgggtgtcc tattttcctc tgaagagaga ttctggccaa ttaagaatgt tggaccttca     60
gcttgcaaag cactctgata agtgttcctt gagagcttat aaatctagtt gggtagaaaa    120
ggcataaaaa catagggaag tgtaatagca ttagaagagc taaaaaggta tttggattac    180
aatgtaagtg gtgtcagaag gcccataaat acctgatgag cttgtaagaa ttcagacaaa    240
agtgattgtg atagatgggc taggattatt aaggaagata cacaagggag gcaggcctta    300
```

```
gaaagagatg gatttnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnngtgga tttgannnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn gtagatttgg gtaagcaaac aggtgtagag      960
agagcatgct aatgggcagt gccatggagg cgggaaatgc agttcgtacc tggcagtagt     1020
aaagtgactg ggtcagacta actnnnnnnn nnnnnnnnnn nnnnnnnnnn nnnnnnnnnn     1080
nnnnnnnnnn nnnnnnnnnn nnnnnnnnnn nnnnnnnnnn nnnnnnnnnn nnnnnnnnnn     1140
nnnnnnnnnn nnnnnnnnnn nnnnnnnnnn nnnnnnnnnn nnnnnnnnnn nnnnnnnnnn     1200
nnnnnnnnnn nnnnnnnnnn nnnnnnnnnn nnnnnnnnnn nnnnnnnnnn nnnnnnnng     1260
tctagcttga ggggaaggtg agaagggtaa attcagagcc aacttggatc agccatcaga     1320
tctgcactta acactgttaa agggttctgt gagtacgggc tgacatgtaa ccaaagtgaa     1380
aagcttcccc catcccttc agagagatga aaatagcata gagtctggag tttagagcga      1440
cttgggtttg cnnnnnnnnn nnnnnnnnnn nnnnnnnnnn nnnnnnnnnn nnnnnnnnnn     1500
nnnnnnnnnn nnnnnnnnnn nnnnnnnnnn nnnnnnnnnn nnnnnnnnnn nnnnnnnnnn     1560
nnnnnnnnnn nnnnnnnnnn nnnnnnnnnn nnnnnnnnnn nnnnnnnnnn nnnnnnnnnn     1620
nnnnnnnnnn nnnnnnnnnn nnnnnnnnnn nnnnnnnnnn nnnnnnnnnn nnnnnnnnnn     1680
nnnnnnnnnn nnnnnnnnnn nnnnnnnnnn nnnnnnnnnn nnnnnnnnnn nnnnnnnnnn     1740
nnnnnnnnnn nnnnnnnnnn nnnnnnnnnn nnnnnnnnnn nnnnnnnnnn nnnnnnnnnn     1800
nncatattac acacaaaatt ataccacaca tacataattt agcgtaaatt cattcatgtg     1860
gccgtagcat gtgccctgtt tgggttttca tgcagtgggt tttctcccct ttcctttttg     1920
gctccctctc caccctacca tcacccacat caccccctact cccaagataa ctggttgata    1980
atttatgatg cttcttgca tattttatca atgctcttag ttatactata catgtatagc      2040
gatagccatt ttatatgtac acatacaaca cacagaacat tgatnnnnnn nnnnnnnnnn     2100
nnnnnnnnnn nnnnnnnnnn nnnnnnnnnn nnnnnnnnnn nnnnnnnnnn nnnnnnnnnn     2160
nnnnnnnnnn nnnnnnnnnn nnnnnnnnnn nnnnnnnnnn nnnnnnnnnn nnnnnnnnnn     2220
nnnnnnnnnn nnnnnnnnnn nnnnnnnnnn nnnnnnnnnn nnnnnnnnnn nnnnnnnnnn     2280
nnnnnnnnnn nnnnnnnnnn nnnnnnnnnn nnnnnnnnnn nnnnnnnnnn nnnnnnnnnn     2340
nnnnnnnnnn nnnnnnnnnn nnnnnnnnnn nnnnnnnnnn nnnnnnnnnn nnnnnnnnnn     2400
nnnnnnnnnn nnnnnnnnnn nnnnnnnnnn nnnnnnnnnn nnnnnnnnnn nnnnnnnnnn     2460
nnnnnnnnnn nnnnnnnnnn nnnnnnnnnn nnnnnnnnnn nnnnnnnnnn nnnnnnnnnn     2520
nnnnnnnnnn nnnnnnnnnn nnnnnnnnnn nnnnnnnnnn nnnnnnnnnn nnnnnnnnnn     2580
nnnnnnnnnn nnnnnnnnnn nnnnnnnnnn nnnnnnnnnn nnnnnnnnnn nnnnnnnnnn     2640
nnnnnnnnnn nnnnnnnnnn nnnnnnnnnn nnnnnnnnnn nnnnnnnnnn nnnnnnnnnn     2700
```

| | |
|---|---|
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnngtta | 3120 |
| tcaatttgtg agagctcnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |
| nnnnnnnnnn nnnnnnnnnn nnnnnnnnnn nnnnnnnnnn nnnnnnnnnn nnnnnnnnnn | 3420 |
| nnnnnnnnnn nnntgtgaga gnnnnnnnnn nnnnnnnnnn nnnnnnnnnn nnnnnnnnnn | 3480 |
| nnnnnnnnnn nnnnnnnnnn nnnnnnnnnn nnnnnnnnnn nnnnnnnnnn nnnnnnnnnn | 3540 |
| nnnnnnnnnn nnnnnnnnnn nnnnnnnnnn nnnnnnnnnn nnnnnnnnnn nnnnnnnnnn | 3600 |
| nnnnnnnnnn nnnnnnnnnn nnnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnncc ctgtgagagc tctttgttgt taaaataatc ttctttcttt tatgctgaag | 3780 |
| atatttttct acttctattg tttatctctt tacnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |
| nnnnnnnnnn nnnnnnnnnn nnnnnnnnnn nnnnnnnnnn nnnnnnnnnn nnnnnnnnnn | 4080 |
| ntgtttgttg tttcttaact ttgtttatgg tatctcttgc cacagtaaaa ttttaaagtt | 4140 |
| ttatgtagtc aaatgtctct cttctctttt acagtttctg ggtttccagt cttggttaag | 4200 |
| aaggtcaccc gcaccctcag attgtatatg tagtctccta gattctcttt caggatttgt | 4260 |
| atgattttaa ggttttcatt tttttttan nnnnnnnnnn nnnnnnnnnn nnnnnnnnnn | 4320 |
| nnnnnnnnnn nnnnnnnnnn nnnnnnnnnn nnnnnnnnnn nnnnnnnnnn ntaaggttct | 4380 |
| tattttcatg cattaaatct tgtatacag tgtaagacaa gcatgcaatt ttatttcctc | 4440 |
| tcggatgaat gctattataa ttatgccact acatactaca tacccgcatc ttttaccccc | 4500 |
| agaattgaac taccaacttc aacatacatc gtattctcat atttaataga ttttaagact | 4560 |
| tcaaaacgac acaaagagga tcagaacccg tatgtgatat ttttgtgcgt cctgtctggt | 4620 |
| gaccgttggt tcaccttatc tctgtttccc tttcag | 4656 |

<210> SEQ ID NO 9
<211> LENGTH: 614
<212> TYPE: DNA
<213> ORGANISM: Homo sapiens
<220> FEATURE:
<221> NAME/KEY: intron
<222> LOCATION: (0)...(0)
<223> OTHER INFORMATION: MGB-PRAME int 2.1

<400> SEQUENCE: 9

```
gtaagttcga gccctgattc ctccgcttcc ccgcagggtg accttgggct tgtgccccg     60 gcaccacccc tgtcccgggt ccctgttttc tctctggaaa tgggttgaag accaaagaaa   120
ataatgtgcg ccacttgggt caccccgggc cgcctgcccc ggaaaattgg ccccagttga   180
ggagttgtgg ctgtaaggat gccttgaacc gaggcggcgg tgctcgtggt tggagctctc   240
cagggtgggt gcgcatttgt aatgcggtgg atgctctggg actcggcccc tctgaaggtg   300
ctgggggttg gggacggccc aggcagtggc gtaggcgtcc taggaaggcg ggagcagagg   360
cagaaatgtc gctgcaagac cgtagtcagg gtccttgacc acagggtca  cttgtgacca   420 accacatggt ctgttgttcc tcctgccccc tggttcagcc caggaaacac tggtgctcag   480
gtttggagcc agagatttgc actgaaaggg cgggattgag tcgccagttg tcagtttcct   540
cagcagtatt tgcggaggtt ttcacaggag gccgttgctt cgtaaatatt atacatgtat   600
tcttcttttt ggag                                                    614

<210> SEQ ID NO 10
<211> LENGTH: 432
<212> TYPE: DNA
<213> ORGANISM: Homo sapiens
<220> FEATURE:
<221> NAME/KEY: intron
<222> LOCATION: (0)...(0)
<223> OTHER INFORMATION: MGB-PRAME int 4.1

<400> SEQUENCE: 10
gtaagggtga cctagcagct tggtgtgggg ccctgggaac ctgagcagga tgcagctggg    60
gtcagggagc atggagcgcc taaggctggg ccagaggctc tgatggttgc cagcaaggaa   120
gttcagggag gccttggggc tactgcaggg gtcactcttg gaatgggctt ctggacatgg   180
ggcactgatt aaaatgcaga ggtgtctgaa ggaacatgca cctgcttcct cctggtgggg   240
tgggaattgg ggaccaggaa ggatcccagg atcctagtgg gaaagggagc agctgatgcc   300
tgaagtacga agtaaaagtg cagatctaag gtggatgtct gtttggttct tacctacatt   360
atgagactca tggtcttatt ttgagttgat cttaaagcat catctcagct aattacctgt   420
ttttccccac ag                                                      432

<210> SEQ ID NO 11
<211> LENGTH: 3740
<212> TYPE: DNA
<213> ORGANISM: Homo sapiens
<220> FEATURE:
<221> NAME/KEY: intron
<222> LOCATION: (0)...(0)
<223> OTHER INFORMATION: MGB-STK15 int 1.1
<220> FEATURE:
<221> NAME/KEY: misc_feature
<222> LOCATION: (84)...(151)
<223> OTHER INFORMATION: n= a, t, c, or g
<220> FEATURE:
<221> NAME/KEY: misc_feature
<222> LOCATION: (321)...(491)
<223> OTHER INFORMATION: n= a, t, c, or g
<220> FEATURE:
<221> NAME/KEY: misc_feature
<222> LOCATION: (537)...(615)
<223> OTHER INFORMATION: n= a, t, c, or g
<220> FEATURE:
<221> NAME/KEY: misc_feature
<222> LOCATION: (853)...(894)
<223> OTHER INFORMATION: n= a, t, c, or g
<220> FEATURE:
<221> NAME/KEY: misc_feature
<222> LOCATION: (1259)...(1309)
<223> OTHER INFORMATION: n= a, t, c, or g
```

<220> FEATURE:
<221> NAME/KEY: misc_feature
<222> LOCATION: (1337)...(2516)
<223> OTHER INFORMATION: n= a, t, c, or g
<220> FEATURE:
<221> NAME/KEY: misc_feature
<222> LOCATION: (2521)...(3567)
<223> OTHER INFORMATION: n= a, t, c, or g

<400> SEQUENCE: 11

```
gtacaaggggg tttgttgagt ggtgttgaca tgcgcgggag gggtgggtgg gcttcagatt      60
ggattttgtc ctccgagatc accnnnnnnn nnnnnnnnnn nnnnnnnnnn nnnnnnnnnn     120
nnnnnnnnnn nnnnnnnnnn nnnnnnnnnn nggtaagcgt acggagaact tgcagctggg     180
gtgggtgtta cagaggaaaa gcaggagtgc ggtttaacgg gggccgcttt agatagaata     240
gcctaagaag gcccttgtcc tggctggatg agtgggtgaa ttgatgaatg agaacctcct     300
tgcagaggcc ttcccggtcc nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn ngggatgcag accggtgcat acaaatcgtc tggggacgtt aaaatgnnnn     540
nnnnnnnnnn nnnnnnnnnn nnnnnnnnnn nnnnnnnnnn nnnnnnnnnn nnnnnnnnnn     600
nnnnnnnnnn nnnnncactg tccttaactc tcgtaatgtc tcttcctctt ccgtaacctt     660
ccttgtccct tgaattaaac gttttcagc aacctactca gttcgtcctt cccttcatct     720
ctgcagacat gcacaggtct gagggaggaa ggaataaacc gtataaacct cctgcgctat     780
tagcctaaca gcttttctat tcaaaatagt aggacttctg gtttgaactg aatggatcct     840
gtgaaagtca tcnnnnnnnn nnnnnnnnnn nnnnnnnnnn nnnnnnnnnn nnnnagtctc     900
cttggcgttg tctccagaat tctggattag aatcttattc cattctgctt gttattcaat     960
ttccctagaa agaaaggtag aataaattgg agcaaatgcc tgtagcttct gtcagaagaa    1020
tgttgaataa atgttgttag gcctatgtga tctcattaga ctgctactta gaattgtaag    1080
ggaagtaaag cattagagca tgtgtgaaat taaatatttg attaacacaa gtgtgcattt    1140
ccttgttgct gtttatcaac ttttacttac ccactgtttt tttataaggg ctgcagcctg    1200
tagtctgggc ctggcttcat catggaatta tttgcttaat tgtaaaatgg taatcttaan    1260
nnnnnnnnnn nnnnnnnnnn nnnnnnnnnn nnnnnnnnnn nnnnnnnnng gatatttgat    1320
aagaaacttc agtgaannnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
```

```
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnggga    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnngca gggaaagcac atgcctgtcc ctccctcatt    3600
agcttcattt ggacaaaaca tgtaaaatcc ggtgtgttgt ggaggccttt tgattgggga    3660
actgtaacgc tgcctatcga gcaacagcac tttaagcagg tggctttgtt caaattaaag    3720
gttcttcttt ttcttttcag                                                 3740

<210> SEQ ID NO 12
<211> LENGTH: 1622
<212> TYPE: DNA
<213> ORGANISM: Homo sapiens
<220> FEATURE:
<221> NAME/KEY: intron
<222> LOCATION: (0)...(0)
<223> OTHER INFORMATION: MGB-STK15 int 2.1
<220> FEATURE:
<221> NAME/KEY: misc_feature
<222> LOCATION: (705)...(989)
<223> OTHER INFORMATION: n= a, t, c, or g

<400> SEQUENCE: 12
gtaaattgaa taatctgtaa tctcattcac atttataaac ccacatggag gttggtcttg      60
tcgggaattc tttccgcctt tactttggat ttaaatttag atcccttact gtgatcctgg     120
atatgaatta gtcacttttc tcgtgttcag taacattttg ctgcttctta gagtagcttt     180
```

```
tttgttctgc tttgtcttat aatcggctgc ttaagtttct atatccctcc actgtatgca    240
ggataatagt aataatgcat ctggcaggag ttcaaaactt ttaaaattgg ccataaatat    300
aaaataatta gaaaaaggct accttgaatt actgtatttg attctaagtt cctatgataa    360
cggccattta aaaaattgct ctatatttaa aatgtttctt tttatttgtc tttgtctgaa    420
tgcctgctgc gttgtggaca gtgtgctaat ttcaggagta actgactttg tatttggaag    480
tcttaacacc ctctctttgt agagcactca taccgttgag ctggggatgg actttgaggc    540
tttcatttct agcacttgtc cctcacttac aatgagctgt tgaagctgaa ggaaatctca    600
tccctcctac cccttttagt ttgattagct gagggtgtta gagttaactt aacaatttaa    660
ggttgtaata cagtacttac aggcgtataa ataatacatt tcaannnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnt aataataata atacatttta gtagtaactt   1020
tgtgaagtgt ctacatttgt ttcctctttg tcagtttttt gctcaattcc attttgtcaa   1080
tacttggaaa atgaaacatt ggttaatcaa tagtacagta ataagcttat tgtggaaaat   1140
cttcgatata tgaaaactta gactcttcta aaacttcatg aagataatac cactgttgaa   1200
cgttttgacg tattttttt tggtcttttt cttaaacgta tattatcaaa gaaatttcaa    1260
tggaactgag attttggcat aaagttttg tatcatagct ttttgccaaa tagcaatgta    1320
gtgtctattt ccaaattatt gagaaatttt agaaagtgtc tccttcatta atggatattt   1380
gttaataaag catgatttt agggtgagg aattggaggg atagaaggt atcattcagg     1440 tattcttagc cacatactaa ctatcctctg gaggtactga ttaaaatacc ttttcacctt   1500
ccatctctta tcagtgacat tcattatttt gctatactag agaacaaact ttgtgaaatt   1560
ctcaatatat tcatcttttg ctttcatgaa tgccagaaag tttattttct cttccattct   1620
ag                                                                 1622
```

<210> SEQ ID NO 13
<211> LENGTH: 1093
<212> TYPE: DNA
<213> ORGANISM: Homo sapiens
<220> FEATURE:
<221> NAME/KEY: intron
<222> LOCATION: (0)...(0)
<223> OTHER INFORMATION: MGB-STK15 int 4.1

<400> SEQUENCE: 13

```
gtaagctttc ttatttacaa agttctgtac tgttctacta gaatatatta tttcgttgca     60
aatttcgttg tgggaactct ggggaaaaaa atgaggcctt tatttgcatt tagaggatat    120 aaatgttttcc agatttccaa tcttaaaaaa aatggaattt tgtgtaatga ggtattttac    180
taggaactca agtgctttaa aaaatggctt tcaaatttag aaaaagcttg tatgaatctt    240
ttatagaaat gtgtggaagt tcctctctgt ccttagaaat aaccactaca tatggttat    300 gcgtctgtac ttttttattg tacaaaagtg caagttttta aaaatagaa tatgttgcag    360 aactatatac tcatatatga ctgagggttt tgacagtatt atagtttag ttctttattg    420 taaaggttgg ctgtaatgtc ttccccaggg ctttttctaaa agcctcctct cagtctctga   480
```

-continued

```
actatctgga ctctagaatg taccgggagg agcgaggaat gaacccacag actcttttgc      540
ttttagcggt ctaacagagg ctaagagtct aaatccactg gttctcatgc cccagctagc      600
ctgtgggctc catcccgctt ccattagtaa cagtggctct gtctccacca ccagagtggt      660
tctccaccca gagagaatta gcacctctgg gactggaggg agcagctggg gttagtttga      720
aacatgcccc cagatggtct ggaagcattc ctccctctct ggtcacttat ccttttgtg      780 gtcttcagcg ttgtcatggc cctgttcctc tgagcatagt acgggcttgg gacatttccc      840
atagagtgct tcaggtctaa aacccgagac tgctccttgt cactgactct cacacctgac      900
ggcagctagg gacgtcaggg tttcatgtcg tggcagctct tgatagtgg ttattgcctt      960 ggttcttgct gaggatgcat attgagtgaa gttggaatac gaaattattt gtagaatgtg     1020
tctgctactc attgaaaatt tgttagaaaa gctttgtttt cttcacattc taaagtgttc     1080
aaattcctcc tag                                                       1093

<210> SEQ ID NO 14
<211> LENGTH: 18
<212> TYPE: DNA
<213> ORGANISM: Artificial Sequence
<220> FEATURE:
<223> OTHER INFORMATION: forward primer

<400> SEQUENCE: 14
agcgcctgtt ccgatctg                                                    18

<210> SEQ ID NO 15
<211> LENGTH: 24
<212> TYPE: DNA
<213> ORGANISM: Artificial Sequence
<220> FEATURE:
<223> OTHER INFORMATION: reverse primer

<400> SEQUENCE: 15
aaccaaagtt ctctgctgaa aacc                                             24

<210> SEQ ID NO 16
<211> LENGTH: 15
<212> TYPE: DNA
<213> ORGANISM: Artificial Sequence
<220> FEATURE:
<223> OTHER INFORMATION: probe

<400> SEQUENCE: 16
ccctgaagca gcaac                                                       15

<210> SEQ ID NO 17
<211> LENGTH: 22
<212> TYPE: DNA
<213> ORGANISM: Artificial Sequence
<220> FEATURE:
<223> OTHER INFORMATION: forward primer

<400> SEQUENCE: 17
ctgttgctgt gtgatgctgt ca                                               22

<210> SEQ ID NO 18
<211> LENGTH: 20
<212> TYPE: DNA
<213> ORGANISM: Artificial Sequence
<220> FEATURE:
<223> OTHER INFORMATION: reverse primer

<400> SEQUENCE: 18
```
cctcagccac tcccttgatc            20

<210> SEQ ID NO 19
<211> LENGTH: 15
<212> TYPE: DNA
<213> ORGANISM: Artificial Sequence
<220> FEATURE:
<223> OTHER INFORMATION: probe

<400> SEQUENCE: 19
tcagggcata agcct                 15

<210> SEQ ID NO 20
<211> LENGTH: 19
<212> TYPE: DNA
<213> ORGANISM: Artificial Sequence
<220> FEATURE:
<223> OTHER INFORMATION: forward primer

<400> SEQUENCE: 20
tccccttgcc tttggagaa             19

<210> SEQ ID NO 21
<211> LENGTH: 19
<212> TYPE: DNA
<213> ORGANISM: Artificial Sequence
<220> FEATURE:
<223> OTHER INFORMATION: reverse primer

<400> SEQUENCE: 21
aaaggcctgg aggcatcaa             19

<210> SEQ ID NO 22
<211> LENGTH: 13
<212> TYPE: DNA
<213> ORGANISM: Artificial Sequence
<220> FEATURE:
<223> OTHER INFORMATION: probe

<400> SEQUENCE: 22
cagcccaaat cct                   13

<210> SEQ ID NO 23
<211> LENGTH: 25
<212> TYPE: DNA
<213> ORGANISM: Artificial Sequence
<220> FEATURE:
<223> OTHER INFORMATION: forward primer

<400> SEQUENCE: 23
cttaatggtg tttagcacag atgca      25

<210> SEQ ID NO 24
<211> LENGTH: 20
<212> TYPE: DNA
<213> ORGANISM: Artificial Sequence
<220> FEATURE:
<223> OTHER INFORMATION: reverse primer

<400> SEQUENCE: 24
ccactgtagc atgcgaagca            20

<210> SEQ ID NO 25
<211> LENGTH: 16
<212> TYPE: DNA

```
<213> ORGANISM: Artificial Sequence
<220> FEATURE:
<223> OTHER INFORMATION: probe

<400> SEQUENCE: 25
caaatgcaca ggaaac                                                    16

<210> SEQ ID NO 26
<211> LENGTH: 19
<212> TYPE: DNA
<213> ORGANISM: Artificial Sequence
<220> FEATURE:
<223> OTHER INFORMATION: forward primer

<400> SEQUENCE: 26
gctctgcggt gtggagtgt                                                 19

<210> SEQ ID NO 27
<211> LENGTH: 21
<212> TYPE: DNA
<213> ORGANISM: Artificial Sequence
<220> FEATURE:
<223> OTHER INFORMATION: reverse primer

<400> SEQUENCE: 27
cacaggcttc gtctggtgtc t                                              21

<210> SEQ ID NO 28
<211> LENGTH: 24
<212> TYPE: DNA
<213> ORGANISM: Artificial Sequence
<220> FEATURE:
<223> OTHER INFORMATION: probe

<400> SEQUENCE: 28
tgcagccctc ttggcaactc tcct                                           24

<210> SEQ ID NO 29
<211> LENGTH: 23
<212> TYPE: DNA
<213> ORGANISM: Artificial Sequence
<220> FEATURE:
<223> OTHER INFORMATION: forward primer

<400> SEQUENCE: 29
aaaatgctgt ctgtgagcct cat                                            23

<210> SEQ ID NO 30
<211> LENGTH: 21
<212> TYPE: DNA
<213> ORGANISM: Artificial Sequence
<220> FEATURE:
<223> OTHER INFORMATION: reverse primer

<400> SEQUENCE: 30
aacccctgcc cactagaaat g                                              21

<210> SEQ ID NO 31
<211> LENGTH: 30
<212> TYPE: DNA
<213> ORGANISM: Artificial Sequence
<220> FEATURE:
<223> OTHER INFORMATION: probe

<400> SEQUENCE: 31
acccaagatg tcatctcctg tagcgtcaca                                     30
```

<210> SEQ ID NO 32
<211> LENGTH: 25
<212> TYPE: DNA
<213> ORGANISM: Artificial Sequence
<220> FEATURE:
<223> OTHER INFORMATION: forward primer

<400> SEQUENCE: 32
aatagatggg tttatggctg aaggt                                          25

<210> SEQ ID NO 33
<211> LENGTH: 23
<212> TYPE: DNA
<213> ORGANISM: Artificial Sequence
<220> FEATURE:
<223> OTHER INFORMATION: reverse primer

<400> SEQUENCE: 33
ctcttggcaa ctctcctgac act                                            23

<210> SEQ ID NO 34
<211> LENGTH: 13
<212> TYPE: DNA
<213> ORGANISM: Artificial Sequence
<220> FEATURE:
<223> OTHER INFORMATION: probe

<400> SEQUENCE: 34
ccgcagagcc gtc                                                       13

<210> SEQ ID NO 35
<211> LENGTH: 25
<212> TYPE: DNA
<213> ORGANISM: Artificial Sequence
<220> FEATURE:
<223> OTHER INFORMATION: forward primer

<400> SEQUENCE: 35
ccatctcaaa aggaaacaag ttctg                                          25

<210> SEQ ID NO 36
<211> LENGTH: 21
<212> TYPE: DNA
<213> ORGANISM: Artificial Sequence
<220> FEATURE:
<223> OTHER INFORMATION: reverse primer

<400> SEQUENCE: 36
gggtggctgg cttctaactc t                                              21

<210> SEQ ID NO 37
<211> LENGTH: 24
<212> TYPE: DNA
<213> ORGANISM: Artificial Sequence
<220> FEATURE:
<223> OTHER INFORMATION: probe

<400> SEQUENCE: 37
ccctgatcaa atgaaagcat cact                                           24

<210> SEQ ID NO 38
<211> LENGTH: 20
<212> TYPE: DNA
<213> ORGANISM: Artificial Sequence
<220> FEATURE:

<223> OTHER INFORMATION: forward primer

<400> SEQUENCE: 38
agaagccagc cacccaatta                                                   20

<210> SEQ ID NO 39
<211> LENGTH: 26
<212> TYPE: DNA
<213> ORGANISM: Artificial Sequence
<220> FEATURE:
<223> OTHER INFORMATION: reverse primer

<400> SEQUENCE: 39
tgtgtcattt ggtatttgtc aagtgt                                            26

<210> SEQ ID NO 40
<211> LENGTH: 26
<212> TYPE: DNA
<213> ORGANISM: Artificial Sequence
<220> FEATURE:
<223> OTHER INFORMATION: probe

<400> SEQUENCE: 40
tgacttgcac aaaacccagt gaatta                                            26

<210> SEQ ID NO 41
<211> LENGTH: 24
<212> TYPE: DNA
<213> ORGANISM: Artificial Sequence
<220> FEATURE:
<223> OTHER INFORMATION: forward primer

<400> SEQUENCE: 41
tggacagaga caagatgtga tgtg                                              24

<210> SEQ ID NO 42
<211> LENGTH: 22
<212> TYPE: DNA
<213> ORGANISM: Artificial Sequence
<220> FEATURE:
<223> OTHER INFORMATION: reverse primer

<400> SEQUENCE: 42
gctggcacct agacaaaaca tg                                                22

<210> SEQ ID NO 43
<211> LENGTH: 15
<212> TYPE: DNA
<213> ORGANISM: Artificial Sequence
<220> FEATURE:
<223> OTHER INFORMATION: probe

<400> SEQUENCE: 43
ccatagggac ccttc                                                        15

<210> SEQ ID NO 44
<211> LENGTH: 25
<212> TYPE: DNA
<213> ORGANISM: Artificial Sequence
<220> FEATURE:
<223> OTHER INFORMATION: forward primer

<400> SEQUENCE: 44
ggtgtcctat tttcctctga agaga                                             25

```
<210> SEQ ID NO 45
<211> LENGTH: 21
<212> TYPE: DNA
<213> ORGANISM: Artificial Sequence
<220> FEATURE:
<223> OTHER INFORMATION: reverse primer

<400> SEQUENCE: 45
tgcaagctga aggtccaaca t                                              21

<210> SEQ ID NO 46
<211> LENGTH: 15
<212> TYPE: DNA
<213> ORGANISM: Artificial Sequence
<220> FEATURE:
<223> OTHER INFORMATION: probe

<400> SEQUENCE: 46
ttctggccaa ttaag                                                     15

<210> SEQ ID NO 47
<211> LENGTH: 21
<212> TYPE: DNA
<213> ORGANISM: Artificial Sequence
<220> FEATURE:
<223> OTHER INFORMATION: forward primer

<400> SEQUENCE: 47
tcattcatgt ggccgtagca t                                              21

<210> SEQ ID NO 48
<211> LENGTH: 19
<212> TYPE: DNA
<213> ORGANISM: Artificial Sequence
<220> FEATURE:
<223> OTHER INFORMATION: reverse primer

<400> SEQUENCE: 48
ggtggagagg gagccaaaa                                                 19

<210> SEQ ID NO 49
<211> LENGTH: 16
<212> TYPE: DNA
<213> ORGANISM: Artificial Sequence
<220> FEATURE:
<223> OTHER INFORMATION: probe

<400> SEQUENCE: 49
cctgtttggg ttttca                                                    16

<210> SEQ ID NO 50
<211> LENGTH: 23
<212> TYPE: DNA
<213> ORGANISM: Artificial Sequence
<220> FEATURE:
<223> OTHER INFORMATION: forward primer

<400> SEQUENCE: 50
agaggatcag aacccgtatg tga                                            23

<210> SEQ ID NO 51
<211> LENGTH: 24
<212> TYPE: DNA
<213> ORGANISM: Artificial Sequence
<220> FEATURE:
<223> OTHER INFORMATION: reverse primer
```

```
<400> SEQUENCE: 51
gggaaacaga gataaggtga acca                                          24

<210> SEQ ID NO 52
<211> LENGTH: 15
<212> TYPE: DNA
<213> ORGANISM: Artificial Sequence
<220> FEATURE:
<223> OTHER INFORMATION: probe

<400> SEQUENCE: 52
tgtgcgtcct gtctg                                                    15

<210> SEQ ID NO 53
<211> LENGTH: 19
<212> TYPE: DNA
<213> ORGANISM: Artificial Sequence
<220> FEATURE:
<223> OTHER INFORMATION: forward primer

<400> SEQUENCE: 53
gggtgacctt gggcttgtg                                                19

<210> SEQ ID NO 54
<211> LENGTH: 23
<212> TYPE: DNA
<213> ORGANISM: Artificial Sequence
<220> FEATURE:
<223> OTHER INFORMATION: reverse primer

<400> SEQUENCE: 54
cttcaaccca tttccagaga gaa                                           23

<210> SEQ ID NO 55
<211> LENGTH: 14
<212> TYPE: DNA
<213> ORGANISM: Artificial Sequence
<220> FEATURE:
<223> OTHER INFORMATION: probe

<400> SEQUENCE: 55
cccgggtccc tgtt                                                     14

<210> SEQ ID NO 56
<211> LENGTH: 21
<212> TYPE: DNA
<213> ORGANISM: Artificial Sequence
<220> FEATURE:
<223> OTHER INFORMATION: forward primer

<400> SEQUENCE: 56
agggtgacct agcagcttgg t                                             21

<210> SEQ ID NO 57
<211> LENGTH: 18
<212> TYPE: DNA
<213> ORGANISM: Artificial Sequence
<220> FEATURE:
<223> OTHER INFORMATION: reverse primer

<400> SEQUENCE: 57
gcctctggcc cagcctta                                                 18

<210> SEQ ID NO 58
<211> LENGTH: 16
```

```
<212> TYPE: DNA
<213> ORGANISM: Artificial Sequence
<220> FEATURE:
<223> OTHER INFORMATION: probe

<400> SEQUENCE: 58
tccctgaccc cagctg                                                        16

<210> SEQ ID NO 59
<211> LENGTH: 25
<212> TYPE: DNA
<213> ORGANISM: Artificial Sequence
<220> FEATURE:
<223> OTHER INFORMATION: forward primer

<400> SEQUENCE: 59
cgtaatgtct cttcctcttc cgtaa                                              25

<210> SEQ ID NO 60
<211> LENGTH: 24
<212> TYPE: DNA
<213> ORGANISM: Artificial Sequence
<220> FEATURE:
<223> OTHER INFORMATION: reverse primer

<400> SEQUENCE: 60
acgaactgag taggttgctg aaaa                                               24

<210> SEQ ID NO 61
<211> LENGTH: 16
<212> TYPE: DNA
<213> ORGANISM: Artificial Sequence
<220> FEATURE:
<223> OTHER INFORMATION: probe

<400> SEQUENCE: 61
tcaagggaca aggaag                                                        16

<210> SEQ ID NO 62
<211> LENGTH: 26
<212> TYPE: DNA
<213> ORGANISM: Artificial Sequence
<220> FEATURE:
<223> OTHER INFORMATION: forward primer

<400> SEQUENCE: 62
cattcacatt tataaaccca catgga                                             26

<210> SEQ ID NO 63
<211> LENGTH: 23
<212> TYPE: DNA
<213> ORGANISM: Artificial Sequence
<220> FEATURE:
<223> OTHER INFORMATION: reverse primer

<400> SEQUENCE: 63
aatccaaagt aaaggcggaa aga                                                23

<210> SEQ ID NO 64
<211> LENGTH: 16
<212> TYPE: DNA
<213> ORGANISM: Artificial Sequence
<220> FEATURE:
<223> OTHER INFORMATION: probe

<400> SEQUENCE: 64
```

```
-continued tggtcttgtc gggaat                                                    16

<210> SEQ ID NO 65
<211> LENGTH: 20
<212> TYPE: DNA
<213> ORGANISM: Artificial Sequence
<220> FEATURE:
<223> OTHER INFORMATION: forward primer

<400> SEQUENCE: 65
gcgaggaatg aacccacaga                                                20

<210> SEQ ID NO 66
<211> LENGTH: 25
<212> TYPE: DNA
<213> ORGANISM: Artificial Sequence
<220> FEATURE:
<223> OTHER INFORMATION: reverse primer

<400> SEQUENCE: 66
gcatgagaac cagtggattt agact                                          25

<210> SEQ ID NO 67
<211> LENGTH: 16
<212> TYPE: DNA
<213> ORGANISM: Artificial Sequence
<220> FEATURE:
<223> OTHER INFORMATION: probe

<400> SEQUENCE: 67
cgctaaaagc aaaaga                                                    16
```

What is claimed is:

1. A method for determining the likelihood of survival, disease recurrence or response to treatment for a human subject with cancer comprising:
   (a) hybridizing a polynucleotide complementary to an intronic RNA sequence of a human target gene other than GRB7 or STMY3 to intronic RNA from a tissue sample that has been obtained from the human subject with cancer or a nucleic acid produced therefrom, to form a complex;
   (b) quantitating the complex to determine the expression level of the human target gene;
   (c) normalizing the expression level of the human target gene relative to the expression level of one or more reference genes in the tissue sample to determine a normalized expression level of the human target gene;
   (d) comparing said normalized expression level of said human target gene to data based on normalized expression of the human target gene in cancer tissue samples obtained from patients of known clinical outcome; and
   (e) determining the likelihood of survival, disease recurrence or response to treatment for the human subject with cancer based on results obtained from step (d).

2. The method of claim 1, wherein the tissue sample is a resected tumor specimen or a tumor biopsy.

3. The method of claim 2, wherein the tissue sample is formalin-fixed paraffin-embedded tissue.

4. The method of claim 2, wherein the tissue sample comprises breast cancer tissue.

5. The method of claim 1, wherein the polynucleotide is a primer and the complex is quantitatively detected using quantitative PCR.

6. The method of claim 1, wherein the polynucleotide is an oligonucleotide.

7. A method for determining the likelihood of survival, disease recurrence or response to treatment for a human subject with cancer comprising:
   (a) hybridizing a polynucleotide that is immobilized on a solid support and complementary to an intronic RNA sequence of a human target gene other than GRB7 or STMY3 to intronic RNA from a tissue sample that has been taken from the human subject with cancer or a nucleic acid produced therefrom, to form a complex;
   (b) quantitating the complex to determine the expression level of the human target gene wherein the complex is quantitatively detected using an array;
   (c) normalizing the expression level of the human target gene relative to the expression level of one or more reference genes in the tissue sample to determine a normalized expression level of the human target gene;
   (d) corn paring the normalized expression level of the human target gene to data based on the normalized expression of the human target gene in cancer tissue samples obtained from patients of known clinical outcome; and
   (e) determining the likelihood of survival, disease recurrence or response to treatment for the human subject with cancer based on results obtained from step (d).

* * * * *

UNITED STATES PATENT AND TRADEMARK OFFICE
CERTIFICATE OF CORRECTION

Page 1 of 1

PATENT NO. : 7,767,391 B2
APPLICATION NO. : 10/783884
DATED : August 3, 2010
INVENTOR(S) : Randy Scott It is certified that error appears in the above-identified patent and that said Letters Patent is hereby corrected as shown below:

In the Claims

In column 72, line 57 the word "corn paring" should be replaced with -- comparing --.

Signed and Sealed this
Twenty-fifth Day of January, 2011

David J. Kappos
*Director of the United States Patent and Trademark Office*